US 8,945,605 B2

(12) United States Patent
Boucher et al.

(10) Patent No.: US 8,945,605 B2
(45) Date of Patent: Feb. 3, 2015

(54) AEROSOL DELIVERY SYSTEMS, COMPOSITIONS AND METHODS

(71) Applicant: Parion Sciences, Inc., Durham, NC (US)

(72) Inventors: Paul Boucher, Cary, NC (US); Richard Boucher, Chapel Hill, NC (US); Brian M. Button, Hillsborough, NC (US); Michael R. Johnson, Chapel Hill, NC (US); James B. Fink, San Mateo, CA (US); Anthony J. Hickey, Chapel Hill, NC (US); Tomas Navratil, Carrboro, NC (US); William Robert Thelin, Chapel Hill, NC (US); Stuart Robert Abercrombie, Cambridge (GB); Philip Jerome Driver, Cambridge (GB); Mark Jeffrey Edhouse, Cambridge (GB); Nicholas O. Heijne, Cambridge (GB); Donal Joseph Taylor, Cambridge (GB); Jonathan Hugh Wilkins, Chichester (GB)

(73) Assignee: Parion Sciences, Inc., Durham, NC (US)

( * ) Notice: Subject to any disclaimer, the term of this patent is extended or adjusted under 35 U.S.C. 154(b) by 0 days.

(21) Appl. No.: 13/831,268

(22) Filed: Mar. 14, 2013

(65) Prior Publication Data
US 2014/0109899 A1 Apr. 24, 2014

Related U.S. Application Data

(63) Continuation-in-part of application No. 13/491,275, filed on Jun. 7, 2012, now Pat. No. 8,778,383.

(60) Provisional application No. 61/494,198, filed on Jun. 7, 2011, provisional application No. 61/496,317, filed on Jun. 13, 2011, provisional application No. 61/639,619, filed on Apr. 27, 2012, provisional application No. 61/639,599, filed on Apr. 27, 2012, provisional application No. 61/733,249, filed on Dec. 4, 2012, provisional application No. 61/693,976, filed on Aug. 28, 2012, provisional application No. 61/734,084, filed on Dec. 6, 2012.

(51) Int. Cl.
A61M 16/00 (2006.01)
A61M 15/00 (2006.01)
A61M 11/06 (2006.01)
A61M 16/06 (2006.01)
A61M 16/14 (2006.01)
A61M 11/00 (2006.01)
A61M 11/02 (2006.01)
A61M 15/08 (2006.01)

(52) U.S. Cl.
CPC ........... *A61M 15/0086* (2013.01); *A61M 11/06* (2013.01); *A61M 16/0666* (2013.01); *A61M 16/14* (2013.01); *A61M 11/003* (2013.01); *A61M 16/0672* (2013.01); *A61M 11/02* (2013.01); *A61M 15/009* (2013.01); *A61M 15/08* (2013.01); *A61M 15/0085* (2013.01); *A61M 2202/0275* (2013.01); *A61M 2206/14* (2013.01); *A61M 2206/16* (2013.01)
USPC ........................................................ 424/434

(58) Field of Classification Search
CPC . A61M 16/16; A61M 16/0666; A61M 16/06; A61M 16/0057; A61K 9/12; A61K 9/0073
See application file for complete search history.

(56) References Cited

U.S. PATENT DOCUMENTS

| | | |
|---|---|---|
| 3,313,813 A | 4/1967 | Cragoe, Jr. |
| 4,159,803 A | 7/1979 | Cameto et al. |
| 4,268,460 A | 5/1981 | Boiarski et al. |
| 4,312,860 A | 1/1982 | Clements |
| 4,479,932 A | 10/1984 | Bodor |
| 4,501,729 A | 2/1985 | Boucher et al. |
| 4,540,564 A | 9/1985 | Bodor |
| 5,002,048 A | 3/1991 | Makiej, Jr. |
| 5,007,419 A | 4/1991 | Weinstein et al. |
| 5,100,806 A | 3/1992 | Macri |
| 5,292,498 A | 3/1994 | Boucher, Jr. |
| 5,388,574 A | 2/1995 | Ingebrethsen |
| 5,437,267 A | 8/1995 | Weinstein et al. |
| 5,483,953 A | 1/1996 | Cooper |
| 5,533,506 A | 7/1996 | Wood |
| 5,614,216 A | 3/1997 | Janoff |
| 5,656,256 A | 8/1997 | Boucher et al. |
| 5,687,715 A | 11/1997 | Landis et al. |
| 5,817,028 A | 10/1998 | Anderson |
| 5,823,179 A | 10/1998 | Grychowski et al. |

(Continued)

FOREIGN PATENT DOCUMENTS

WO WO 2009/049159 4/2009
WO WO 2009/134524 11/2009

OTHER PUBLICATIONS

Office Action for Australian Application No. 2008310734, dated Dec. 14, 2012, 3 pages.

(Continued)

*Primary Examiner* — Bethany Barham
(74) *Attorney, Agent, or Firm* — Cooley LLP

(57) ABSTRACT

An aerosol preparation assembly includes an entrainment chamber defining an entrainment volume. The entrainment chamber includes a gas inlet port, an aerosol inlet port and an outlet port. The entrainment chamber is configured such that a velocity of a flow of a gas within the entrainment volume is less than a velocity of the flow of the gas within the gas inlet port. The entrainment chamber is configured such that at least a portion of inlet aerosol is entrained into the flow of the gas within the entrainment volume to produce an entrained aerosol flow at the outlet port. The particle selection chamber is configured to receive the entrained aerosol flow and produce an outlet aerosol flow. The particle selection chamber and nozzle are collectively configured such that a volumetric median diameter of the outlet aerosol flow is less than a volumetric median diameter of the inlet aerosol.

24 Claims, 32 Drawing Sheets
(1 of 32 Drawing Sheet(s) Filed in Color)

(56) References Cited

U.S. PATENT DOCUMENTS

| | | |
|---|---|---|
| 5,876,970 A | 3/1999 | Benson et al. |
| 6,015,828 A | 1/2000 | Cuppoletti |
| 6,159,969 A | 12/2000 | Yano et al. |
| 6,214,536 B1 | 4/2001 | Boucher, Jr. |
| 6,223,745 B1 | 5/2001 | Hammarlund et al. |
| 6,264,975 B1 | 7/2001 | Boucher, Jr. |
| 6,348,589 B1 | 2/2002 | Pendergast et al. |
| 6,387,886 B1 | 5/2002 | Montgomery et al. |
| 6,457,472 B1 | 10/2002 | Schwartz et al. |
| 6,518,239 B1 | 2/2003 | Kuo et al. |
| 6,527,151 B1 | 3/2003 | Pavkov et al. |
| 6,530,370 B1 | 3/2003 | Heinonen |
| 6,550,476 B1 | 4/2003 | Ryder |
| 6,630,121 B1 | 10/2003 | Sievers et al. |
| 6,818,629 B2 | 11/2004 | Peterson et al. |
| 6,858,614 B2 | 2/2005 | Johnson |
| 6,858,615 B2 | 2/2005 | Johnson |
| 6,903,105 B2 | 6/2005 | Johnson |
| 6,926,911 B1 | 8/2005 | Boucher, Jr. |
| 6,977,246 B2 | 12/2005 | Pendergast et al. |
| 6,992,096 B2 | 1/2006 | Karp et al. |
| 6,995,160 B2 | 2/2006 | Johnson |
| 7,026,325 B2 | 4/2006 | Johnson |
| 7,030,117 B2 | 4/2006 | Johnson |
| 7,064,129 B2 | 6/2006 | Johnson et al. |
| 7,064,148 B2 | 6/2006 | Ueno et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,201,167 B2 | 4/2007 | Fink et al. |
| 7,223,744 B2 | 5/2007 | Yerxa et al. |
| 7,241,766 B2 | 7/2007 | Johnson |
| 7,247,636 B2 | 7/2007 | Johnson |
| 7,267,121 B2 | 9/2007 | Ivri |
| 7,314,046 B2 | 1/2008 | Schroeder et al. |
| 7,317,013 B2 | 1/2008 | Johnson |
| 7,332,496 B2 | 2/2008 | Johnson |
| 7,345,044 B2 | 3/2008 | Johnson |
| 7,345,051 B2 | 3/2008 | Zhou et al. |
| 7,368,447 B2 | 5/2008 | Johnson et al. |
| 7,368,450 B2 | 5/2008 | Johnson |
| 7,368,451 B2 | 5/2008 | Johnson et al. |
| 7,375,107 B2 | 5/2008 | Johnson |
| 7,399,766 B2 | 7/2008 | Johnson |
| 7,405,233 B2 | 7/2008 | Wilde et al. |
| 7,410,968 B2 | 8/2008 | Johnson et al. |
| 7,499,570 B2 | 3/2009 | Zoghlami et al. |
| 7,517,865 B2 | 4/2009 | Meyers |
| 7,537,009 B2 | 5/2009 | Hale et al. |
| 7,553,855 B2 | 6/2009 | Young et al. |
| 7,645,789 B2 | 1/2010 | Hadida Ruah et al. |
| 7,745,442 B2 | 6/2010 | Johnson et al. |
| 7,772,259 B2 | 8/2010 | Karp et al. |
| 7,807,834 B2 | 10/2010 | Johnson |
| 7,820,678 B2 | 10/2010 | Johnson |
| 7,842,697 B2 | 11/2010 | Johnson |
| 7,868,010 B2 | 1/2011 | Johnson et al. |
| 7,875,619 B2 | 1/2011 | Johnson |
| 7,897,577 B2 | 3/2011 | Johansson et al. |
| 7,900,625 B2 | 3/2011 | Kleinstreuer et al. |
| 7,905,229 B2 | 3/2011 | Giroux et al. |
| 7,956,059 B2 | 6/2011 | Johnson |
| 7,981,898 B2 | 7/2011 | Johnson et al. |
| 8,001,963 B2 | 8/2011 | Giroux |
| 8,008,494 B2 | 8/2011 | Johnson |
| 8,022,210 B2 | 9/2011 | Johnson |
| 8,058,278 B2 | 11/2011 | Johnson et al. |
| 8,105,572 B2 | 1/2012 | Condos et al. |
| 8,124,607 B2 | 2/2012 | Johnson |
| 8,143,256 B2 | 3/2012 | Johnson |
| 8,163,758 B2 | 4/2012 | Johnson et al. |
| 8,198,286 B2 | 6/2012 | Johnson |
| 8,245,708 B2 | 8/2012 | Smaldone et al. |
| 8,288,391 B2 | 10/2012 | Johnson et al. |
| 8,324,218 B2 | 12/2012 | Johnson |
| 8,551,534 B2 | 10/2013 | Boucher et al. |
| 2002/0129812 A1 | 9/2002 | Litherland et al. |
| 2003/0091512 A1 | 5/2003 | Adjei et al. |
| 2003/0171332 A1 | 9/2003 | Abraham et al. |
| 2004/0192786 A1 | 9/2004 | Welsh et al. |
| 2004/0244804 A1 | 12/2004 | Olsen et al. |
| 2005/0090505 A1 | 4/2005 | Johnson et al. |
| 2005/0229926 A1 | 10/2005 | Fink et al. |
| 2005/0229928 A1 | 10/2005 | Ivri et al. |
| 2006/0078506 A1 | 4/2006 | Niven et al. |
| 2006/0144399 A1 | 7/2006 | Davidowski et al. |
| 2007/0157931 A1* | 7/2007 | Parker et al. ............ 128/204.23 |
| 2007/0202051 A1 | 8/2007 | Schuschnig |
| 2007/0265280 A1 | 11/2007 | Johnson |
| 2007/0267010 A1 | 11/2007 | Fink et al. |
| 2008/0000473 A1 | 1/2008 | Stephenson et al. |
| 2008/0035141 A1 | 2/2008 | Warner et al. |
| 2008/0066741 A1 | 3/2008 | LeMahieu et al. |
| 2008/0072899 A1 | 3/2008 | Niland et al. |
| 2008/0078382 A1 | 4/2008 | LeMahieu et al. |
| 2008/0167466 A1 | 7/2008 | Johnson et al. |
| 2008/0176863 A1 | 7/2008 | Johnson et al. |
| 2008/0199410 A1 | 8/2008 | Johnson et al. |
| 2008/0223375 A1 | 9/2008 | Cortez et al. |
| 2008/0264415 A1 | 10/2008 | Eason et al. |
| 2008/0293740 A1 | 11/2008 | Johnson et al. |
| 2009/0018144 A1 | 1/2009 | Johnson et al. |
| 2009/0025713 A1 | 1/2009 | Keller et al. |
| 2009/0062308 A1 | 3/2009 | Johnson |
| 2009/0104272 A1 | 4/2009 | Boucher et al. |
| 2009/0203752 A1 | 8/2009 | Campbell et al. |
| 2009/0221597 A1 | 9/2009 | Ruah et al. |
| 2009/0246137 A1 | 10/2009 | Hadida Ruah et al. |
| 2009/0246820 A1 | 10/2009 | Singh et al. |
| 2009/0247458 A1 | 10/2009 | Watson et al. |
| 2009/0253714 A1 | 10/2009 | Johnson et al. |
| 2009/0253736 A1 | 10/2009 | Hadida-Ruah et al. |
| 2009/0263495 A1 | 10/2009 | Watson et al. |
| 2009/0288658 A1 | 11/2009 | Charan et al. |
| 2009/0306009 A1 | 12/2009 | Rosenmeier |
| 2009/0324724 A1 | 12/2009 | Johnson |
| 2010/0074881 A1 | 3/2010 | Boucher et al. |
| 2010/0081957 A1 | 4/2010 | Hyde et al. |
| 2010/0089395 A1 | 4/2010 | Power et al. |
| 2010/0092402 A1 | 4/2010 | Hall et al. |
| 2010/0130547 A1 | 5/2010 | Zhang et al. |
| 2010/0168094 A1 | 7/2010 | Binch et al. |
| 2010/0184739 A1 | 7/2010 | Sheth et al. |
| 2010/0209357 A1 | 8/2010 | Levitt |
| 2010/0209540 A1 | 8/2010 | Warner et al. |
| 2010/0215588 A1 | 8/2010 | Skaliter |
| 2010/0227888 A1 | 9/2010 | Ruah et al. |
| 2010/0258114 A1* | 10/2010 | Cortez et al. ............ 128/200.23 |
| 2010/0316628 A1 | 12/2010 | Breton et al. |
| 2011/0008366 A1 | 1/2011 | Wight et al. |
| 2011/0053831 A1 | 3/2011 | Milech et al. |
| 2011/0056492 A1 | 3/2011 | Longest et al. |
| 2011/0104255 A1 | 5/2011 | Niitsu et al. |
| 2011/0120457 A1 | 5/2011 | Dhuper et al. |
| 2011/0171141 A1 | 7/2011 | Kellerman et al. |
| 2011/0195973 A1 | 8/2011 | Johnson |
| 2011/0214673 A1 | 9/2011 | Masionis |
| 2012/0107414 A1 | 5/2012 | Lipp et al. |
| 2012/0125332 A1 | 5/2012 | Niland et al. |
| 2012/0192863 A1 | 8/2012 | Power et al. |
| 2012/0251594 A1 | 10/2012 | Longest et al. |
| 2013/0074842 A1 | 3/2013 | Boucher |

OTHER PUBLICATIONS

Office Action for U.S. Appl. No. 12/249,175, mailed Nov. 20, 2012, 9 pages.

Office Action for U.S. Appl. No. 12/249,175, mailed Oct. 7, 2010, 11 pages.

International Search Report and Written Opinion for International Application No. PCT/US2008/079519, mailed Dec. 16, 2008.

(56) References Cited

OTHER PUBLICATIONS

International Search Report and Written Opinion for International Application No. PCT/US2012/041333, mailed Nov. 5, 2012.
Office Action for U.S. Appl. No. 12/501,654, mailed Mar. 28, 2012, 12 pages.
Aerogen Limited, AeronebPro Micropump Nebulizer, Instruction Manual, 56 pages (2011).
Berlinski, A. et al., "Nebulized drug admixtures: Effect on aerosol characteristics and albuterol output," J. Aerosol. Med., 19(4):484-490 (2006).
Bernacki, S. H. et al., "Mucin gene expression during differentiation of human airway epithelia in vitro," Am. J. Respir. Cell Mol. Biol., 20(4):595-604 (1999).
Bhashyam, A. et aL, "Aerosol delivery through nasal cannulas: An in vitro study," Journal of Aerosol Medicine, 21(2):1-7 (2008).
Bodor, N. et al., "Controlled delivery of theophylline: Chemistry of 7-Acyl- and 7,7'-Acylditheophylline derivatives," J. Pharm. Sci. 67(8):1045-1050 (1978).
Bodor, N. et al., "Improved delivery through biological membranes. 11. A redox chemical drug-delivery system and its use for brain-specific delivery of phenylethylamine," J. Med. Chem. 26:313-318 (1983).
Bodor, N. et al., "Improved delivery through biological membranes XX: Nicotinamide—Dihydronicotinamide based ester-linked redox carrier systems," J. Pharm. Sci., 75(1):29-35 (1986).
Bompadre, S. G. et al., "G551D and G1349D, two CF-associated mutations in the signature sequences of CFTR, exhibit distinct gating defects," J. Gen Physiol., 129(4):285-298 (2007).
Bonnefous, C. et al., "Discovery of inducible nitric oxide synthase (iNOS) inhibitor development candidate KD7332, Part 1: Identification of a novel, potent, and selective series of quinolinone iNOS dimerization inhibitors that are orally active in rodent pain models," J Med. Chem., 52(9):3047-3062 (2009).
Boucher, R. C., "New concepts of the pathogenesis of cystic fibrosis lung disease," European Respiratory Journal, 23(1):146-158 (2004).
Burg, M. B., "Molecular basis of osmotic regulation," Am. J. Physiol. Renal Physiol., 268:F983-F996 (1995).
Caputo, A. et al., "TMEM16A, a membrane protein associated with calcium-dependent chloride channel activity," Science, 322:590-594 (2008).
Chua, H. L. et al., "The influence of age on aerosol deposition in children with cystic fibrosis," Eur. Respir. J., 7:2185-2191 (1994).
Clunes, M. T. et al., "Front-runners for pharmacotherapeutic correction of the airway ion transport defect in cystic fibrosis," Current Opin. Pharmacol., 8(3):292-299 (2008).
Coakley, R. D. et al., "Abnormal surface liquid pH regulation by cultured cystic fibrosis bronchial epithelium," Proc. Natl. Acad. Sci. USA, 100(26):16083-16088 (2003).
Coates, A. L. et al., "A comparison of amount and speed of deposition between the PARI LC STAR jet nebulizer and an investigational eFlow nebulizer," J. Aerosol. Med. Pulm. Drug. Deliv., 24(3):157-163 (2011).
Davidson, D. J. et al., "A primary culture model of differentiated murine tracheal epithelium," Am. J. Physiol. Lung Cell Mol. Physiol., 279(4):L766-L778 (2000).
De Boeck, K. et al., "Inhaled corticosteroids and lower lung function decline in young children with cystic fibrosis," Eur. Respir. J., 37(5):1091-1095 (2011).
Donaldson, S. et al., "Mucus clearance and lung function in cystic fibrosis with hypertonic saline," The New England Journal of Medicine, 354(3):241-250 (2006).
Duijvestijn, Y. C. M. et al., "Systematic review of N-acetylcysteine in cystic fibrosis," Acta Peadiatr., 88:38-41 (1999).
Duringer, C. et al., "Agonist-specific patterns of $\beta_2$-adrenoceptor responses in human airway cells during prolonged exposure," British Journal of Pharmacology, 158(1):169-179 (2009).
Elkins, M. et al., "A controlled trial of long-term inhaled hypertonic saline in patients with cystic fibrosis," The New England Journal of Medicine, 354(3):229-240 (2006).
Flume, P. A. et al., "Cystic fibrosis pulmonary guidelines. Chronic medications for maintenance of lung health," Am. J. Respir. Crit. Care Med., 176(10):957-969 (2007).
Frerichs, C. et al., "Treatment strategies for cystic fibrosis: what's in the pipeline?" Expert Opin. Pharmacother., 10(7):1191-1202 (2009).
Goralski, J. L. et al., "Osmolytes and ion transport modulators: new strategies for airway surface rehydration," Curr. Opin. Pharmacol., 10(3):294-299 (2010).
Gregory, R. J. et al., "Maturation and function of cystic fibrosis transmembrane conductance regulator variants bearing mutations in putative nucleotide-binding domains 1 and 2," Molecular and Cellular Biology, 11(8):3886-3893 (1991).
Gruber, A. D. et al., "Genomic cloning, molecular characterization, and functional analysis of human CLCA1, the first human member of the family of $Ca^{2+}$-activated Cl- channel proteins," Genomics, 54:200-214 (1998).
Handler, J. S. et al., "Kidney cell survival in high tonicity," Comp. Biochem. Physiol., 117A(3):301-306 (1997).
Hansel, T. T. et al., "A selective inhibitor of inducible nitric oxide synthase inhibits exhaled breath nitric oxide in healthy volunteers and asthmatics," The FASEB Journal, 17:1298-1300 (2003).
Huang P. et al., "Regulation of human CLC-3 channels by multifunctional Ca2+/calmodulin-dependent protein kinase," The Journal of Biological Chemistry, 276(23):20093-20100 (2001).
Hummler, E. et al., "A mouse model for the renal salt-wasting syndrome pseudohypoaldosteronism," Proc. Natl. Acad. Sci USA, 94(21):11710-11715 (1997).
Jayaraman, S. et al., "Noninvasive in vivo fluorescence measurement of airway-surface liquid depth, salt concentration, and pH," The Journal of Clinical Investigation, 107(3):317-324 (2001).
Kerem, E. et al., "Pulmonary epithelial sodium-channel dysfunction and excess airway liquid in pseudohypoaldosteronism," N. Engl. J. Med., 341(3):156-162 (1999).
Lazarowski, E. R. et al., "Nucleotide release provides a mechanism for airway surface liquid homeostasis," J. Biol. Chem., 279(35):36855-36864 (2004).
Matsui, H. et al., "Evidence for periciliary liquid layer depletion, not abnormal ion composition, in the pathogenesis of cystic fibrosis airways disease," Cell, 95:1005-1015 (1998).
Matsui, H. et al., "A physical linkage between cystic fibrosis airway surface dehydration and *Pseudomonas aeruginosa* biofilms," Proc Natl Acad Sci USA, 103(48):18131-18136 (2006).
Megson, I. L. et al., "Nitric oxide donor drugs: current status and future trends," Expert Opin. Investig. Drugs, 11(5):587-601 (2002).
Miller, M. R. et al., "Recent developments in nitric oxide donor drugs," British Journal of Pharmacology, 151(3):305-321 (2007).
Muscara, M. N. et al., "V. Therapeutic potential of nitric oxide donors and inhibitors," Am. J. Physiol. Gastrointest. Liver Physiol., 276(6):G1313-G1316 (1999).
Nash, E. F. et al., "Nebulized and oral thiol derivatives for pulmonary disease in cystic fibrosis (review)," Cochrane Database Syst Rev., 21(1):CD007168 (2009).
O'Callaghan, C. et al., "The science of nebulised drug delivery," Thorax, 52(2):S31-S44 (1997).
Palmer, D. et al., "Synergistic inhibition of vascular smooth muscle cell migration by phosphodiesterase 3 and phosphodiesterase 4 inhibitors," Circulation Research, 82(8):852-861 (1998).
PARI Pharma GmbH eFlow rapid Type 178G1005, Instructions for Use, Mar. 2012.
Quinton, P. M., "Cystic fibrosis: Lessons from the sweat gland," Physiology, 22(3);212-225 (2007).
Ramsey, B. W. et al., "Intermittent administration of inhaled tobramycin in patients with cystic fibrosis," N. Engl. J. Med., 340(1):23-30 (1999).
Randell, S. H. et al., "Effective mucos clearance is essential for respiratory health," Am. J. Respir. Cell. Mol. Biol., 35(1):20-28 (2006).
Ren, C. L. et al., "Relationship between inhaled corticosteroid therapy and rate of lung function decline in children with cystic fibrosis," J. Pediatr., 153(6):746-751 (2008).
Reusable Nebulizers [online] Jun. 2010, [retrieved on Jan. 6, 2011], retrieved from http://www.pari.com/downloads/product-brochures/PARI_LC_Nebs_Brochure_Rev-C_EN.pdf.

(56) References Cited

OTHER PUBLICATIONS

Robinson, M. et al., "Effect of increasing doses of hypertonic saline on mucociliary clearance in patients with cystic fibrosis," Thorax, 52(10):900-903 (1997).
Rowe, S. M. et al., "ΔF508 CFTR processing correction and activity in polarized airway and non-airway cell monolayers," Pulm. Pharmacol. Ther., 23(4):268-278 (2010).
Sanabria, P. et al., "P2Y2 receptor desensitization on single endothelial cells," Endothelium, 15(1):43-51 (2008).
Sawicki, G. S. et al., "High treatment burden in adults with cystic fibrosis: Challenges to disease self-management," J. Cyst. Fibros., 8(2):91-96 (2009).
Schroeder, B. C. et al., "Expression cloning of TMEM16A as a calciumactivated chloride channel subunit," Cell, 134:1019-1029 (2008).
Sood, N. et al., "Increasing concentration of inhaled saline with or without amiloride," Am. J. Respir. Crit. Care Med., 167(2):158-163 (2003).
Sun, H. et al., "The vitelliform macular dystrophy protein defines a new family of chloride channels," Proc Natl Acad Sci USA, 99(6):4008-4013 (2002).
Taube, C. et al., "Airway response to inhaled hypertonic saline in patients with moderate to severe chronic obstructive pulmonary disease," Am. J. Respir. Crit. Care Med., 164(10, Pt. 1):1810-1815 (2001).
Tsunenari, T. et al., "Structure-function analysis of the Bestrophin family of anion channels," J. Biol. Chem., 278(42):41114-41125 (2003).
Vallance, P. et al., "Nitric oxide: therapeutic opportunities," Fundamental & Clinical Pharmacology, 17(1):1-10 (2003).
Vecellio, L. et al., "Deposition of aerosols delivered by nasal route with jet and mesh nebulizers," International Journal of Pharmaceutics, 407:87-94 (2011).
Westerman et al., "Aerosolization of Tobramycin (TOBI®) with the PARI LC PLUS® Reusable Nebulizer: Which Compressor to Use? Comparison of the CR60® to the PortaNeb® Compressor," Journal of Aerosol Medicine and Pulmonary Drug Delivery, 21(3):269-280 (2008).
Yang, Y. D. et al., "TMEM16A confers receptor-activated calcium-dependent chloride conductance," Nature, 455:1210-1215 (2008).
Yerxa, B. R. et al., "Pharmacology of INS37217 [$P^1$-(Uridine 5')-$P^4$-(2'-deoxycytidine 5')tetraphosphate, Tetrasodium Salt], a next-generation $P2Y_2$ receptor agonist for the treatment of cystic fibrosis," J. Pharmacol. Exp. Ther., 302(3):871-880 (2002).
Yoon, S. S. et al., "Anaerobic killing of mucoid *Pseudomonas aeruginosa* by acidified nitrite derivatives under cystic fibrosis airway conditions," J. Clin. Invest., 116(2):436-446 (2006).
Zhou, Z. et al., "The βENaC-overexpressing mouse as a model of cystic fibrosis lung disease," Journal of Cystic Fibrosis, 10(2):S172-S182 (2011).
Al-Sa'Doni, H. H. et al., Mini Rev Med Chem., 5(3):247-254 (2005).
Heyder et al., "Deposition of Particles in the Human Respiratory Tract in the Size Range of 0.005-15 Microns," J Aerosol Sci., 17:811-825 (1986).
Hirsh et al., J. Pharmacol. Exp. Ther., 325(1):77-88 (2008).
Hirsch, S. R. et al., "Sputum liquefying agents: a comparative in vitro evaluation," J. Lab. Clin. Med., 74:346-353 (1969).
Katsumi, H. et al., Cardiovasc Hematol Agents Med Chem., 5(3):204-8 (2007).
LeBrun, P. P. et al., Pharm. World Sci., 22:75-81 (2000).
Ricciardolo, F. L. et al., Curr Drug Targets, 7(6):721-35 (2006).
Shek, E. et al., J. Med. Chem., 19:113-117 (1976).
International Search Report and Written Opinion for International Application No. PCT/US2013/038368, mailed Sep. 16, 2013, 13 pages.
International Search Report and Written Opinion for International Application No. PCT/US2013/073708, mailed Mar. 28, 2014, 15 pages.
Gennaro, A. R., Remington: The Science and Practice of Pharmacy, vol. II, 19th Edition, Mack Publishing Company (1995), p. 1457.
Longest, P. W. et al., "High-efficiency generation and delivery of aerosols through nasal cannula during noninvasive ventilation," Journal of Aerosol Medicine and Pulmonary Drug Delivery, 26(5):266-279 (2013).
Pari Reusable Nebulizer Configurations, PARI Respiratory Equipment, Inc., Brochure—LC Nebulizers, pp. 1-2 (2010).
Murray, M. J. et al. (eds.), Critical Care Medicine: Perioperative Management, American Society of Critical Care Anesthesiologists, Lippincott—Raven Publishers, pp. 431 and 439-445 (1997).
Supplementary European Search Report for European Application No. 12797275.0, mailed Oct. 10, 2014, 7 pages.

\* cited by examiner

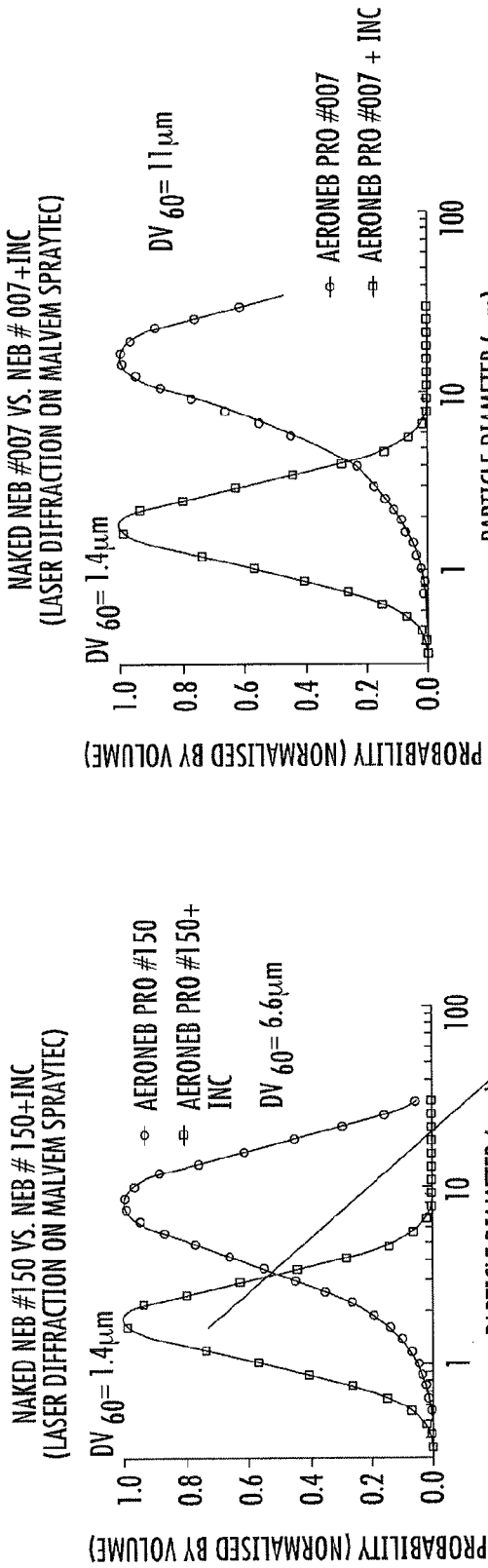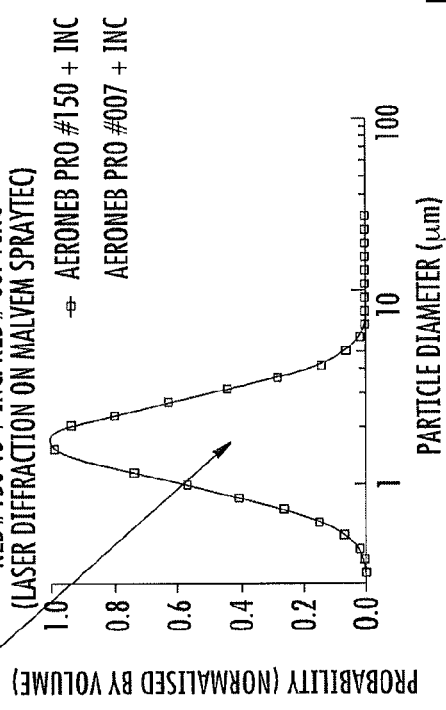
FIG. 14A
FIG. 14B
FIG. 14C

FIG.34B

Aerosol Output with 7% carb-HS (ul/min)

Consistent Aerosol Output

Run Time (min)

NaCl Mass Output with 7% carb-HS (mg/min)

FIG.34A

Consistent Aerosol Particle Size Independent of Input

Aeroneb Pro Nebulizer VMD (μm)

Particle Size VMD (μm)

Phase 1 Safety, Tolerability and Deposition Efficiency Study Design

Deposition Patterns from the Trans-nasal Aerosol Administration with the tPAD Device Compared to Oral Deposition with the Pari LC Star

AEROSOL DELIVERY SYSTEMS, COMPOSITIONS AND METHODS

CROSS REFERENCE TO RELATED APPLICATIONS

This application is a continuation-in-part of U.S. patent application Ser. No. 13/491,275, entitled "Methods of Treatment," filed Jun. 7, 2012, which claims priority to U.S. Provisional Application Ser. No. 61/494,198, entitled "Methods of Treatment," filed Jun. 7, 2011, U.S. Provisional Application Ser. No. 61/496,317, entitled "Methods of Treatment," filed Jun. 13, 2011, and U.S. Provisional Application Ser. No. 61/639,619, entitled "Aerosol Delivery Systems and Related Methods," filed Apr. 27, 2012, each which is incorporated herein by reference in its entirety. This application claims priority to U.S. Provisional Application Ser. No. 61/639,619, entitled "Aerosol Delivery Systems and Related Methods," filed Apr. 27, 2012, U.S. Provisional Application Ser. No. 61/639,599, entitled "Aerosol Delivery Systems and Related Methods," filed Apr. 27, 2012, U.S. Provisional Application Ser. No. 61/733,249, entitled "Systems and Methods of Treatment," filed Dec. 4, 2012, U.S. Provisional Application Ser. No. 61/693,976, entitled "Methods of Treatment," filed Aug. 28, 2012, and U.S. Provisional Application Ser. No. 61/734,084, entitled "Methods of Treatment," filed Dec. 6, 2012, each which is incorporated herein by reference in its entirety.

BACKGROUND

Disclosed embodiments relate generally to aerosol formulations and medical devices, systems and methods for delivering the same. More particularly, disclosed embodiments relate to compositions, systems and methods for delivering medicaments transnasally into the lungs.

Aerosolized medicines are frequently used to treat individuals suffering from respiratory disease. For example, one known method for treating cystic fibrosis (CF) includes restoring hydration to the affected airway surfaces via the inhalation of a hypertonic osmolyte solution, which draws water onto the airway surface. Known methods often administer a seven percent (7%) hypertonic saline (HS) solution. Rehydration of the lubricant periciliary layer (PCL) of the airway surface facilitates mucus clearance (MC) and, therefore, the removal of inhaled infectious agents.

Known methods for delivering aerosolized medicaments include the inhalation of aerosols orally i.e., via an oral mouth piece or a spacer inserted into the patient's mouth. Some known systems for oral inhalation include nebulizer devices, such as jet nebulizers, vibrating mesh nebulizers or ultrasonic nebulizers, or metered dose inhalers (MDIs), or dry powder inhalers (DPIs) to generate respirable aerosol particles (e.g., particles that are <10 μm in diameter) from a liquid medicament, suspension and/or dry powder. Such known systems and methods for oral delivery, however, often present an undesirable time burden on the patient. For example, some known systems require 10-20 minutes to deliver a single dose of medication. For subjects with chronic pulmonary disease for which the treatment regiment includes multiple daily aerosol treatments, the time burden associated with oral drug delivery via jet nebulizers can become substantial. It is not uncommon for patients undergoing treatment for cystic fibrosis to spend 2-3 hours per day on the recommended treatments (Hume et al., Am J Respir Crit Care Med. 2007 Nov. 15; 176(10):957-69 Sawicki et al., J Cyst Fibros. 2009 March; 8(2):91-6).

Moreover, some studies of treatment protocols for cystic fibrosis have suggested that an increased number of treatments per day and/or delivery of higher amounts of salt. For example, two studies have described (1) the short term (two weeks) beneficial effects of inhaled hypertonic saline (HS) four times daily on pulmonary function, MCC, and quality of life (Donaldson et al., N Engl J Med. 2006 Jan. 19; 354(3): 241-50) and (2) the long term (one year) benefits of inhaled HS twice daily on luring function and reduction in pulmonary exacerbations (Elkins et al., N Engl J Med, 354(3):229-40 (2006)). A comparison of the Donaldson versus Elkins suggests that the "more salt" delivered, the greater the benefit in lung function. In particular, subjects in the Donaldson study exhibited a mean improvement in lung function (147 ml improvement in FEV1) with four times daily administration (3.6 ml of 7% HS predicted pulmonary deposition), which as approximately twice the improvement that was achieved in the Elkins study (68 ml improvement in FEV1) with B.I.D. dosing (1.58 ml of 7% HS predicted pulmonary deposition). Thus, as treatment regimens are improved to maximize the benefits of HS administration, the time burden associated with oral drug delivery via jet nebulizers will likely be exacerbated.

In addition to the undesirable time burden associated with known methods for oral delivery of aerosolized medicaments, known methods of periodic delivery over relatively short time periods (e.g., 5 to 20 minutes per treatment) results in the delivery of medicaments as concentrated "boluses", which can be undesirable. The delivery of medicaments as a bolus leads to a rapid increase of the active therapeutic agent at the targeted location over a short period of time, often at levels above the necessary therapeutic concentration. Similarly, bolus delivery can lead to high systemic exposure to such agents. Such peak local and systemic concentrations following bolus administration of inhaled aerosols can lead to undesirable safety and tolerability profiles, which may prevent adoption of the therapy into the standard of care. For example, chronic inhaled corticosteroids have been shown to have disease-modifying impact on the rate of lung function decline in CF (Ren et al, J Pediatr., 153(6):746-51 (2004 de Boeck et al., Eur Respir J, 37(5): 1091-5 (2011)). Such methods, however, are accompanied by patients' decreased linear growth, and increased insulin/oral hypoglycemic use due to the systemic exposure. As such, inhaled corticosteroids are not recommended for general treatment of CF lung disease (Flume et al, Am J Respir Crit Care Med. 2007 Nov. 15; 176(10):957-69).

In response to the high time burden associated with oral delivery and/or the desire increase the mass of salt delivered, some known nebulizers have been developed to deliver an aerosol dose more quickly, such as, for example, within two to five minutes. Although such known systems and methods may slightly shorten the treatment duration, even short aerosol administrations of several different therapeutic agents several times per day can result in a significant treatment burden. Moreover, as discussed above, some therapeutic agents may not be suitable (effective and/or safe) for administration via an aerosol bolus delivered over short periods.

For example, delivery of up to 12% HS was evaluated (Robinson et al., Thorax. 1997 October; 52(10):900-3), and resulted in the conclusion that HS concentrations higher than seven percent are not well tolerated using known methods of aerosol delivery. Lack of tolerability of HS therapy can be related to high rates of emission of NaCl mass from the nebulizer mouthpiece, which leads to high exposure of oropharyngeal surfaces to HS. Similarly, the high rates of NaCl mass deposition in the lung can lead to adverse events such as chest tightness, cough and acute decreases in lung function (Elkins et al). In chronic obstructive pulmonary disease (COPD), high rates of NaCl delivery initiate histamine release, which contributes to airway spasm (Taube et al. Am J Respir Crit Care Med. 2001 Nov. 15; 164 (10 Pt 1: 1810-5). On a cellular level, administration of high rate of NaCl mass to the airway epithelium substantially dehydrates the airway epithelial cells, which can lead to cell shrinkage, inhibition of ciliary beat frequency and release of inflammatory stimuli leading to pulmonary inflammation (Zhou et al., Journal of Cystic Fibrosis Vol, IOSupplement 1, Page S I 8). Accordingly, using known methods to increase the rate of delivery of an aerosolized medicament can be undesirable.

Other known methods for delivering aerosolized medicaments include transnasal delivery of the aerosolized medicament to the affected airways. Some known systems for transnasal delivery include a long, relatively narrow nasal cannula, through which the aerosolized medicament is transported. Such known systems and methods for transnasal delivery, however, often result in undesirable rainout and/or sputtering of the medicament as it passes through the nasal cannula.

Moreover, known systems and methods for transnasal delivery often result in very low deposition efficiencies of aerosol deposition in the lung due to aerosol impaction in the nasal passages. For example, a study by Chua et al. showed overall deposition efficiencies of less than about three percent (as compared with deposition efficiencies of approximately 15 percent or higher for oral delivery of aerosolized medicaments). In particular, the study showed that only 0.3% of the emitted dose was deposited in the lungs in infants 0.3 to 1.4 month of age; only 2.9% of the emitted dose deposited in the lungs of pediatric subjects 6.3 to 11.5 years of age; and only 2.7% of the emitted dose deposited in the lungs of subjects 15 years of age and older. (See generally H Chua et al., *Eur. Respir. J.* 7, 2185-2191 (1994)). More recently, Vecellio et al. reported a 3.7% pulmonary deposition efficiency based on the dose from a nasal sonic jet nebulizer.

Thus, a need exists for improved compositions, systems and methods for delivering medicaments transnasally into the lungs.

SUMMARY

Medicament compositions, delivery systems, delivery apparatus, and methods of delivery are described herein. In some embodiments, an apparatus includes an entrainment chamber defining an entrainment volume. The entrainment chamber includes a gas inlet port, an aerosol inlet port and an outlet port. The gas inlet port is configured to fluidically couple a gas source to the entrainment volume. The entrainment chamber is configured such that a velocity of a flow of a gas within the entrainment volume is less than a velocity of the flow of the gas within the gas inlet port. The aerosol inlet port is configured to receive an inlet aerosol produced by an aerosol generator. The entrainment chamber is configured such that at least a portion of the inlet aerosol is entrained into the flow of the gas within the entrainment volume to produce an entrained aerosol flow at the outlet port. The apparatus also includes a nozzle in fluidic communication with the outlet port of the entrainment chamber, where the nozzle is configured to accelerate the entrained aerosol flow. The apparatus further includes a particle selection chamber including a cannula coupling port that is configured to be coupled to a nasal cannula. The particle selection chamber is configured to receive the entrained aerosol flow from the nozzle and produce an outlet aerosol flow. The particle selection chamber and nozzle are collectively configured such that a volumetric median diameter of the outlet aerosol flow is less than a volumetric median diameter of the inlet aerosol.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 14A-14C are graphs of the aerosol particle size as a function of normalized probability for the aerosol delivery system of FIG. 6.

FIGS. 34A-34B are plots illustrating performance characteristics of an aerosol preparation assembly according to an embodiment. In particular, FIG. 34A is a plot of particle size distribution from an aerosol preparation assembly compared to the output from a conventional nebulizer. FIG. 34B is a plot of NaCl-containing aerosol output from an aerosol preparation assembly according to an embodiment.

DETAILED DESCRIPTION

Figure 1:
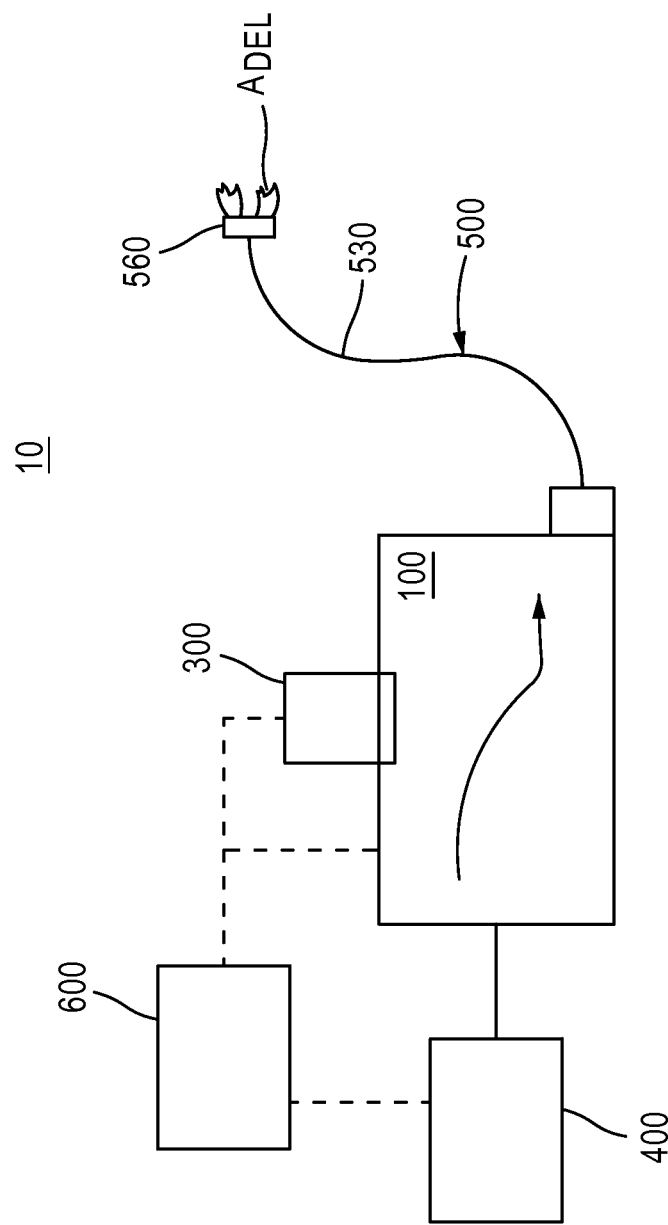
FIG. 1 is a schematic block diagram of an aerosol delivery system according to an embodiment.

Medicament compositions, delivery systems and methods of delivery are described herein. In some embodiments, an apparatus includes an entrainment chamber, a nozzle and a particle selection chamber. The entrainment chamber defines an entrainment volume. The entrainment chamber includes a gas inlet port, an aerosol inlet port and an outlet port. The gas inlet port is configured to fluidically couple a gas source to the entrainment volume. The entrainment chamber is configured such that a velocity of a flow of a gas within the entrainment volume is less than a velocity of the flow of the gas within the gas inlet port. The aerosol inlet port is configured to receive an inlet aerosol produced by an aerosol generator. The entrainment chamber is configured such that at least a portion of the inlet aerosol is entrained into the flow of the gas within the entrainment volume to produce an entrained aerosol flow at the outlet port.

The nozzle is in fluidic communication with the outlet port of the entrainment chamber, and is configured to accelerate the entrained aerosol flow. The particle selection chamber is configured to receive the entrained aerosol flow from the nozzle and produce an outlet aerosol flow. The particle selection chamber includes a cannula coupling port that is configured to be coupled to a nasal cannula. The particle selection chamber and nozzle are collectively configured such that a volumetric median diameter of the outlet aerosol flow is less than a volumetric median diameter of the inlet aerosol.

In some embodiments, an apparatus includes an entrainment chamber and a particle selection chamber. The entrainment chamber defines an entrainment volume and includes a gas inlet port, an aerosol inlet port and an outlet port. The gas inlet port is configured to fluidically couple a gas source to the entrainment volume. The aerosol inlet port is configured to receive an inlet aerosol produced by an aerosol generator. The entrainment chamber is configured such that at least a portion of the inlet aerosol is entrained into a flow of a gas within the entrainment volume to produce an entrained aerosol flow at the outlet port.

The particle selection chamber includes a cannula coupling port that is configured to be coupled to a nasal cannula. The particle selection chamber is further configured to receive the entrained aerosol flow from the outlet port of the entrainment chamber and produce an outlet aerosol flow (e.g., to the cannula coupling port). The particle selection chamber is further configured to extract a portion of the entrained aerosol from the entrained aerosol flow such that a volumetric median diameter of the outlet aerosol flow is less than a volumetric median diameter of the inlet aerosol. The cannula coupling port includes a cannula nozzle and a coupling portion. The coupling portion is configured to be coupled to the nasal cannula such that an inner wall of the cannula nozzle and an inner wall of the nasal cannula form a substantially continuous surface.

In some embodiments, an apparatus includes an entrainment chamber and a particle selection chamber. The entrainment chamber defines an entrainment volume and includes a gas inlet port, an aerosol inlet port, an outlet port and a first recirculation port. The gas inlet port is configured to fluidically couple a gas source to the entrainment volume. The aerosol inlet port is configured to receive an inlet aerosol produced by an aerosol generator. The entrainment chamber is configured such that a first portion of the inlet aerosol is entrained into a flow of a gas within the entrainment volume to produce an entrained aerosol flow at the outlet port. A second portion of the inlet aerosol is collected within the entrainment chamber. The first recirculation port is configured to receive the second portion of the inlet aerosol, where the first recirculation port fluidically coupled to the aerosol generator via a first recirculation pathway that excludes the entrainment chamber.

The particle selection chamber includes a cannula coupling port that is configured to be coupled to a nasal cannula. The particle selection chamber is configured to receive the entrained aerosol flow from the outlet port of the entrainment chamber and to produce an outlet aerosol flow (e.g., to the cannula coupling port). The particle selection chamber is further configured to extract a portion of the entrained aerosol from the entrained aerosol flow such that a volumetric median diameter of the outlet aerosol flow is less than a volumetric median diameter of the inlet aerosol. The second recirculation port is configured to receive the extracted portion of the entrained aerosol. The second recirculation port is fluidically coupled to the aerosol generator via a second recirculation pathway that excludes the entrainment chamber.

In some embodiments, a drug cartridge includes a medicament container, an interface member and a valve. The medicament container contains a liquid medicament. The interface member is coupled to the medicament container and is configured to be removably coupled to an inlet opening defined by an aerosol generator. The valve is configured to limit flow of the liquid medicament from the medicament container into a reservoir of the aerosol generator.

In some embodiments, an aerosol suspension of liquid particles comprises an active agent and a buffering agent. The aerosol particles have a volume median diameter (VMD) from about 0.5 μm to about 2.5 μm and there are not more than about 10% aerosol particles larger than 4 μm based on volume normalized amounts. The aerosol particles produce a deposition efficiency of greater than about 3% on lung airway surfaces via transnasal administration and maintain the physiological pH of lung airway surfaces upon delivery.

In some embodiments, a method of treating a disease or condition associated with either lung of a subject comprises transnasally administering an effective amount of an aerosol suspension of liquid particles which comprises an active agent and a buffering agent. The aerosol particles have a volume median diameter (VMD) from about 0.5 μm to about 2.5 μm, and there are not more than about 10% aerosol particles larger than 4 μm based on volume normalized amounts. The aerosol particles produce a deposition efficiency of greater than about 3% on lung airway surfaces and maintain the physiological pH of lung airway surfaces upon delivery.

In some embodiments, a system for treating a disease or condition associated with either lung of a subject comprises a pharmaceutical formulation comprising a hypertonic saline solution and a bicarbonate buffering agent, and further comprises an aerosol delivery device configured to generate an aerosol comprising the pharmaceutical formulation. The aerosol delivery device includes a nasal cannula assembly configured to deliver the aerosol to the lungs of the subject. The aerosol has a volume median diameter (VMD) from about 0.5 μm to about 2.5 μm and there are not more than about 10% aerosol larger than 4 μm based on volume normalized amounts. The aerosol produces a deposition efficiency of greater than about 3% on lung airway surfaces via transnasal administration and maintains the physiological pH of lung airway surfaces upon delivery.

In some embodiments, aerosol delivery systems are configured to produce a steady aerosol output performance for extended periods of time (e.g., from between 0.5 hours to 8 hours per day; and/or for up to 24 hours/day). Rainout and sputtering can be reduced and/or eliminated over extended periods of treatment times, such as when a subject or patient is sleeping. This arrangement allows the aerosol delivery system to deliver the aerosol to the subject's nose via a nasal cannula for pulmonary delivery. In some embodiments, rainout may be reduced without substantially decreasing the aerosol output (volume output) of the system. Accordingly, the methods, apparatus, and systems described herein can enable extended aerosol administration overnight via a nasal cannula while the patient is asleep. Such extended aerosol administration would eliminate the daytime treatment burden presented with conventional bolus aerosol delivery treatments. Furthermore, such extended aerosol administration would enable improvement in efficacy, effectiveness, safety and tolerability for therapeutic agents benefiting from prolonged delivery at slower rates compared to bolus aerosol delivery.

Definitions

Subjects to be treated by the methods of the disclosed embodiments include both human subjects and animal subjects (e.g., dog, cat, monkey, chimpanzee) for veterinary purposes. The subjects may be male or female and may be any suitable age, e.g., neonatal, infant, juvenile, adolescent, adult, or geriatric. In some embodiments, the subjects are preferably mammalian.

The terms "a" and "an," when used to modify the ingredient of a composition, such as, active agent, buffering agent, and osmylate, do not denote a limitation of quantity, but rather denote the presence of at least one of the referenced item. The term "or" or "and/or" is used as a function word to indicate that two words or expressions are to be taken together or individually. The terms "comprising," "having," "including," and "containing" are to be construed as open-ended terms (i.e., meaning "including, but not limited to"). The endpoints of all ranges directed to the same component or property are inclusive and independently combinable.

"Osmolyte" active compounds as used herein refers to molecules or compounds that are osmotically active (i.e., are "osmolytes"). "Osmotically active" compounds are known (see, e.g., R. Boucher et al., *Multiple Nebulizer System*, US Patent Application 20100074881 (published Mar. 25, 2010) and may be membrane-impermeable (i.e., essentially non-absorbable) on the airway or pulmonary epithelial surface.

"Airway surface" and "pulmonary surface," as used herein, include pulmonary airway surfaces such as the bronchi and bronchioles, alveolar surfaces, and nasal and sinus surfaces.

"Saline" as used herein refers to a solution comprised of, consisting of, or consisting essentially of sodium chloride in water. Saline can be hypertonic, isotonic, or hypotonic. In some embodiments, saline can comprise sodium chloride in an amount of from about 0.1% to about 40% by weight, or any range therein, such as, but not limited to, about 0.1% to about 10%, about 0.5% to about 15%, about 1% to about 20%, about 5% to about 25%, about 10% to about 40%, or about 15% to about 35% by weight (in mg/100 mL). In certain embodiments, sodium chloride is included in a solution in an amount of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% by weight (in mg/100 mL), or any range therein.

"Hypertonic saline" as used herein refers to a solution comprised of, consisting of, or consisting essentially of greater than 0.9 wt % sodium chloride in water. In general, the sodium chloride is included in the solution in an amount of from about 0.9% to about 40% by weight, or any range therein, such as, but not limited to, about 1% to about 15%, about 5% to about 20%, about 5% to about 25%, about 10% to about 40%, or about 15% to about 35% by weight. In certain embodiments, sodium chloride is included in the solution in an amount of about 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40% by weight, or any range therein.

"Hypotonic saline" as used herein refers to a solution comprised of, consisting of, or consisting essentially of less than 0.9 wt % sodium chloride in water. In some embodiments, sodium chloride is included in the solution in an amount of about 0.9%, 0.8%, 0.7%, 0.6%, 0.5%, 0.4%, 0.3%, 0.2%, 0.1% by weight, or any range therein.

"Isotonic saline" as used herein refers to a solution comprised of, consisting of, or consisting essentially of 0.9 wt % sodium chloride in water.

According to some embodiments, saline (e.g., hypertonic saline) can include an excipient. An excipient can be a pharmaceutically acceptable excipient. "Pharmaceutically acceptable" as used herein means that the compound or composition is suitable for administration to a subject to achieve the treatments described herein, without unduly deleterious side effects in light of the severity of the disease and necessity of the treatment. Exemplary excipients include, but are not limited to, a buffer and/or a buffering agent (e.g., an anion, a cation, an organic compound, a salt, etc.). Exemplary buffers include, but are not limited to, carbonic acid/carbonate/bicarbonate-based buffers, disodium hydrogen phthalate/sodium dihydrogen orthophosphate-based buffers, tris(hydroxymethyl)aminomethane/hydrochloric acid-based buffers, barbitone sodium/hydrochloric acid-based buffers, and any combination thereof. Exemplary buffering agents include, but are not limited to, carbonic acid, carbonate, bicarbonate, disodium hydrogen phthalate, sodium dihydrogen orthophosphate, tris(hydroxymethyl)aminomethane, hydrochloric acid, barbitone sodium, dissolved $CO_2$ (e.g., $CO_2$ formulated at a pH of greater than 6.6), and any combination thereof. In certain embodiments, saline comprises a bicarbonate buffer excipient, such as a bicarbonate anion ($HCO_3^-$). In some embodiments, hypertonic saline can include sodium bicarbonate, sodium carbonate, carbonic acid, and/or dissolved $CO_2$ formulated at a pH of greater than 6.5. Additional ingredients can be included as desired depending upon the particular condition being treated, as discussed further below.

"Substantially dehydrate" as used herein with respect to airway epithelial cells refers to cellular dehydration sufficient to result in: (a) a loss of at least 5, 10, 15 or 20 percent of cell volume; (b) inhibition of the beat of cilia projecting from those cells by at least 20 or 40 percent; (c) a decrease in the ability of the dehydrated cells to donate water to, and thereby hydrate, their overlying airway surface liquid/mucus layer; and/or (d) produce pro-inflammatory states such as increased IL-8 secretion.

"Hydrate," "hydration," and grammatical variants thereof, as used herein, refers to bringing, placing, drawing and/or the like water onto an airway surface of a lung. In certain embodiments, hydration is enhanced by a method of the some embodiments. Hydration reflects (a) an increase in the volume of airway surface liquid above the epithelial cells of at least about 1%, 5%, 10%, 15%, 20%, 100%, 100%, 500%, 1,000% or more, (b) dilution of mucins and/or mucus, and/or c) dilution of inflammatory materials.

The term "drug," "active," "medication," "medicament," or "active pharmaceutical ingredient," or variants thereof, as used herein includes a pharmaceutically acceptable and therapeutically effective compound, pharmaceutically acceptable salts, stereoisomers and mixtures of stereoisomers, solvates, and/or esters thereof.

The term "derivative" as used herein refers to a chemical compound that is derived from or obtained from a parent compound and contains essential elements of the parent compound, but typically has one or more different functional groups. Such functional groups can be added to a parent compound, for example, to improve the molecule's solubility, absorption, biological half life, fluorescent properties, and the like, or to decrease the toxicity of the molecule, eliminate or attenuate any undesirable side effect of the molecule, and the like. It is to be understood that the term "derivative" encompasses a pharmaceutically acceptable salt, as described herein. An "active derivative" is a derivative that retains an activity recited herein (e.g., the ability to deliver a bioactive compound to a cell, cytotoxic activity).

The phrase "pharmaceutically acceptable salt(s)," as used herein, means those salts of the presently disclosed compounds that are safe and effective for use in a subject and that possess the desired biological activity.

Throughout the present specification, the terms "about" and/or "approximately" may be used in conjunction with numerical values and/or ranges. The term "about" is understood to mean those values near to a recited value. For example, "about 1200 [units]" may mean within ±25% of 1200 (e.g., from 30 to 50), within ±20%, ±15%, ±10%, ±9%, ±8%, ±7%, ±7%, ±5%, ±4%, ±3%, ±2%, ±1%, less than ±1%, or any other value or range of values therein or therebelow. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 70-70, etc.). Furthermore, all values within a given range may be an endpoint for the range encompassed thereby (e.g., the range 50-80 includes the ranges with endpoints such as 55-80, 50-75, etc.).

As used herein, the term "volumetric median diameter" or "VMD" of an aerosol is the particle size diameter identified such that half of the mass of the aerosol particles is contained in particles with larger diameter than the VMD, and half of the mass of the aerosol particles is contained in particles with smaller diameter than the VMD.

As used herein, the term "rainout" refers to liquid (and/or a liquid/solid solution) from an aerosol that collects on a surface and/or is otherwise removed from the flow of the aerosol. Rainout can occur due to any suitable mechanism, such as inertial impaction, gravitational sedimentation or condensation on a surface. The term "sputtering" refers to rainout that exits from a device (e.g., from the nasal prongs of a nasal cannula) or otherwise separates from the surface upon which the rainout is collected.

As used herein, the term "deposition efficiency" refers to the percentage of the delivered dose that is deposited into the area of interest. Thus, the deposition efficiency of a method and/or system for delivering an aerosolized medicament into the lungs is the amount by mass of the aerosol deposited into the lungs divided by the total amount of the aerosol delivered by the system to the nares.

Delivery Systems

FIG. 1 is a schematic block diagram of an aerosol delivery system 10 according to an embodiment for delivering aerosolized medicaments ($A_{DEL}$) according to an embodiment. The aerosol delivery system 10 can be used to deliver any of the compositions according to any of the methods described herein. The system 10 includes an aerosol preparation assembly 100, a medicament cartridge 300, a source of gas 400, a nasal cannula assembly 500, and a controller 600.

The aerosol preparation assembly 100 can be configured to produce aerosolized medicament having specific characteristics, such as a desired particle size (e.g. VMD of between 1 and 2 microns) and/or size distribution, aerosol concentration, aerosol volume, medicament amount, flow rate, terminal velocity, and/or the like. The aerosol preparation assembly 100 can be configured to generate both solid (i.e., fine solid particles in gas) and liquid (liquid droplets in gas) aerosols, depending on the medicament. Any suitable mechanism can be employed for generating aerosol including, but not limited to. as an aerosol spray (similar to commonly used aerosol cans), an atomic nozzle (such as those based on the Venturi effect), any type of nebulizer suitable for medicament delivery (mechanical, electrical, a current jet nebulizer, an ultrasonic nebulizer, a vibrating mesh nebulizer etc.), an electrospray, a vibrating orifice aerosol generator (VOAG), droplet expulsion techniques (e.g. such as commonly used in ink jet printers), micro-scale nozzle membranes (e.g. such as can be generated via lithography, and particularly silicon wafer lithography), and/or the like. The disclosed embodiments can be configured to generate the aerosol independent of certain gas characteristics, such as, but not limited to, humidity, temperature, and/or the like. Accordingly, the aerosol preparation assembly 100, and the other aerosol preparation assemblies disclosed herein can receive inlet fluids (e.g., liquid medicament and inlet gas) having a wide range of input characteristics (e.g., droplet size, humidity, temperature), and can produce a repeatable outlet aerosol.

Generally, any suitable design of the aerosol preparation assembly 100 that permits generation and delivery of aerosolized medicament as described herein can be employed. For example, the aerosol preparation assembly 100 can be configured to generate aerosol directly from liquid medicament and an entrainment gas. In another example, the aerosol preparation assembly 100 can be configured to generate an aerosol of the medicament prior to entrainment with the entrainment gas. The initial aerosol can be generated in a different stage of the aerosol preparation assembly 100 than another stage where the entrainment of the aerosol occurs. Further, any such stages of the aerosol preparation assembly 100 can be monolithically or separately constructed. In some embodiments, the aerosol preparation assembly 100 can be configured to modify one or more characteristics of the aerosolized medicament to better produce the specific characteristics associated with the indication to be treated, and can accordingly comprise any suitable component necessary for performing such function(s). For example, the aerosol preparation assembly 100 can be configured to increase the speed of the generated aerosol as can be required to ensure delivery once the aerosol leaves the aerosol preparation assembly 100. Further, in some embodiments, the aerosol preparation assembly 100 can include a machine-readable label and/or electronic circuit system for communication with the controller 600 for monitoring, control, and/or generally modulating any of the functionality of the aerosol preparation assembly 100 as described herein.

The medicament cartridge 300 contains the medicament(s) to be aerosolized, and can be configured to be removably coupled and/or operatively coupled to the aerosol preparation assembly 100. The medicament cartridge 300 can be configured to receive the medicament(s) at any suitable time, including at pre-filling and/or while coupled to the aerosol preparation assembly 100, and can be refillable or single use/disposable. The medicament cartridge 300 can be configured according to medicament-specific conditions to account for storage/delivery needs of the medicament. In some embodiments, the medicament cartridge 300 can include any keying feature that restricts the use of the medicament cartridge 300 to prespecified delivery systems, such as the aerosol preparation assembly 100. Additional components for handling and/or manipulating the medicament may be formed as part of the medicament cartridge 300, such as filters, for example. Further, in some embodiments, the medicament cartridge 300 can include a machine-readable label and/or electronic circuit system for communication with the controller 600 for monitoring the medicament levels in the medicament cartridge, for controlling access/delivery of the medicament, and/or the like.

The gas source 400 can provide airflow in a manner appropriate for the aerosol preparation assembly 100 (i.e., to produce aerosolized medicaments ($A_{DEL}$) having the desired characteristics). In other words, the gas source 400 can, in some embodiments, be tuned to the specifications of input requirements of the aerosol preparation assembly 100. For example, in some embodiments, the gas source 400 can be operated to produce steady, laminar flow, while in other embodiments, the gas source can produce flow having periodic changes in local velocity, pressure, and/or any suitable flow parameter. Although shown here as a single gas source 400 for simplicity, it is understood to represent multiple gas sources operable to delivery one or more gases, each operating in a similar manner as described here. The gas source 400 can be of any suitable form, such as a pump, a hospital supply system, a gas tank (e.g. most medical gas supplies), and/or the like. In some embodiments, the gas source need not be humidified and/or otherwise controlled for humidity, temperature, and/or the like. Additional components for handling and/or manipulating the gas may be formed as part of the gas source 400, such as pumps, connecting lines, compliance chambers, filters, valves, regulators, pressure gauges, and/or the like. Further, in some embodiments, the gas source 400 can include a machine-readable label and/or electronic circuit system (e.g. a hydraulic control system) for communication with the controller 600 for monitoring gas levels in the gas source, for controlling access/delivery of the gas, for controlling gas flow parameters, and/or the like.

The cannula assembly 500 is configured to deliver the aerosolized medicament $A_{DEL}$ from the aerosol preparation assembly 100 to nares of patient, and can be configured to be removably coupled and/or operatively coupled to the aerosol preparation assembly 100. In some embodiments, the cannula assembly 500 includes at least a face piece tube 530, and can additionally include a face piece 560. In other words, in some embodiments, the tube 530 can suffice for patient delivery of the aerosolized medicament. The tube 530 can be appropriately sized and designed for operation with the aerosol preparation assembly 100 and per the desired delivery characteristics of the aerosolized medicament. For example, it may be desired that the tube 530 be of a certain minimum rigidity to prevent excessive bending that could, in turn, affect flow characteristics detrimentally. In some embodiments, additional structures may be formed within the tube, such as one way valves that prevent condensed liquids/particles from flowing into the patient's nostrils, but permit backflow of the condensed liquids/particles into the aerosol preparation assembly 100, for example. As another example, and as will be explained in more detail later, one or more filtering structures that change the particle size distribution of the aerosolized medicament can also be present in the tube 530.

The face piece 560 can be removably coupled and/or operatively coupled to the tube 530, and can be appropriately sized and designed per the desired delivery characteristics of the aerosolized medicament. As generally discussed above for the tube 530, the face piece 560 can constitute filters, valves, and/or the like for modifying flow characteristics and or the aerosolized medicament.

In some embodiments, the face piece 560 can have a separate outlet/prong for delivering the aerosolized medicament for each nasal cannula of the patient. In some embodiments, the face piece 560 can be further configured for ease and comfort of use, by including features such as claspers, sticky pads, and/or the like to hold the face piece 560 in position on the nose of the patient.

The controller 600 can be configured for monitoring, control, and/or modulating any of the functionality of the aerosol preparation assembly 100, the medicament cartridge 300, the gas source 400, and/or any other component associated with the system 10. In some embodiments, the controller 600 can include at least a processor and a memory. In some embodiments, the controller 600 can receive signal inputs and produce outputs to control and/or operate the system 10, as described herein.

The memory can be any suitable computer memory. For example, the memory can be random-access memory (RAM), read-only memory (ROM), flash memory, erasable programmable read-only memory (EPROM), electrically erasable programmable read-only memory (EEPROM), and/or other suitable memory. In some embodiments, the memory can be configured to store code representing processor instructions for execution by the processor and/or store data received from any device(s) operatively coupled to the processor.

The processor can be any suitable processor capable of executing computer instructions. Each module in the processor can be any combination of hardware-based module (e.g., a field-programmable gate array (FPGA), an application specific integrated circuit (ASIC), a digital signal processor (DSP) and/or software-based module (e.g., a module of computer code stored in memory and/or executed at the processor) configured to execute a specific function of the system 10. The processor can be a microcontroller, a FPGA, an ASIC, or any other suitable processor configured to run and/or execute the modules. The processor and modules of the processor can be configured to collectively execute the methods described herein, and/or to implements the apparatuses described herein.

In use, the aerosol preparation assembly 10 can produce an outlet aerosol having the desired particle size distribution to accommodate the methods of delivery and/or treatment described herein. For example, as discussed below, the delivery of aerosols via nasal cannulas over extended periods of time (e.g., greater than one half hour) can result in undesirable rainout and/or sputtering. Thus, in some embodiments, the aerosol preparation assembly 100 is matched to (configured to operate cooperatively with) the nasal cannula assembly 500. For example, in some embodiments, the nasal cannula assembly 500 can be configured such that a flow therethrough having a VMD of not greater than approximately 1.9 μm will result in minimal rainout and/or sputtering. Accordingly, in such embodiments, the aerosol preparation assembly 100 can be configured to receive an input aerosol $A_{IN}$ (see e.g., FIG. 2) and produce an outlet aerosol $A_{OUT}$ (see e.g., FIG. 2) having a VMD of not greater than approximately 1.9 μm. In this manner the aerosol delivery system 10 can effectively perform the methods described herein.

Moreover, in some embodiments, the particle size distribution of the delivered aerosol $A_{DEL}$ is controlled to minimize the amount of aerosol impaction in the nasal passages (i.e., the filtering of particles via the nose). Similarly stated, in some embodiments, the aerosol delivery system 10 (and any of the systems shown and described herein) is configured to produce the delivered aerosol $A_{DEL}$ having a desired particle size (e.g., VMD) to enable and/or accommodate the methods described herein. More particularly, it is known that the nose is an effective filter for particles that are greater than approximately 2-3 μm. Thus, transnasal delivery of aerosols having a VMD of, for example, 6 μm, will result in low rates of deposition into the lower airways. Accordingly, in addition to configuring the aerosol delivery system 10 to produce a flow of aerosol in which rainout and/or sputtering is minimized, in some embodiments, the delivery system 10 is also configured to produce an aerosol having a particle size within a predetermined range (e.g., 1.4 μm) to accommodate a particular method of treatment and/or to deliver a medicament having a particular composition.

Figure 2:
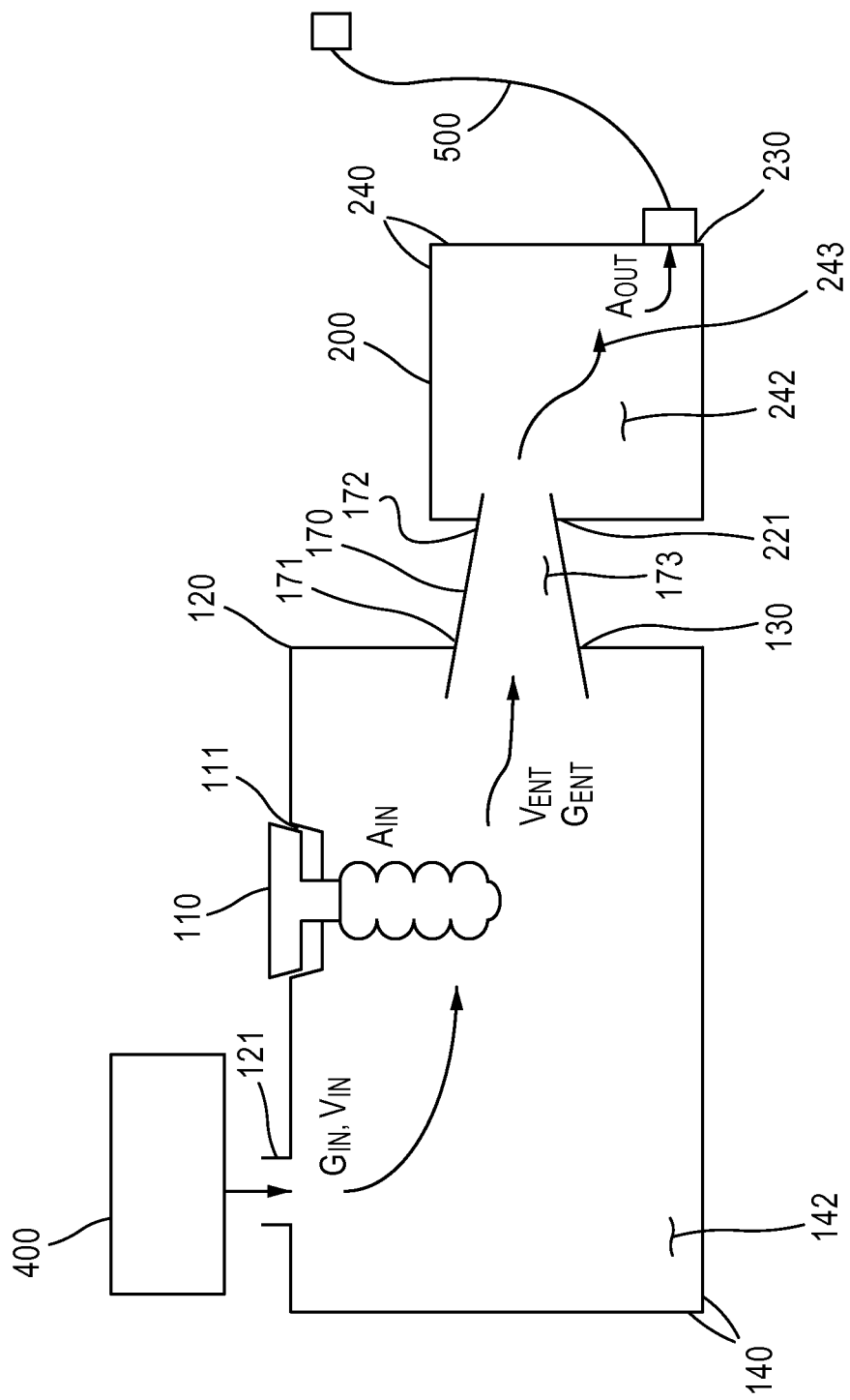
FIG. 2 is a schematic illustration of an aerosol preparation assembly, according to an embodiment.

In some embodiments, the aerosol preparation assembly 100 can be formed as illustrated in FIG. 2. As shown, the aerosol preparation assembly 100 includes an aerosol generator 110, an entrainment chamber 120, a nozzle 170, and a particle selection chamber 200.

The entrainment chamber 120 defines an entrainment volume 142 for generating entrained aerosol, as described in more detail herein. The entrainment chamber 120 also includes a gas inlet port 121, an aerosol inlet port 111, and an outlet port 130. The gas inlet port 121 is configured to fluidically couple the gas source 400 to the entrainment volume 142 defined by sidewalls 140. The entrainment chamber 120 is configured such that a velocity $V_{ENT}$ of a flow of a gas $G_{ENT}$ within the entrainment volume 142 is less than a velocity $V_{IN}$ of the flow of the gas $G_{IN}$ within the gas inlet port 121. The aerosol inlet port 111 is configured to receive an inlet aerosol $A_{IN}$ produced by the aerosol generator 110. The entrainment chamber 120 is configured such that at least a portion of the inlet aerosol $A_{IN}$ is entrained into the flow of the gas $G_{ENT}$ to produce an entrained aerosol $A_{ENT}$ at the outlet port 130.

As noted, in some embodiments, the entrainment chamber 120 can be designed and/or otherwise configured to produce a desired entrainment velocity $V_{ENT}$ within the entrainment volume 142 that promotes entrainment of the gas $G_{IN}$ by the aerosol $A_{IN}$. As discussed, the desired velocity $V_{ENT}$ is lower than the input velocity $V_{IN}$ at the gas inlet port 121. Without being bound by any particular theory or embodiment, it can generally be understood that lowering gas velocity over the same path length of interaction can increase contact time between the gas $G_{IN}$ and the aerosol $A_{IN}$ thereby increasing the probability, and hence the efficiency, of entrainment of the gas $G_{IN}$. Moreover, in some embodiments, one or more recirculation zones or regions (not shown) can be formed within the entrainment volume 142 that can be configured to permit the gas $G_{IN}$ and the aerosol $A_{IN}$ to cycle one or more times prior to exiting the entrainment chamber 120. In this manner, the path length of interaction can be increased, thereby increasing contact time between the gas $G_{IN}$ and the aerosol $A_{IN}$, thereby increasing the probability, and hence the efficiency, of entrainment of the gas $G_{IN}$.

Recirculation may be enhanced by any suitable mechanism and/or flow structure. In some embodiments, a recirculation zone can be produced by sudden expansion of the inlet gas $G_{IN}$ produced by the side walls 140 of the entrainment chamber 120 and/or the gas inlet port 121. In some embodiments, the gas inlet port 121 can be configured such that an expansion ratio of the gas $G_{IN}$ entering the entrainment volume 142 is greater than one. In other words, the volume of the gas $G_{IN}$ generally increases upon entering the entrainment volume 142, thereby resulting in lowered velocity. In some embodiments, the expansion ratio associated with the gas inlet port 121 is at least 1.1, at least 1.2, at least 1.3, at least 1.4, at least 1.5, at least 2, at least 2.5, at least 3, at least 3.5, at least 4, at least 4.5, at least 5, at least 6, at least 7, at least 8, at least 8, at least 10, and all values in between.

In some embodiments, the entrainment chamber 120 can further include a recirculation port (not shown) configured to receive a rained out portion of the entrained aerosol $A_{ENT}$ that is fluidically coupled to the aerosol generator 110 to recycle the rained out portion to the aerosol generator for reuse.

The aerosol generator 110 can be any suitable device and/or mechanism for aerosol generation as generally listed earlier, including, but not limited to, an aerosol spray (similar to commonly used aerosol cans), an atomic nozzle (such as those based on the Venturi effect), any type of nebulizer suitable for medicament delivery (mechanical, electrical, a current jet nebulizer, an ultrasonic nebulizer, a vibrating mesh nebulizer etc.), an electrospray, a vibrating orifice aerosol generator (VOAG), and/or the like. In some embodiments, the aerosol generator 110 generally includes a reservoir containing the liquid/gas of entrainment, a plurality of sidewalls defining an inlet opening, and optionally a surface associated with aerosol generation, such as a mesh. In some embodiments, the aerosol generator 110 can further be configured to received rained out portions of the aerosol (described further later) from the entrainment chamber 120 and the particle selection chamber 200 via a recycle port. In some embodiments, the aerosol generator 110 can have a cartridge in fluid communication therewith, where the cartridge contains a medicament from which the inlet aerosol $A_{IN}$ is produced by the aerosol generator 110, as described earlier.

The nozzle 170 is in fluidic communication with the outlet port 130 of the entrainment chamber 120, and is configured to provide a flow path for the entrained aerosol $A_{ENT}$ from the entrainment chamber 120 into the particle selection chamber 200, and to accelerate the entrained aerosol $A_{ENT}$. In some embodiments, the nozzle 170 can be removably coupled to the entrainment chamber 120 and/or the particle selection chamber 200. In other embodiments, the nozzle is monolithically constructed with at least one of the entrainment chamber 120 or the particle selection chamber 200. The nozzle 170 can generally include a first end portion 171 coupled to the entrainment chamber 120 to receive the entrained aerosol $A_{ENT}$, a second end portion coupled to the particle selection chamber 200 to deliver the entrained aerosol $A_{ENT}$, and a flow area 173 in between. In some embodiments, the second end portion can extend into the selection volume 242. The nozzle 170 can be of any suitable length and design for producing desired flow characteristics. In some embodiments, the first end portion 171 can have a larger opening (e.g. a relatively larger diameter) than an opening of the second end portion 172 (e.g. a relatively smaller diameter). Although described here as circular openings for the simplicity of explanation, it is understood that other shapes of these openings would also be suitable. In some embodiments, the diameter of the opening of the first end portion 171 and the diameter of the opening of the second end portion 172 are each independently selected from about 0.1 mm, about 0.5 mm, about 1 mm, about 1.5 mm, about 2 mm, about 2.5 mm, about 3 mm, about 3.5 mm about 4 mm, about 4.5 mm, about 5 mm, about 6 mm, about 7 mm, about 8 mm, about 9 mm about 10 mm, and all values in between.

The particle selection chamber 200 is configured for particle selection. More particularly, the particle selection chamber 200 and nozzle 170 are collectively configured such that a volumetric median diameter (VMD) of the outlet aerosol $A_{OUT}$ is less than a VMD of the inlet aerosol $A_{IN}$. In some embodiments, the entrainment chamber 120 and the particle selection chamber 200 can be monolithically constructed as a single unit, while in other embodiments, they can be separably coupled. In some embodiments, the particle selection chamber 200 can include a recirculation port (not shown) configured to receive a rained out portion of the entrained aerosol $A_{ENT}$ that is fluidically coupled to the aerosol generator 110 to recycle the rained out portion to the aerosol generator for reuse.

The particle selection chamber 200 includes a cannula coupling port 230 that is configured to be coupled to a nasal cannula, such as the nasal cannula assembly 500. The particle selection chamber 200 can be configured to receive the entrained aerosol $A_{ENT}$ from the nozzle 170 and produce an outlet aerosol flow $A_{OUT}$. The particle selection chamber includes an inlet port 221, a plurality of sidewalls 240 defining a selection volume 242, and a flow path 243 within the selection volume 242. The flow path 243 can be any straight or tortuous path that generates an output aerosol $A_{OUT}$ at the cannula coupling port 230 from the input aerosol $A_{IN}$ at the inlet port 221 that has desired characteristics of flow and composition.

The particle selection chamber 200 and nozzle 170 are collectively configured such that a VMD of the outlet aerosol $A_{OUT}$ is less than a volumetric median diameter of the inlet aerosol $A_{IN}$. In other words, the particle selection chamber 200 is configured to alter the diameter distribution of the inlet aerosol $A_{IN}$, by any suitable mechanism. In some embodiments, the particle selection chamber 200 is configured such that the VMD of the outlet aerosol $A_{OUT}$ is substantially independent of the VMD of the inlet aerosol $A_{IN}$. In other words, the flow path 243 can be designed such that no matter the characteristics of the inlet aerosol $A_{IN}$, the outlet aerosol $A_{OUT}$ always has the desired, relatively narrower particle size characteristics (e.g., VMD). For example, in some embodiments, the VMD of the inlet aerosol $A_{IN}$ is about 3 microns, is about 4 microns, is about 5 microns, is about 6 microns, is about 7 microns, is about 8 microns, is about 9 microns, is about 10 microns, and all values in between; and the VMD of the outlet aerosol $A_{OUT}$ is about 0.5 microns, is about 1 micron, is about 1.1 microns, is about 1.2 microns, is about 1.3 microns, is about 1.4 microns, is about 1.5 microns, is about 1.6 microns, is about 1.7 microns, is about 1.8 microns, is about 1.9 microns, is about 2 microns, is about 2.5 microns, and all values in between.

Hence, in some embodiments, the flow path 243 includes one or more mechanisms that affect and/or adjust the particle size diameter distribution of the inlet aerosol $A_{IN}$. In some embodiments, the flow path 243 can include an obstructive structure that alters a path of inertial flow of the inlet aerosol $A_{IN}$. Larger particles will have a greater tendency to be stopped by the obstructive structure due to inertia than the smaller particles, which in turn will have a greater tendency to flow around the inertial structure. For example, the obstructive structure can be a baffle, and the nozzle 170 and the baffle can be configured such that a portion of the inlet aerosol $A_{IN}$ comprising larger particles tends to impinge on the baffle, while another portion of the inlet aerosol $A_{IN}$ comprising smaller particles tends to flow around the baffle.

In some embodiments, the cannula coupling port 230 includes a cannula opening, a cannula nozzle and a coupling portion. The cannula nozzle can include an inner wall having a flow path that defines an effective flow area which is substantially the same as an effective flow area of a flow path defined by an inner wall of the nasal cannula of the patient. The coupling portion can be configured to be coupled to the nasal cannula such that the inner wall of the cannula nozzle and the inner wall of the nasal cannula form a substantially continuous surface. In this manner, the interface between the nasal cannula and the cannula coupling port 230 can be substantially free of flow obstructions, expansions and/or contractions, all of which can lead to rainout.

The gas source 400 and the nasal cannula assembly 500 are similar to the gas source and nasal cannula as characterized earlier. In some embodiments, the gas source 400 can be configured to produce the flow of a gas within the entrainment volume 142 having a periodic variation in flow rate.

In use, the aerosol preparation assembly of FIG. 2 is configurable for two stage operation to produce the desired particle size range: first at the entrainment chamber 120, and then at the particle selection chamber 200. In some embodiments, the entrainment chamber 120 can provide a substantially linear, unobstructed flow path 143 for inlet gas $G_{IN}$ and inlet aerosol $A_{IN}$ to generate an entrained aerosol $A_{ENT}$ having desired characteristics for subsequent particle selection. This can be accomplished by reducing gas velocity $V_{IN}$ to promote entrainment, and then increasing it again, by virtue of the design of the nozzle 170, to convey the inlet aerosol $A_{IN}$ to the particle selection chamber 200 having a velocity $V_{IN}$ effective to cause particle selection/rejection when the inlet aerosol $A_{IN}$ impinges on an obstructive chamber in a flow path 243. The velocity $V_{IN}$, as well as the design of the flow path 243 can then be 'tuned' to achieve the desire particle selection. The outlet aerosol $A_{OUT}$ from the cannula coupling port 230 can be delivered to the cannula of the patient in a reproducible manner since, by virtue of the inner wall of the cannula nozzle and the inner wall of the nasal cannula forming a substantially continuous surface, the desirable characteristics of the outlet aerosol can be conserved while the outlet aerosol $A_{OUT}$ traverses the nasal cannula assembly 500.

Figure 3:
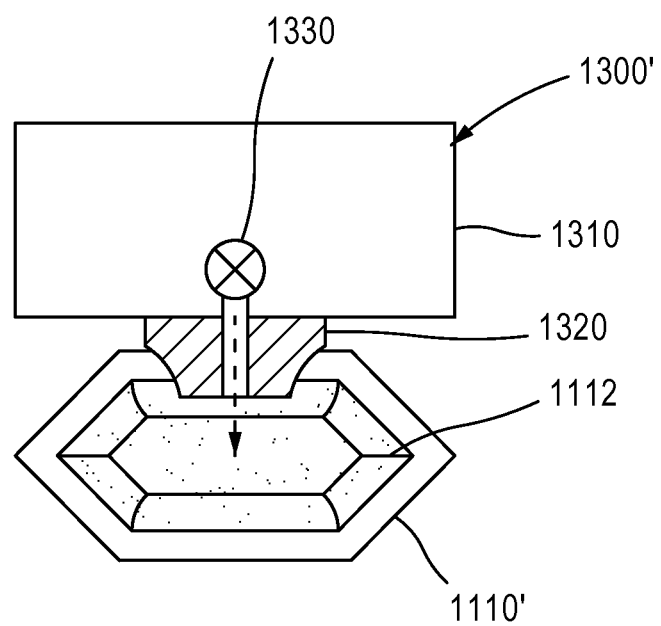
FIG. 3 is a schematic illustration of a medicament container, according to an embodiment.

In some embodiments, a medicament cartridge 1300' can be formed as illustrated in FIG. 3, and can, in some respects, be similar to the medicament cartridge 1300. The medicament cartridge 1300' includes a medicament container 1310 containing a liquid medicament. The medicament cartridge 1300' includes an interface member 1320 coupled to the medicament container 1310 for access to the medicament, and also configured to be removably coupled to an inlet opening 1118 defined by an aerosol generator 1110', which can be similar to the generator 110 of FIG. 2. In some embodiments, the interface member 1320 can be constructed from a deformable material (e.g., soft plastic) configured to form a substantially fluid-tight seal with the aerosol generator when coupled to the aerosol generator. In some embodiments, the medicament cartridge 1300' can be formed in the proximity of a recirculation port (not shown here, as described in more detail in FIG. 5), and the interface member 1320 can be any conduit connecting the medicament cartridge 1300' to the aerosol generator 1110'. For example, although shown as being located above the aerosol generator such that gravity can assist the flow from the cartridge into the aerosol generator, in other embodiments, the cartridge can be disposed beside (i.e., at substantially the same height) or even below the aerosol generator. In some embodiments, the aerosol generator 1110' can be a nebulizer.

The medicament cartridge 1300' also includes a valve 1330 defining a liquid flow path from the medicament container 1310 to the reservoir 1112 of the aerosol generator 1110'. More particularly, the valve 1330 can limit and/or control the flow of the medicament from the medicament container 1310 into the reservoir 1112. In this manner, the medicament can be conveyed into the aerosol generator 1110' at a rate that corresponds to the rate of delivery of the aerosol (e.g., $A_{OUT}$ or $A_{DEL}$) as described herein. The valve 1330 can include any mechanism for controlling the flow. For example, in some embodiments, the valve 1330 can define a gas flow path from the reservoir 1112 of the aerosol generator 1110' to limit flow of the liquid medicament from the medicament container 1310 into the reservoir of the aerosol generator. In some embodiments, the valve 1330 can be configured to limit a static pressure exerted by the liquid medicament within the medicament container 1310 on a surface of the aerosol generator (e.g., a bottom surface, mesh or the like). As discussed earlier, the medicament cartridge 1300', and particularly the operation of the valve 1330, can be under control of a system controller, such as the controller 1600.

In some embodiments, a filter can be disposed within the valve 1330 and/or between the valve 1330 and the reservoir 1112 of the aerosol generator.

Figure 4:
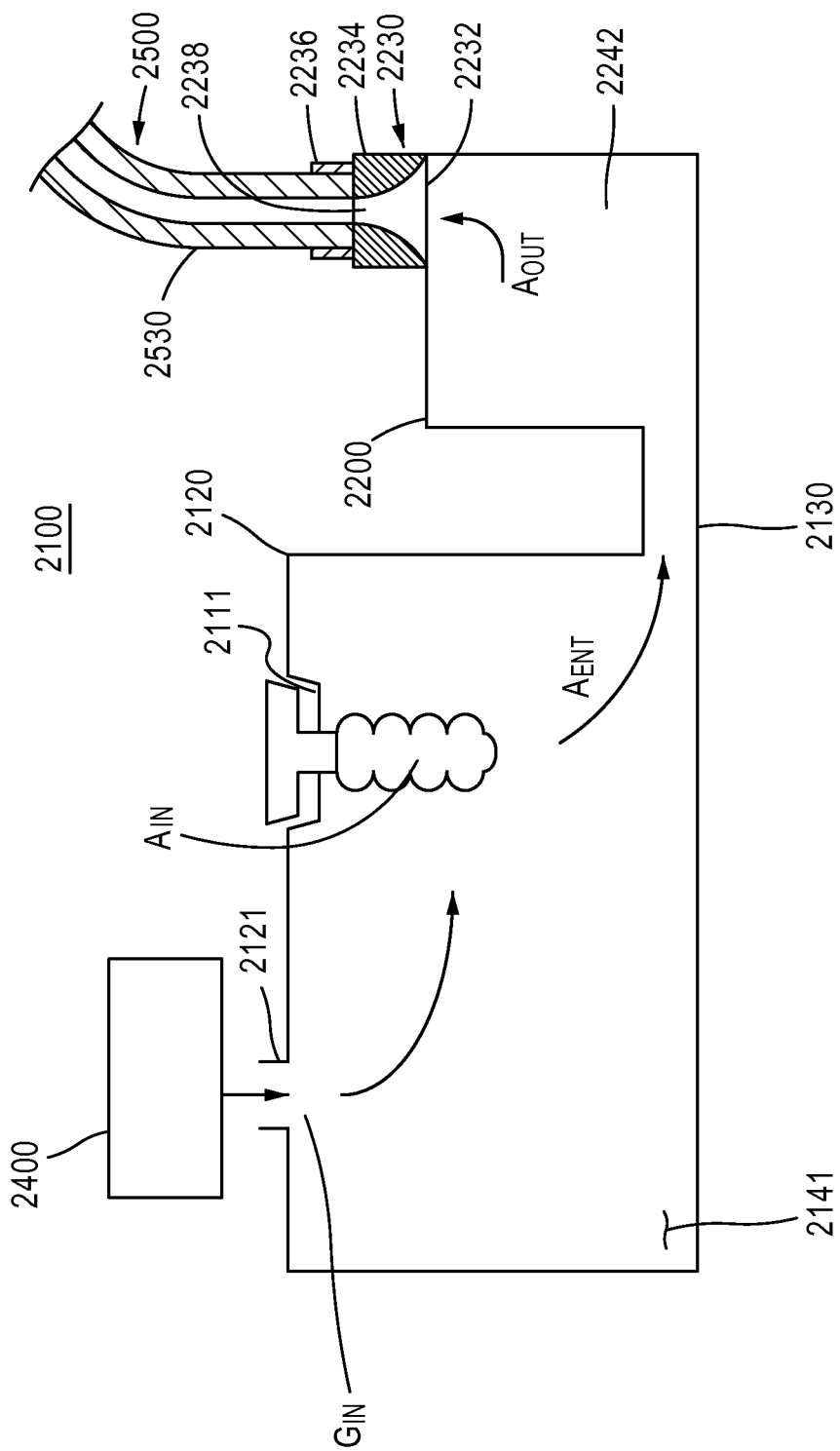
FIG. 4 is a schematic illustration of an aerosol preparation assembly, according to another embodiment.

In some embodiments, an aerosol preparation assembly 2100 can be formed as illustrated in FIG. 4. It is understood that unless explicitly stated otherwise, components of the aerosol preparation assembly 2100 can be similar to, and/or operate in a manner similar to, similarly named components of the aerosol preparation assembly 1100. The aerosol preparation assembly 2100 includes an entrainment chamber 2120, a particle selection chamber 2200, and a nasal cannula assembly 2500.

The entrainment chamber 2120 can be similar to the entrainment chamber 1120, and defines an entrainment volume 2141. The entrainment chamber 2120 includes a gas inlet port 2121, an aerosol inlet port 2111, and an outlet port 2130. The gas inlet port 2121 can be configured to fluidically couple the gas source 2400 to the entrainment volume 2141. The aerosol inlet port 2111 can be configured to receive an inlet aerosol $A_{IN}$ produced by the aerosol generator 2110. The entrainment chamber 2120 can be configured such that at least a portion of the inlet aerosol $A_{IN}$ is entrained into a flow of a gas $G_{IN}$ within the entrainment volume 2141 to produce an entrained aerosol flow $A_{ENT}$ at the outlet port 2130. In some embodiments, the entrainment chamber 2120 can include a recirculation port configured to receive a rained out portion of the entrained aerosol $A_{ENT}$ that is fluidically coupled to the aerosol generator 2110 to recycle the rained out portion to the aerosol generator for reuse.

The particle selection chamber 2200 includes a cannula coupling port 2230 configured to be coupled to a nasal cannula 2500 of the patient. The particle selection chamber 2200 can be configured to receive the entrained aerosol $A_{ENT}$ from the outlet port 2130 of the entrainment chamber 2120 and produce an outlet aerosol $A_{OUT}$. The particle selection chamber 2200 can be further configured to extract a portion of the entrained aerosol $A_{ENT}$ such that a VMD of the outlet aerosol $A_{OUT}$ is less than a VMD of the inlet aerosol $A_{IN}$. Accordingly, in some embodiments, the particle selection chamber 2200 can include an obstructive structure such as a baffle, where a portion of the entrained aerosol $A_{ENT}$ impinges on the baffle, as described earlier. In some embodiments, the particle selection chamber 2120 can include a recirculation port configured to receive a rained out portion of the entrained aerosol $A_{ENT}$ that is fluidically coupled to the aerosol generator 2110 to recycle the rained out portion to the aerosol generator for reuse.

In some embodiments, the entrainment chamber 2120 and the particle selection chamber 2200 can be connected via a nozzle (not shown) as described earlier, although this is not necessary to achieve the benefits stated herein.

As illustrated in FIG. 4, the cannula coupling port 2230 defines an opening 2232 that is continuous with the selection volume 2242, and that can receive the outlet aerosol $A_{OUT}$ for delivery to the cannula assembly 2500. The cannula coupling port 2230 also includes a cannula nozzle 2234 configured to modify characteristics of the outlet aerosol $A_{OUT}$ for delivery to the patient. For example, as illustrated, the cannula nozzle 2234 can serve to decrease the cross section of the flow of the outlet aerosol $A_{OUT}$, thereby increasing the velocity of the outlet aerosol $A_{OUT}$ to a level sufficient to propel it through the nasal cannula assembly 2500. In this manner, rainout due to sedimentation within the nasal cannula assembly 2500 can be minimized. The cannula coupling port 2230 also includes a coupling portion 2236 that receives the supply tube 2530 of the nasal cannula assembly 2500. The coupling portion 2236 is configured to be coupled to the nasal cannula assembly 2500 such that an inner wall of the cannula nozzle and an inner wall of the nasal cannula form a substantially continuous surface 2238. Employing the smooth surface 2238 maintains the flow profile of the outlet aerosol $A_{OUT}$, thereby preventing inadvertent changes in flow velocity, sudden expansions, flow impediments and the like, thereby minimizing rainout at the transition into the cannula assembly 2500. In some embodiments, the cannula coupling port 2230 can be magnetically coupled to the nasal cannula assembly 2500; in other words, magnets can be present in each of the cannula coupling port 2230 (e.g. in the coupling portion 2236) and the cannula assembly 2500 (e.g. at an end of the supply tube 2530), such that in a mating position, attraction between one set of opposing poles of the magnets can aid, guide, lock, align, and/or otherwise effect the coupling of the nasal cannula assembly 2500 into the cannula coupling port 2230 to yield the continuous surface 2238.

Aspects of this design hence overcome shortcomings in the prior art that employ other coupling means providing discontinuities at the final entry point for aerosolized medicament into a nasal cannula delivery assembly. For example, the use of barbed fittings in the prior art was observed to cause sudden expansion of the flow profile of the outlet aerosol $A_{OUT}$.

Figure 5:
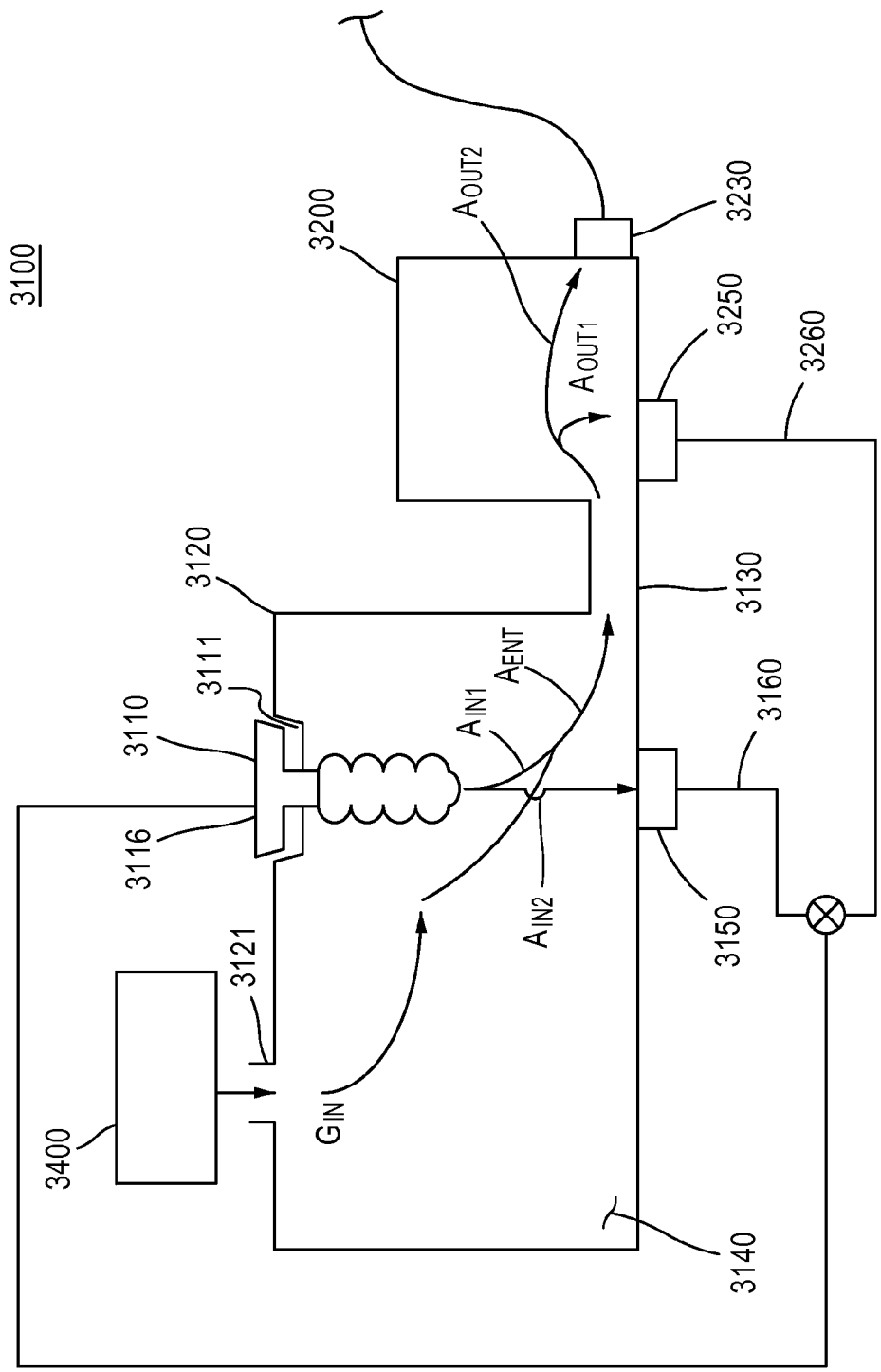
FIG. 5 is a schematic illustration of an aerosol preparation assembly, according to yet another embodiment.

In some embodiments, an aerosol preparation assembly 3100 can be formed as illustrated in FIG. 5. It is understood that unless explicitly stated otherwise, components of the aerosol preparation assembly 3100 can be similar to, and/or operate in a manner similar to, similarly named components of the aerosol preparation assembly 1100 and/or the aerosol preparation assembly 2100. The aerosol preparation assembly 3100 includes an entrainment chamber 3120 and a particle selection chamber 3200.

The entrainment chamber 3120 can define an entrainment volume 3140 by virtue of the sidewalls from which the entrainment chamber 3120 is constructed. The entrainment chamber 3120 can include a gas inlet port 3121, an aerosol inlet port 3111, an outlet port 3130 and a first recirculation port 3150. The gas inlet port 3121 is configured to fluidically couple the gas source 3400 to the entrainment volume 3140. The aerosol inlet port 3111 is configured to receive an inlet aerosol $A_{IN}$ produced by the aerosol generator 3110 for entrainment by the gas $G_{IN}$ to generate entrained aerosol $A_{ENT}$.

Aspects of some embodiments can account for the possibility that some rain out and initial particle selection in the entrainment chamber 3120 (e.g., due to sedimentation) will occur. In other words, the entirety of the inlet aerosol $A_{IN}$ may not be consumed to generate $A_{ENT}$, and some will be rained out and/or precipitated. When the aerosol contains medicament, such waste can be expensive, and is undesirable. Accordingly, the entrainment chamber 3120 is configured such that a first portion of the inlet aerosol $A_{IN1}$ is entrained into the flow of a gas $G_{IN}$ within the entrainment volume 3140 to produce the entrained aerosol $A_{ENT}$ at the outlet port 3130, and a second portion of the inlet aerosol $A_{IN2}$, such as may not be consumed to generate the entrained aerosol $A_{ENT}$, is collected within the entrainment chamber 3120. In some embodiments, the collection of the second portion $A_{IN2}$ is precipitated and/or removed from the aerosol via sedimentation, i.e., is gravity driven.

A first recirculation port 3150 is configured to receive and/or otherwise collect the second portion $A_{IN2}$. The first recirculation port 3150 can be designed for optimal collection of the second portion $A_{IN2}$. The first recirculation port 3150 is fluidically coupled to the aerosol generator 3110 via a first recirculation pathway 3160. In some embodiments, the first recirculation port 3150 may be coupled to the first recirculation pathway 3160 in a manner similar to how (see FIG. 4) the cannula coupling port 2230 is coupled to the assembly 2500. In other words, a substantially smooth and continuous surface may be formed that prevents backflow or otherwise retards the collection of the second portion $A_{IN2}$.

The particle selection chamber 3200 includes a cannula coupling port 3230 configured to be coupled to a nasal cannula of the patient, and can be similar to the cannula couple port 2230 in FIG. 4. The particle selection chamber 3200 is configured to receive the entrained aerosol $A_{ENT}$ from the outlet port 3130 of the entrainment chamber 3120 and produce an outlet aerosol $A_{OUT1}$ to be transmitted to the nasal cannula of the patient.

As discussed earlier, particle selection, such as by using an obstructive structure, necessarily results in particle rejection and/or removal from the aerosol and/or flow through the particle selection chamber 3200. When the particles contain medicament, outright disposal of the portion that is rejected is wasteful, and aspects of some embodiments are operable to recover the disposed portions for recycling and aerosolization. Accordingly, the particle selection chamber 3200 is configured to extract a portion of the entrained aerosol $A_{OUT2}$ from the entrained aerosol $A_{ENT}$ such that a VMD of the outlet aerosol $A_{OUT1}$ is less than a VMD of the inlet aerosol $A_{IN}$. A second recirculation port 3250 can be configured to receive the extracted portion $A_{OUT2}$. The second recirculation port 3250 is fluidically coupled to the aerosol generator 3110 via a second recirculation pathway 3260. In some embodiments, the second recirculation port 3250 may be coupled to the second recirculation pathway 3260 in a manner similar to how the cannula coupling port 2230 is coupled to the assembly 2500 (see e.g., FIG. 4). In other words, a substantially smooth and continuous surface may be formed that prevents backflow or otherwise retards the collection of the second portion $A_{OUT2}$.

As illustrated in FIG. 5, the first circulation pathway 3160 and the second circulation pathway 3260 can be recombined prior to being coupled to the aerosol generator 3110 via a single return port 3116. However, it is understood that the first circulation pathway 3160 and the second circulation pathway 3260 can be independently provided to the aerosol generator 3110 via separate ports (not shown). In some embodiments, as described earlier for FIG. 3, the first recirculation port 3150 and/or the second circulation pathway 3260 can drain directly into a medicament cartridge of the types shown and described herein. In some embodiments, at least one of the first circulation pathway 3160 and the second circulation pathway 3260 lies outside and/or otherwise excludes the entrainment chamber 3120, for each of manipulation. For example, at least one of the first circulation pathway 3160 and the second circulation pathway 3260 can include valves operably manually and/or by the controller 1600 to continuously or periodically remove the $A_{IN2}$ and $A_{OUT2}$ streams.

Further, aspects of some embodiments are operable to perform one or more operations on the $A_{IN2}$ and/or $A_{OUT2}$ streams prior to reintroduction into the aerosol generator 3110. For example, liquid and/or medicament may be added to modify the concentration of the recycled stream(s) to match or be within a tolerance of the contents of the reservoir of the aerosol generator 3110. In some embodiments, the circulation pathway(s) can include one or more filters for removing any process contaminants that can be drained off. In some embodiments, a parameter associated with the reintroduced stream(s) can be monitored, such as level of medicament, etc.

Figure 6:
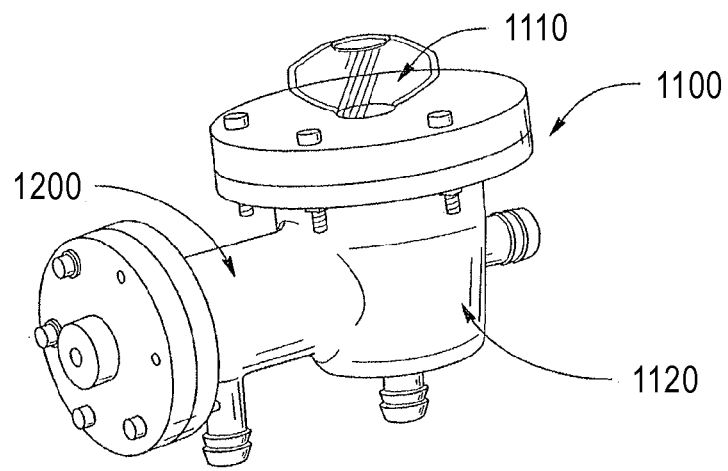
FIG. 6 is a perspective view of an aerosol delivery system including an aerosol preparation assembly, according to some embodiments.
Figure 7:
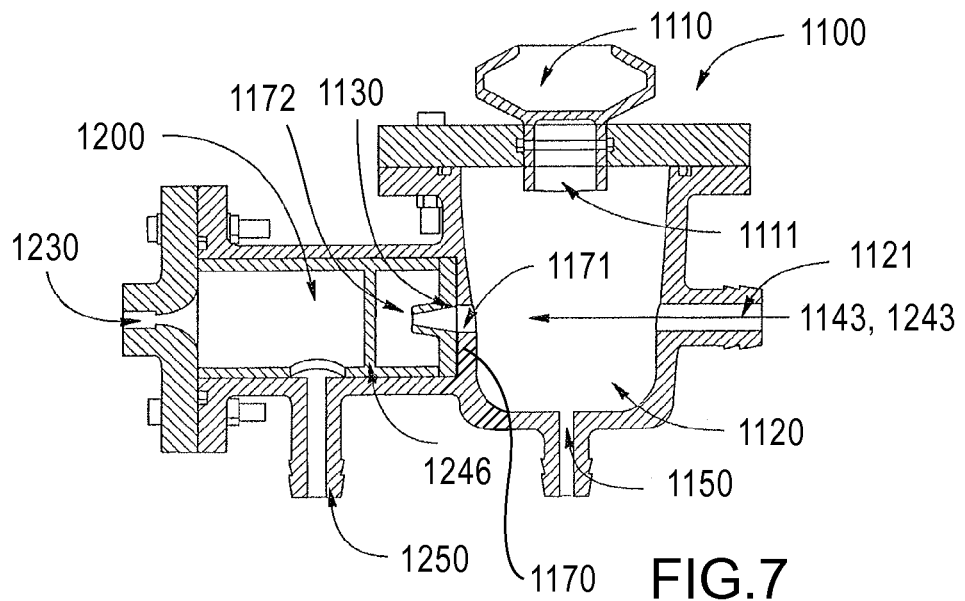
FIGS. 7-8 are cross-sectional side views of the aerosol delivery system of FIG. 6.
Figure 8:
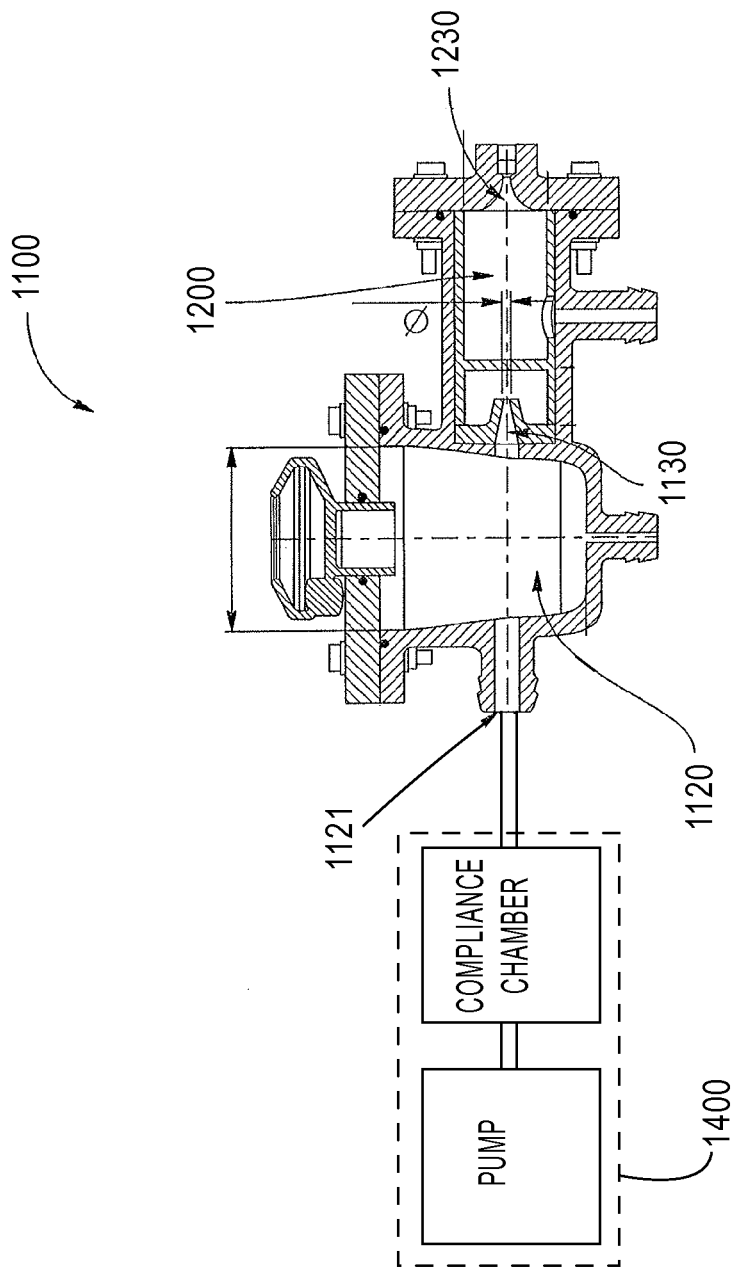

FIGS. 6-8 show an aerosol preparation assembly 1100, according to an embodiment. The aerosol preparation assembly 1100 can be coupled to a gas source 1400 of pulsatile or non-pulsatile gas flow, and a nasal cannula (not shown) as a part of an overall aerosol delivery system of the types shown and described herein. The aerosol preparation assembly 1100 includes an entrainment chamber 1120 and a particle selection chamber 1200. The entrainment chamber 1120 includes an aerosol generator 1110, an aerosol inlet port 1111, an entrainment fluid inlet port 1121, an entrainment fluid outlet 1130, and a rainout collection outlet or drain 1150. The entrainment fluid outlet 1130 includes a first end 1171 and a second end 1172. The entrainment chamber 1120 defines a fluid pathway 1143, which is generally formed by any suitable structure that directs the flow of fluid through the entrainment chamber 1120.

The particle selection chamber 1200 includes an impaction baffle 1246, a particle selection chamber outlet 1230 and a rainout collection outlet or drain 1250. The drain 1250 can be suitably formed anywhere in the particle selection chamber 1200, including before or after (i.e., upstream or downstream of) the baffle 1246. The particle selection chamber 1200 defines a fluid pathway 1243, which is generally formed by any suitable structure that directs the flow of fluid through the particle selection chamber 1200. The outlet 1230 may be connected to a cannula (not shown), such as a nasal cannula for delivering aerosol to a subject. As shown in FIG. 8, the aerosol preparation assembly 1100 may be connected to a gas source 1400 including a pump and an optional compliance chamber.

Figure 9:
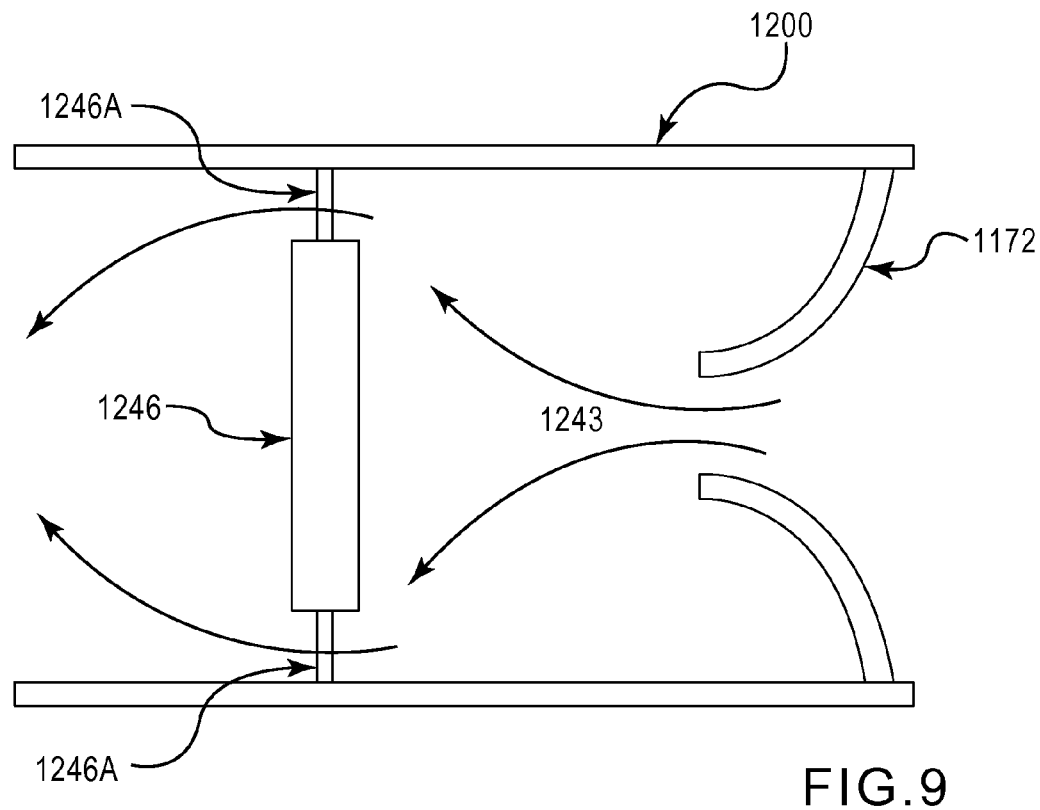
FIG. 9 is a cross-sectional side schematic illustration of an impaction baffle in a particle selection chamber of the aerosol delivery system of FIG. 6.
Figure 10:
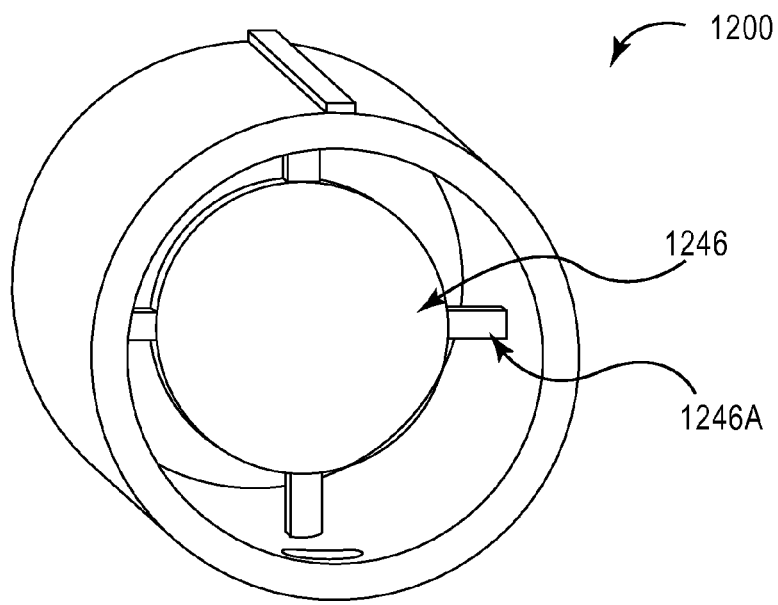
FIG. 10 is a perspective partially cut-away view of the impaction baffle of FIG. 9.

The aerosol generator 1110 can be any suitable nebulizer unit, such as a jet nebulizer, ultrasonic nebulizer or vibrating mesh nebulizer that is configured to provide an aerosol into the entrainment chamber 1120. Commercially available nebulizers suitable for inclusion in the entrainment chamber 1120 include vibrating mesh nebulizers from Aerogen Aeroneb Lab, Pro and Solo, Pari eFlow vibrating mesh technologies, Omron's vibrating horn technologies, vibrating mesh or ultrasonic technologies from Philips, ActivAero and other manufacturers. The inlet port 1121 may be connected to a gas source 1400, such as an air or other gas source for providing an entrainment gas that flows into the entrainment chamber 1120 and through the particle selection chamber 1200 generally along the fluid pathways 1143, 1243. The entrainment gas moves generally along the fluid pathways 1143, 1243 and carries the aerosol from the aerosol generator 1110 through the port 1130, around the baffle 1246 and out of the selection chamber outlet port 1230. As shown in FIGS. 9-10, the baffle 1246 is held in position by supports 1246A.

In some embodiments, the gas source 1400 includes a pump that produces a gas flow entraining the aerosol that is characterized by a non-pulsatile and/or substantially steady-state flow. The source of such a non-pulsatile flow pulsatile flow can be any suitable pump, such as a diaphragm pump, a peristaltic pump or a rotary vane pump. The pump is disposed upstream of an entrainment chamber, thereby producing a positive pressure through the aerosol preparation assembly 1100. In some embodiments, the gas source 1400 can include a compliance chamber (see e.g., FIG. 8) to produce an air source to the inlet 1121 that has a reduced amount of pressure or flow oscillations from the pump of the gas source 1400. The compliance chamber may be a chamber of a size sufficient to reduce any flow oscillations from the pump. The optional compliance chamber may be used to provide reproducible flows of aerosol of a given particle size with adequate emitted volumes. In other embodiments, the source of gas can be a compressed gas container. For example, in such embodiments, the entrainment fluid can be dehumidified and/or dried compressed air, and/or oxygen (including low humidity oxygen, high humidity oxygen, or oxygen where the humidity levels are not controlled or manipulated). In some embodiments, the source of gas is not temperature-controlled.

In use, the aerosol generated by the generator 1110 may produce particles of a wide range of particle sizes. When the entrainment gas carries the aerosol though the port 1130, the velocity of the gas increases because the first end 1171 of the outlet 1130 has a cross-sectional area that is larger than the cross-sectional area of the second end 1172. Such narrowing produces a nozzle or a jet, which accelerates the movement of the aerosol particles towards the baffle. The diameter $\phi$ of the second end 1172 can be tuned and/or selected to achieve a desired velocity of aerosol particles, and can consequently increase or decrease the impaction of the aerosol particles on the baffle. The entrainment gas and aerosol is therefore directed toward the baffle 1246 with an increased velocity as compared to the velocity of the flow through the entrainment chamber 1120. For outlet flow rates between 0.5 and 5 L/min, the nozzle diameter $\phi$ is preferably between 0.5 to 5 mm in diameter. Nozzle diameters that are too small may prevent efficient cleaning of the device, and nozzle diameters that are too large may require too high an airflow for effective particle acceleration and/or selection.

As shown in FIGS. 6-8, the nozzle 1170 can be separately constructed from and later assembled into the entrainment chamber 1120 and/or the particle selection chamber 1200. This arrangement can allow an aerosol preparation assembly (e.g., the aerosol preparation assembly 1100) to be equipped with multiple different nozzles (e.g., having different sizes and/or performance characteristics) to allow the system to be tuned and/or optimized to achieve a desired output. Similarly stated, in some embodiments, a kit can include an aerosol preparation assembly and a set of nozzles, wherein each nozzle has a different size. In other embodiments, however, the nozzle can be monolithically constructed with the entrainment chamber 1120 and/or the particle selection chamber 1200.

The baffle 1246 is sized and configured in cooperation with the nozzle 1170 such that larger aerosol particles will generally not be able to pass around the baffle 1246 when the entrainment gas and aerosol flows into the particle selection chamber 1200. Accordingly, smaller aerosol particles may pass around the baffle 1246 such that the resulting aerosol particles that pass out of the outlet 1230 and into a nasal cannula are generally smaller than the aerosol particles in the entrainment chamber 1120. Although the baffle 1246 is shown as being circular and/or disc-shaped, in other embodiments, baffles can be spherical, triangular, rectangular, pentagonal, hexagonal, 6+n-gonal where n≥1. The baffle 1246 can be mounted in cruciform or other suitable fashion. As described in more detail below, modifications to the nozzle diameter, flow rate and baffle dimensions may be interrelated and can each contribute to the resulting aerosol and particle size distribution produced.

In some embodiments, the volumetric median diameter (VMD) of the aerosol particles exiting the particle selection chamber (e.g., the outlet aerosol) is between 1 and 4 μm, and the percentage of the particles above 4 μm is less than 5%, less than 2% or less than 1% of the total particle volume emitted from the particle selection chamber 1200 into the cannula. The flow rate entering the inlet 1121 may be between 0.5 L/min to 5 L/min, and more preferably between 1 and 3 L/min.

In some embodiments, the aerosol preparation assembly 1100 can be configured to produce an outlet aerosol having the desired particle size distribution to accommodate the methods of delivery and/or treatment described herein. For example, as discussed below, the delivery of aerosols via nasal cannulas over extended periods of time (e.g., greater than one half hour) can result in undesirable rainout and/or sputtering. Thus, in some embodiments, a delivery system (e.g., the aerosol delivery system 10 shown and described with respect to FIG. 1) includes an aerosol preparation assembly (e.g., the assembly 1100) that is matched to the nasal cannula included with the aerosol delivery system. For example, in some embodiments, a nasal cannula can be configured such that a flow therethrough having a VMD of not greater than approximately 1.9 μm will result in minimal rainout and/or sputtering. Accordingly, in such embodiments, an aerosol preparation assembly (such as the aerosol preparation assembly 1100) can be configured to receive an input aerosol and produce an outlet aerosol having the desired particle size distribution to accommodate delivery via a nasal cannula.

Moreover, the aerosol preparation assemblies described herein (e.g., the assembly 1100 can be configured to produce an aerosol having a particle size within a predetermined range (e.g., VMD of 1.4 μm) to accommodate a particular method of treatment and/or to deliver a medicament having a particular composition. As described herein, certain compositions (e.g., 7% hypertonic saline) are formulated to be transnasally delivered in an aerosol form having a predetermined particle size and/or particle size distribution to accommodate high deposition efficiency in a particular region of the airway. Accordingly, in some embodiments, the aerosol preparation assembly 1100 can be configured to reduce the volumetric median diameter (VMD) of the inlet aerosol (i.e., the aerosol out of the nebulizer 1110) from about 6 μm to less than about 2 μm as the aerosol exits the particle selection chamber outlet 1230 and into, for example, a nasal cannula. Similarly stated, the percentage of particles larger than 3 to 4 μm may be decreased and/or removed by the entrainment chamber 1120 and/or the particle selection chamber 1200.

Figure 11:
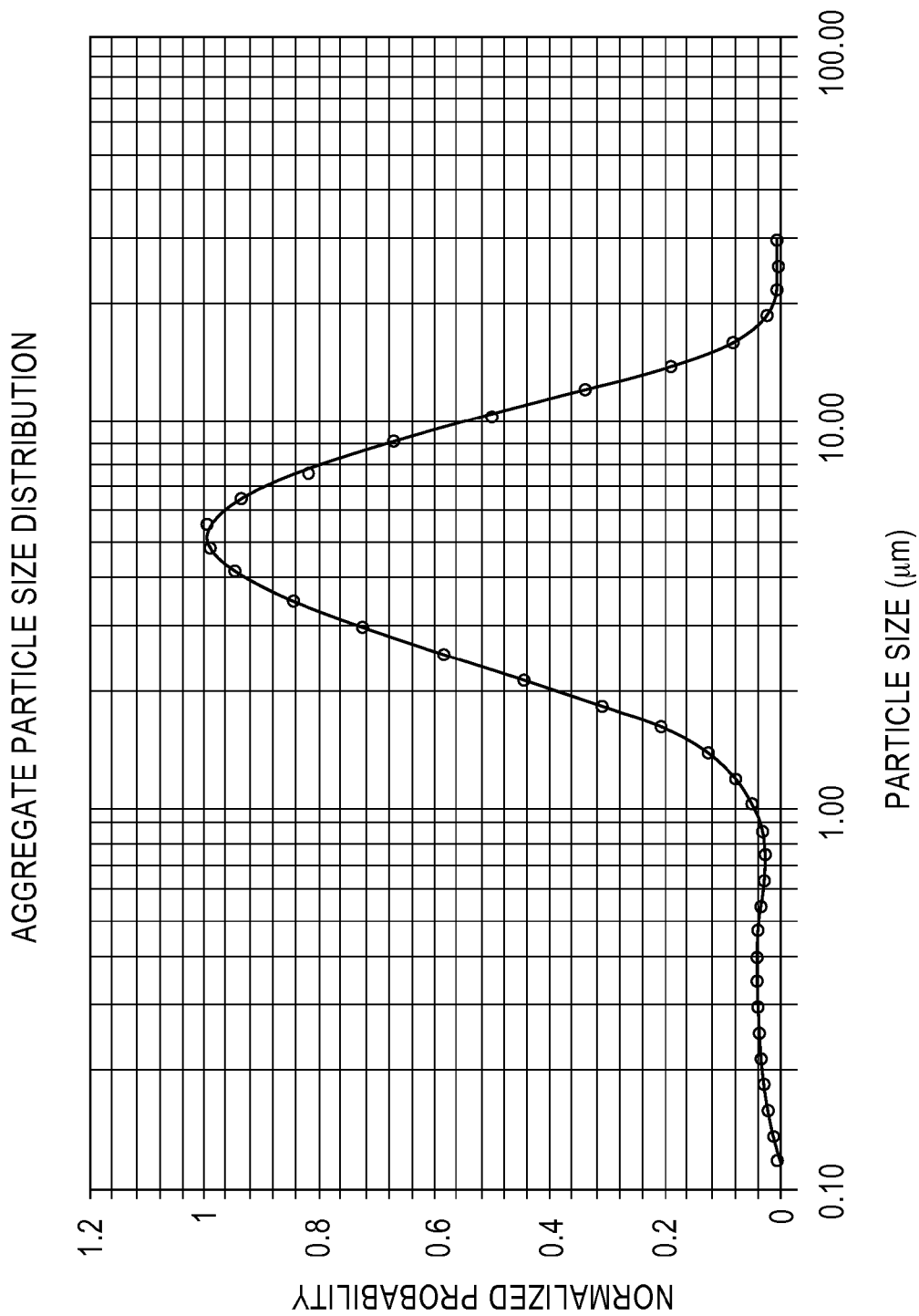
FIGS. 11-13 display representative particle size distributions measured by a laser diffraction instrument (Spraytech) for an Aerogen Aeroneb™ Lab nebulizer with 7% hypertonic saline solution.
Figure 12:
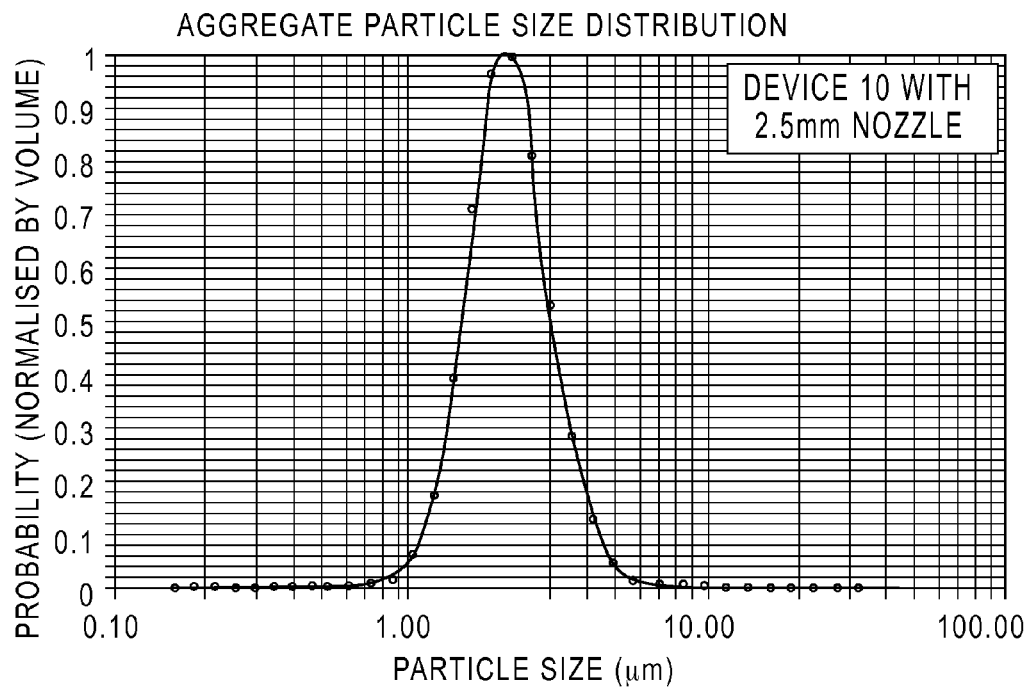
Figure 13:
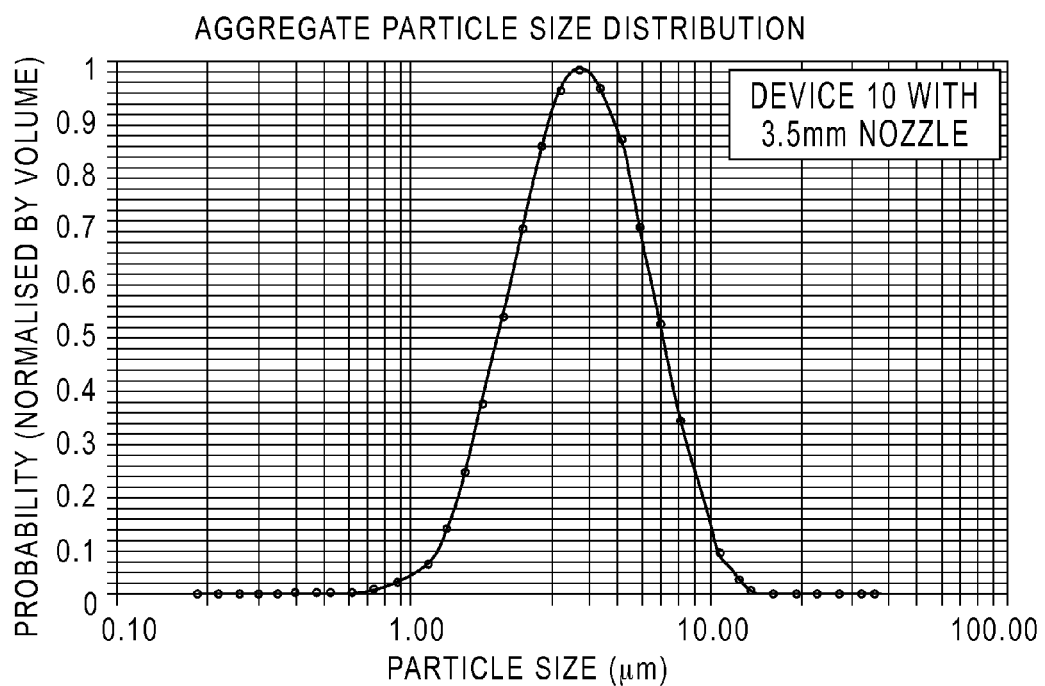

FIGS. 11-13 show the particle size distribution comparing an inlet aerosol (e.g., $A_{IN}$) to the aerosol output (e.g., $A_{OUT}$) from the aerosol preparation assembly 1100. The data presented in FIGS. 11-13 is a representative particle size distribution measured by laser diffraction instrument (Spraytec, Malvern Instruments Ltd) for the aerosol preparation assembly 1100, in which the aerosol generator 1110 is an Aerogen Aeroneb™ nebulizer (the Aeroneb™ Lab nebulizer was utilized to generate the nebulizer-only data shown in FIG. 11, and the Aeroneb™ Pro nebulizer was utilized to generate the data shown in FIGS. 12 and 13). The tests were conducted using 7% hypertonic saline solution, and for those data presented for the aerosol preparation assembly 1100, at a flow rate of two L/min. The entrainment air was maintained at approximately 20° C. and 50% relative humidity.

As shown in FIG. 11, the volumetric mean diameter (VMD) of aerosol produced by the nebulizer only (e.g., the inlet aerosol $A_{IN}$) was 4.2 μm. Such an aerosol has a large percentage of volume-normalized particles exceeding 3 to 4 μm. An aerosol of such particle size distribution may be difficult to convey via a nasal cannula because the larger particles are likely to impact, and/or gravitationally sediment during the course of the travel through the length of the nasal cannula. The resulting rainout may cause discomfort to the patient when such rainout liquid droplets reach the exit points of the nasal cannula and are potentially inhaled by the patient (i.e., sputtering). Moreover, as discussed herein, an aerosol having a particle size (e.g., VMD) greater than the range of 2-3 μm is not a good candidate for transnasal delivery, due to the impaction/loss within the nasal passages.

The data shown in FIG. 12 was produced using the aerosol preparation assembly 1100, as shown in FIG. 8. As discussed herein, the particle selection chamber 1200 allowed for control of the particle sizes exiting the outlet 1230 and consequently entering the nasal cannula. Some of the factors that may allow for tuning or controlling the particle size selection are the overall flow rate and the diameter of the inertial impactor nozzle 1170. For this test, the particle selection chamber 1200 was equipped with a nozzle having a diameter φ of 2.5 mm, and the gas source was coupled to a compliance chamber providing non-oscillating output of 2 L/min, 7% (w/v) NaCl solution, ~20° C. and 50% relative humidity. As shown in FIG. 12, under such conditions, the particle selection chamber 1200 produced a particle size distribution having a VMD of 1.9 μm and minimal percentage of the particles larger than 4 μm. As shown in FIG. 14, under the same conditions, the device 10 according to an embodiment equipped with 3.5 mm nozzle generated aerosol with VMD of 3.1 μm and a larger percentage of particles above 4 μm. Accordingly, the particle selection chamber 1200 can be tuned, optimized and/or configured to produce a desired particle size distribution and/or VMD that corresponds to a particular medicament (e.g., osmolyte level) for effectiveness in treating a particular indication and/or region of the airway.

In addition to reducing the particle size (e.g., VMD) of the inlet aerosol (e.g., $A_{IN}$) to a desired output particle size (e.g., $A_{OUT}$), in some embodiments, the particle selection chamber 1200 and the nozzle 1170 are collectively configured such that the volumetric median diameter of the outlet aerosol flow $A_{OUT}$ produced is substantially independent of the volumetric median diameter of the inlet aerosol $A_{IN}$. More particularly, in some embodiments, the particle selection chamber 1200 and the nozzle 1170 are collectively configured such that the volumetric median diameter of the outlet aerosol flow produced is between approximately one micron and approximately two microns when the volumetric median diameter of the inlet aerosol is within a range of between approximately four microns and approximately seven microns. Accordingly, in some embodiments, an aerosol preparation assembly 1100 can receive aerosol input from a variety of different aerosol generators, and maintain a substantially constant output. Such aerosol generators can include, for example, vibrating mesh nebulizers, jet nebulizers and ultrasonic nebulizers. Any suitable aerosol generator may be used, including, but not limited to, nebulizers based on vibrating mesh technologies from Aerogen Aeroneb™ Lab, Pro and Solo, Pari eFlow™ vibrating mesh technologies, vibrating horn technologies by Omron™, vibrating mesh or ultrasonic technologies from Philips and other manufacturers. FIGS. 14A-C are graphs illustrating an ability of aerosol preparation assembly 1100 to produce an aerosol output with stable particle size regardless of the input into such device from an aerosol generator.

The removal of a portion of the inlet aerosol via the aerosol preparation assembly 1100, as described above, also necessarily results in a decrease in the rate of delivery of the therapeutic agent. In particular, because a large amount of aerosol volume (and therefore mass) is contained in the large particles, the removal of large particles above certain size leads to decrease in the rate of aerosol emission (μl/min) and the rate of emission for the therapeutic agent contained in aerosol (mg/min). Table 1 displays the effect of removing large particles produced by Aerogen Aeroneb Pro nebulizer with 7% hypertonic saline drug product by a aerosol preparation assembly 1100 of an embodiment. While 75% of volume normalized particles had size above 4 μm for the standalone nebulizer, only 2% of volume normalized particles exiting port 1230 of aerosol preparation assembly 1100 of an embodiment were larger than 4 μm. Filtering out of large particles led to a decrease in the aerosol output in terms of volume of aerosolized fluid contained in aerosol particles emitted from particle selection chamber outlet 1230 per unit of time (μl/min). Additionally, the output of NaCl mass per unit of time (mg/min) from particle selection chamber outlet 1230 decreased accordingly.

TABLE 1

Removal of Large Aerosol Particles by Aerosol Preparation Assembly 1100

| Output | $DV_{50}$ (μm) | 0.3-1 μm (%) | 1-2 μm (%) | 2-3 μm (%) | 3-4 μm (%) | <4 μm (%) | Total (μl/min) |
|---|---|---|---|---|---|---|---|
| Standalone Nebulizer Aeroneb Pro | | | | | | | |
| | 6.6 | 1 | 5 | 9 | 10 | 75 | |
| Aerosol Volume output from nebulizer (μl/min) | | 6 | 31 | 55 | 61 | 458 | 613.4 |

TABLE 1-continued

Removal of Large Aerosol Particles by Aerosol Preparation Assembly 1100

| Output | DV$_{50}$ (μm) | 0.3-1 μm (%) | 1-2 μm (%) | 2-3 μm (%) | 3-4 μm (%) | <4 μm (%) | Total (μl/min) |
|---|---|---|---|---|---|---|---|
| NaCl mass output (mg/min)* | | 0.4 | 2.1 | 3.9 | 4.3 | 32.1 | |
| Aeroneb Pro Nebulizer with Aerosol Delivery System 10 | | | | | | | |
| | 1.6 | 17 | 49 | 23 | 8 | 2 | |
| Aerosol volume output from port 44 (μl/min) | | 10 | 28 | 14 | 4 | 1 | 58 |
| NaCl mass output from port 1230 (mg/min)* | | 0.7 | 2.0 | 0.9 | 0.3 | 0.1 | 4 |

*7% hypertonic saline solution used

Figure 15:
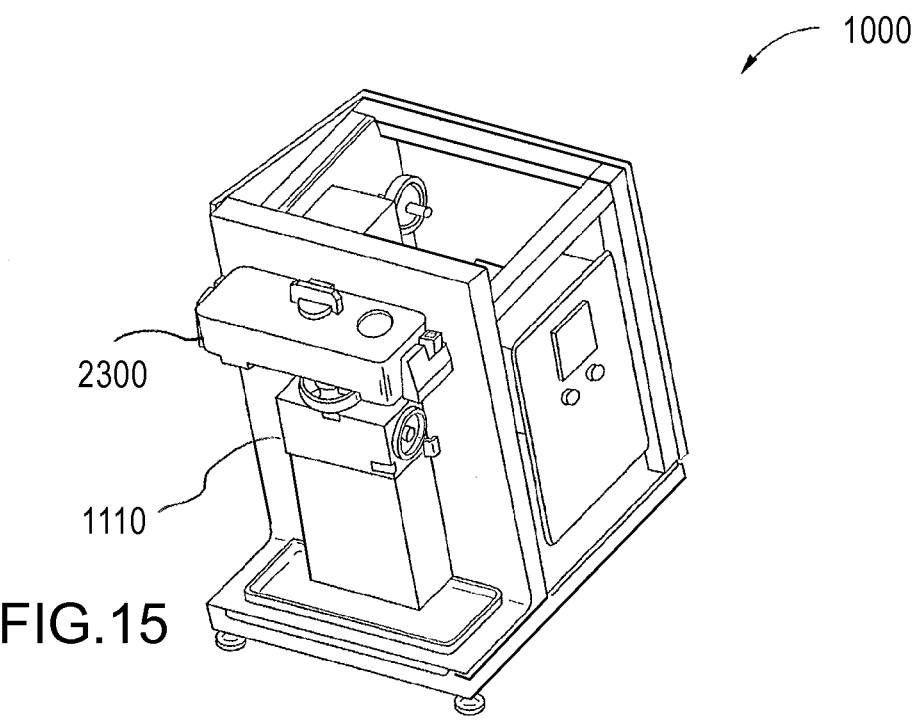
FIGS. 15-16 are schematic drawings of an aerosol delivery system in a portable unit according to some embodiments.
Figure 16:
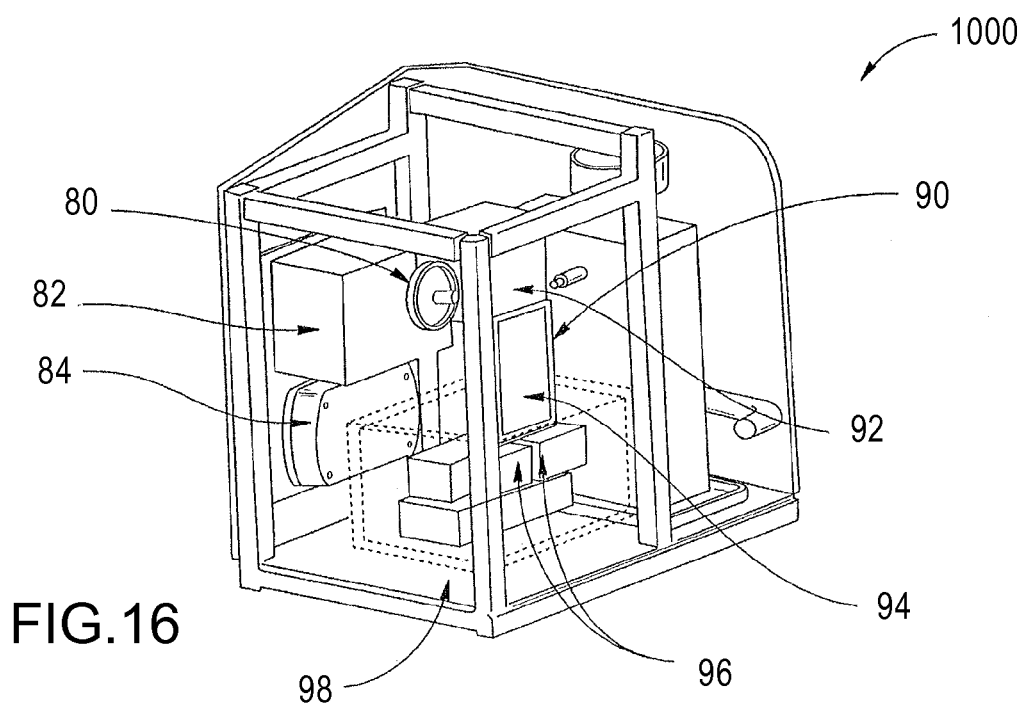

As shown in FIGS. 15-16, the aerosol preparation assembly 1100 can be disposed within and/or as a part of a central region 90 of a container or aerosol delivery system 1000, which may include various auxiliary components for operating the aerosol delivery system 1000. For example, the aerosol delivery system 1000 may include a nebulizer controller 84 for controlling the operation of the aerosol generator, an air pump 92, an optional compliance chamber 94, and a HEPA filter 80 for providing filtered air flow to the entrainment chamber inlet (i.e. similar to the gas source 400), an electronics unit 82 (similar to the controller 600) for enclosing electronics for controlling the operations of the pump 92 and other components of the unit 1000, power supplies 96 for providing power to various components of the delivery unit 1000 (such as the controller 84 and electronics unit 82), and a power switch 98 for turning the delivery unit 1000 on or off.

Figure 17A:
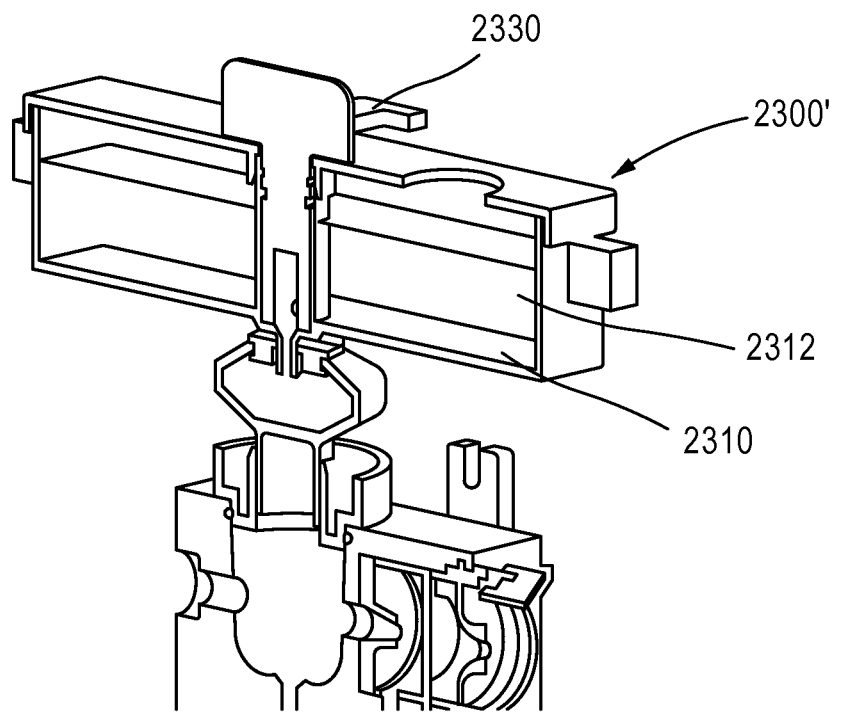
FIGS. 17A-17B are perspective views of a medicament container of FIG. 3, according to an embodiment, having portions cut away to show detail.
Figure 17B:
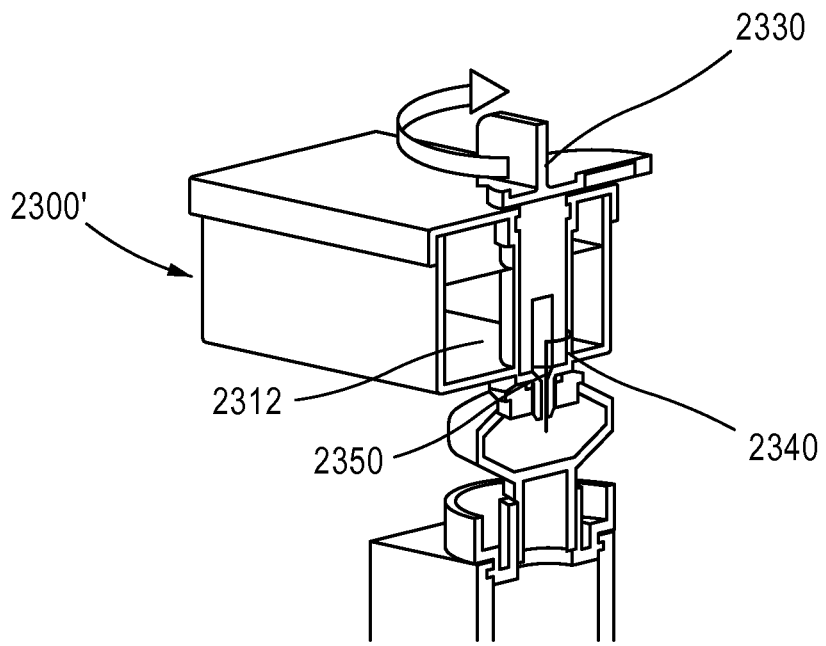
Figure 17C:
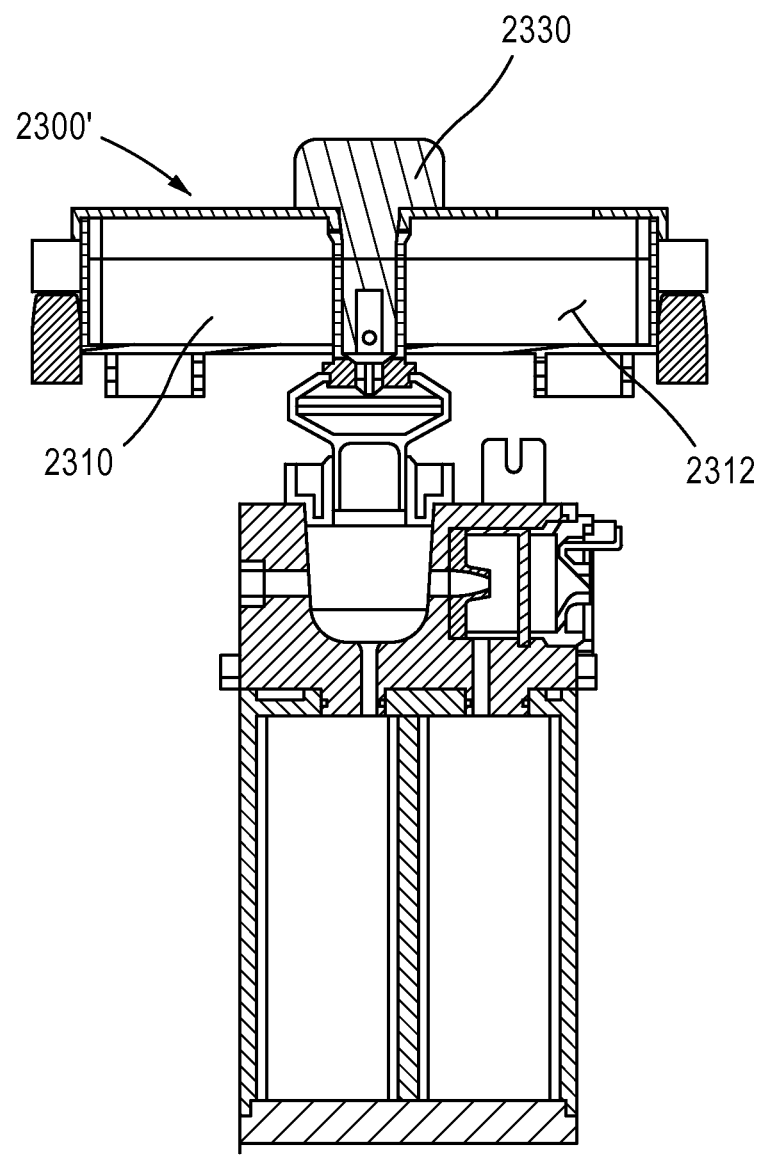
FIG. 17C is a front view of the medicament container of FIGS. 17A-17B.

As illustrated in FIGS. 17A-17C, in some embodiments, a medicament cartridge 2300' can be coupled to an aerosol preparation assembly, and more particularly to an aerosol generator (e.g., any of the aerosol generators disclosed herein). The cartridge 2300' includes a medicament reservoir/container 2310 and a valve 2330. The reservoir 2310 defines a volume 2312 containing a medicament to be delivered. The valve 2330 controls flow between the reservoir 2310 and the aerosol generator. In some embodiments, the valve 2330 can be further configured to limit head pressure on the aerosol generator. In particular, FIG. 17B shows the valve 2330 in an open position, and FIGS. 17A, 17C shows the valve 2330 in a closed position. In this manner, aspects of some embodiments are operable to prevent damage to the aerosol generator, ensure desired performance of the aerosol generator or the like. In particular, in some aerosol generators, too much column height can disrupt operation and/or damage structures for aerosol generation.

The medicament can be any of the medicaments listed here, and/or a combination thereof. As discussed earlier for FIG. 3, the medicament cartridge 2300' can be removably coupled to the aerosol generator, and thereby to the aerosol preparation assembly 1100. The valve 2330 can be of any suitable type rotatable between the open/closed positions illustrated in FIGS. 17A-17B. For example, as shown the valve includes a cross drilled portion 2340 that forms a through passage 2350 connecting the reservoir 2310 and the aerosol generator when the valve 2330 is in the open position. As also illustrated in FIGS. 17A-17B, the valve 2330 can extend through the reservoir 2310 to provide a manipulation means for switching the open/closed state of the valve.

Any of the systems shown and described herein (e.g., the system 1000) can be coupled to nasal cannula through which the outlet aerosol (see, e.g., A$_{OUT}$ in FIG. 2) can be conveyed to the patient (as the delivered aerosol, see A$_{DEL}$ in FIG. 2). In some embodiments, a nasal cannula is configured to minimize rainout and/or sputtering of the aerosolized particles. For example, in some embodiments, a nasal cannula can be configured to minimize and/or eliminate sedimentation and/or impaction of the aerosol as the aerosol is conveyed therethrough. In some embodiments, a nasal cannula and a portion of the aerosol preparation assembly (e.g., the cannula outlet port 1230) can be configured to collectively include a substantially continuous inner surface at the junction between the nasal cannula and the aerosol preparation assembly, as described above with reference to FIG. 4.

In some embodiments, delivery of an aerosol via nasal cannula over extended periods of time (e.g., longer than 30 minutes) while minimizing rainout is performed by a delivery system (e.g., the system 1000) that includes a nasal cannula that is matched to (i.e., that functions cooperatively with) the aerosol preparation device (e.g., the aerosol preparation device 1110). For example, nasal cannulas with larger diameter tubing and fewer impaction surfaces may be used to deliver aerosols containing a larger volume of particles above 2, 3 and 4 μm, respectively. Conversely, nasal cannulas with smaller diameter tubing may result in a higher velocity of the aerosol therethrough, but may also result in increased impaction. Accordingly, smaller diameter cannulas may be more capable of conducting aerosols over extended periods of time and at sufficient output levels where the aerosol contains a smaller volume of particles above 2, 3, and 4 μm, respectively. Thus, in some embodiments, a nasal cannula assembly includes components and is sized to be tolerable to patients (e.g., having an appropriate diameter, being configured to minimize rainout and/or sputter), while also being capable of delivering the desired dosage.

More specifically, in some embodiments, an inner diameter of a nasal cannula assembly can be selected to reduce gravitational sedimentation of the aerosol particles, which can accumulate as rainout in the cannula. For example, sedimentation may be reduced by decreasing the diameter of the tubing (such as the tube 1530) used in the cannula assembly, thereby producing an increased velocity with which the aerosol travels through the nasal cannula. Moreover, methods according to an embodiment can include increasing the airflow from 1 to 2 L/min to 3 to 4 L/min, and/or higher.

In some embodiments, a nasal cannula assembly can be configured to reduce inertial impaction of the aerosol particles on the side walls thereof, which can accumulate as rainout in the cannula assembly. For example, in some embodiments, a nasal cannula assembly can include a bifurcation structure having a geometric shape to reduce impaction at a bifurcation point (e.g., at the interface between the supply tubing and the face-piece tubing). In other embodiments, portions of a nasal cannula assembly can be constructed such that the inner surfaces are smooth and substantially free from ridges, surface roughness or the like.

Figure 18A:
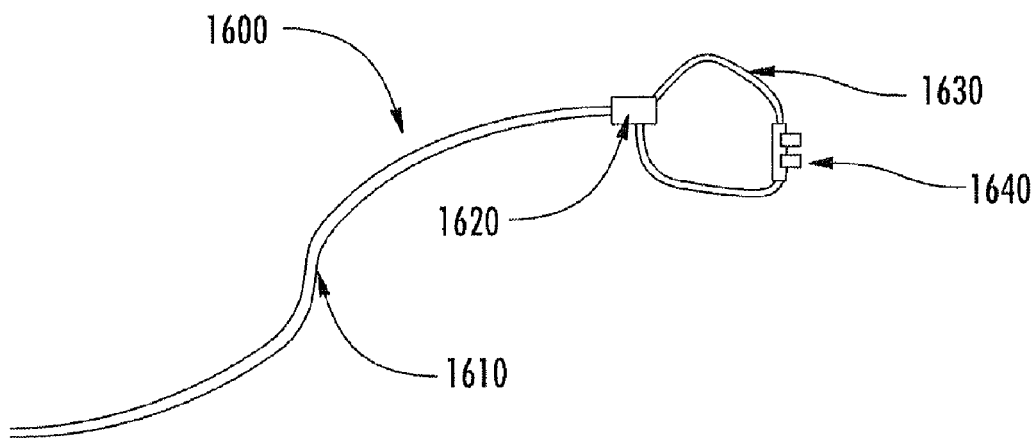
FIG. 18A is a schematic illustration of a conventional nasal cannula assembly of the prior art.
Figure 18B:
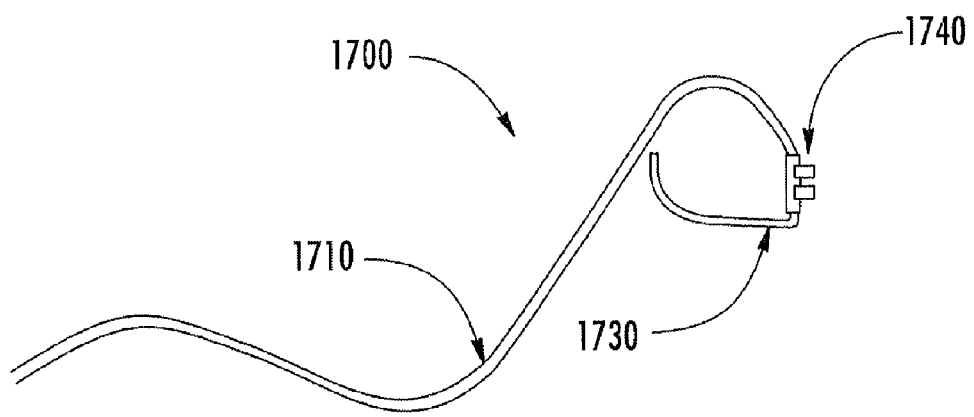
FIGS. 18B-18D are schematic illustrations of nasal cannula assemblies according to some embodiments.

In some embodiments, a nasal cannula assembly can be devoid of a bifurcation joint. For example, as illustrated in FIG. 18B, reduced rainout may be achieved, for example, by eliminating the bifurcation junction and by using a single line of supply tubing. As shown in FIG. 18B, a nasal cannula assembly 1700 includes supply tubing 1710, a dummy face-piece arm 1730 and nasal prongs 1740. Notably, the nasal cannula assembly 1700 does not include a bifurcation junction, and therefore, the rainout prior to the nose prongs 1740 may be reduced. In some embodiments, the dummy face-piece arm 1730 may be included to help secure the prongs 1740 on the patient; however, the face-piece arm 1730 may or may not be in fluid communication with the prongs 1740. A stopper or wall (not shown) may separate the prongs 1740 from the dummy face-piece arm 1730 such that the delivered aerosol $A_{DEL}$ is prevented from entering the dummy face-piece arm 1730. It should be understood that, in some embodiments, the dummy face-piece arm 1730 may be a hollow tube fluidly connected to the prongs 1740 and/or provide a drainage conduit for removing rainout and/or sputter.

Figure 18C:
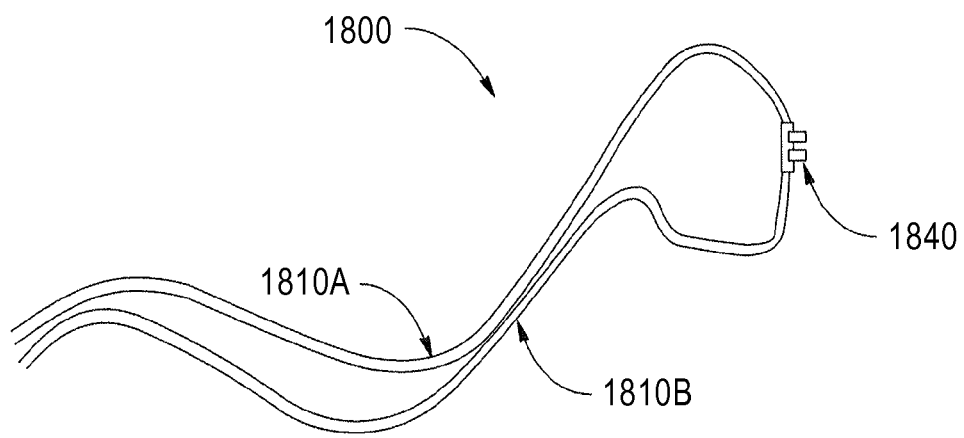

In some embodiments, rainout and/or sputtering may be reduced by using two separate supply lines. As illustrated in FIG. 18C, a nasal cannula assembly 1800 includes two separate supply lines 1810A, 1810B that are connected to respective ends of the nasal prongs 1840. Accordingly, a bifurcation junction from a single supply tubing line is eliminated, and two separate inputs to the nasal prongs 1840 are provided. An exit from the particle selection chamber 1230 (see, e.g., FIG. 8) can be modified to include two outputs to accommodate such dual supply lines. Furthermore, two independent particle selection chambers connected to single or two independent aerosol entrainment chambers can be used to provide aerosol supply into the dual cannula supply tubing lines. Furthermore, two or more complete aerosol preparation assembly systems (nebulizer, entrainment chamber and particle selection chamber) can be used to feed into the supply lines. Such an approach may also be used to increase the output from the prongs of the nasal cannula assembly 1800.

Figure 18D:
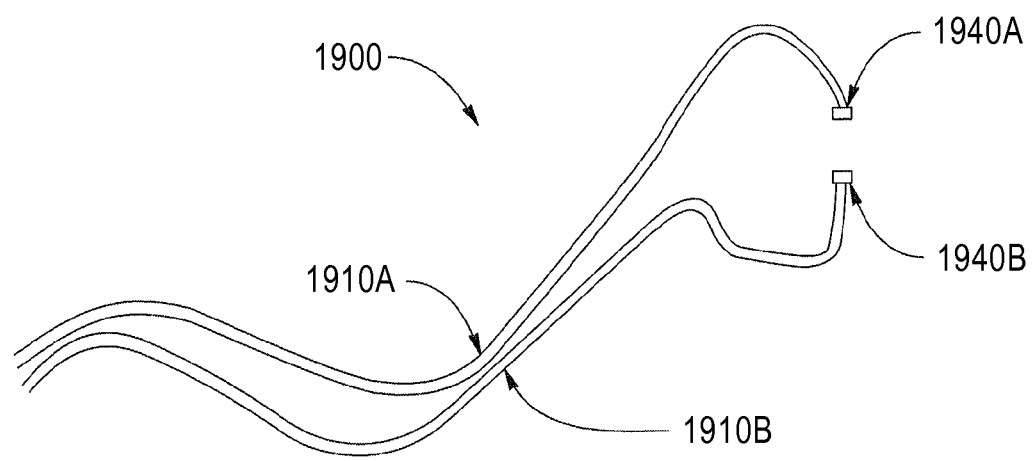

As shown in FIG. 18D, another nasal cannula 1900 includes two separate supply lines 1910A, 1910B, that are connected to individual nasal prongs 1940A, 1940B, respectively. The individual nasal prongs 1940A, 1940B reduce rainout and/or sputtering as compared with conventional nasal prongs that induce abrupt changes in the flow path, which may lead to inertial impaction and rainout.

Figure 19:
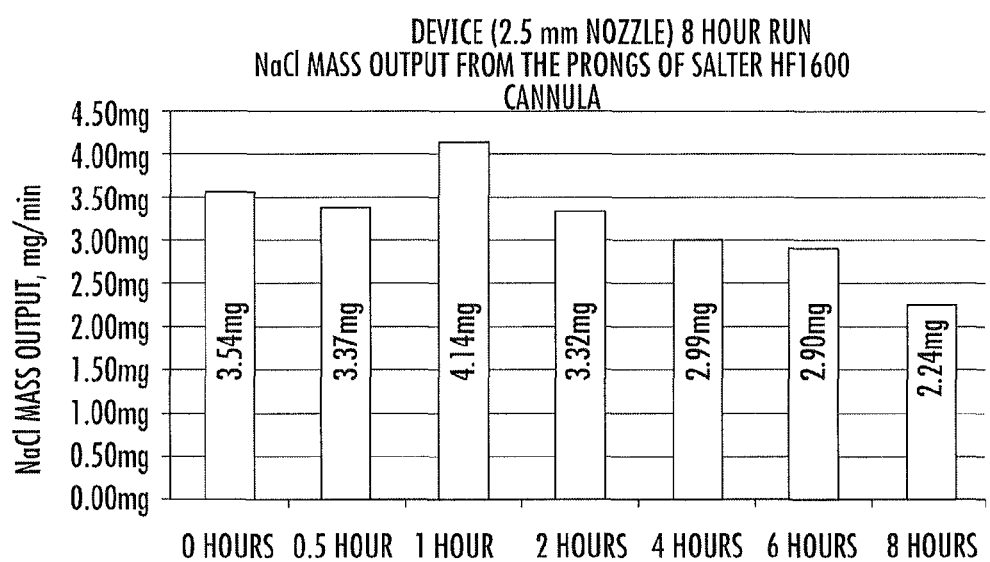
FIGS. 19-20 are bar graphs of the NaCl mass output for a particle selection chamber as shown in FIGS. 6-8, according to some embodiments.
Figure 20:
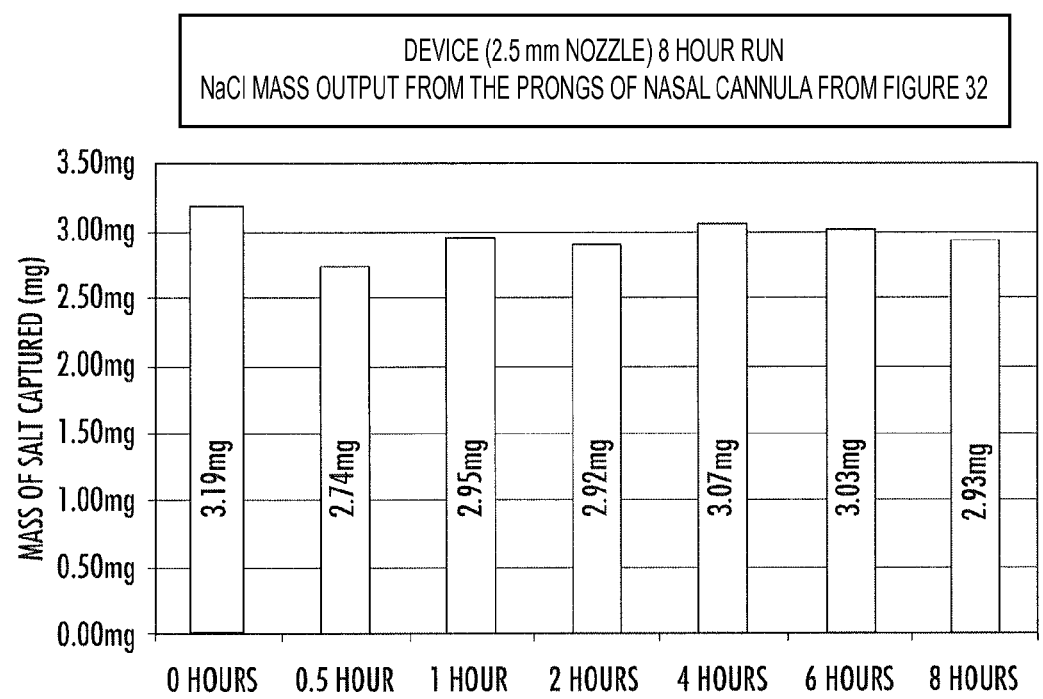

The cannula assemblies described above were tested to determine the efficacy of each embodiment in producing a substantially continuous flow with minimal rainout and/or sputter. For example, a comparison of the performance of the aerosol delivery system 1000 (see FIGS. 6-8, 15 and 16) equipped a prior art cannula (see FIG. 18A) and with the nasal cannula assembly 1700 was performed. In particular, as shown in FIG. 19, during an 8 hour run with a seven foot Salter HF1600 cannula (FIG. 18A) and the aerosol delivery system from FIGS. 6-8, a rainout of ~1.1 ml was observed, which caused a reduction in the aerosol output towards the later portion of 8 hour run. During a similar 8 hour run with the nasal cannula 1700 (which also has a length of 7 feet), a rainout of ~0.3 ml occurred, and there was substantially no decrease in the aerosol output towards the later portion of 8 hour run (FIG. 20). Table 2 below presents additional test data comparing the prior art cannula 1600 to the nasal cannula assemblies 1700 (FIG. 18B), 1800 (FIG. 18C) and 1900 (FIG. 18D).

TABLE 2

Performance of Standard and Optimized Cannulas in Extended Aerosol Delivery

| Cannula | INC nozzle (mm) | N repeats | $1^{st}$ min output, NaCl (mg/min) | $30^{th}$ min output, NaCl (mg/min) | Rainout (ul) | Rainout (%) | Sputter (ul, %) |
|---|---|---|---|---|---|---|---|
| Full HF1600 | 3.0 mm | n = 4 | 4.4 | 4.0 | 803 | 5.3 | N/A |
| Full HF1600 | 2.5 mm | n = 2 | 3.1 | 3.4 | 203 | 1.1 | N/A |
| Custom #1 | 3.0 mm | n = 2 | 5.6 | 4.7 | 610 | 3.9 | N/A |
| Custom #1 | 2.5 mm | n = 2 | 3.0 | 2.6 | 200 | 1.1 | N/A |
| Custom #2 | 3.0 mm | n = 2 | 4.7 | 3.9 | 360 | 2.0 | 0, 0 |
| Custom #2 | 2.5 mm | n = 3 | 3.1 | 2.8 | 151 | 0.8 | 0, 0 |
| Custom #3 | 3.0 mm | n = 2 | 4.1 | 3.8 | 262 | 1.5 | 54, 0.3 |
| Custom #3 | 2.5 mm | n = 2 | 3.0 | 3.0 | 110 | 0.6 | 0, 0 |

Although the entrainment chamber 1120 shown and described above defines a substantially linear pathway 1143 between the inlet port 1121 and the outlet port 1130, in other embodiments, an entrainment chamber can include any suitable geometry and/or can define any suitable flow path configuration to promote and/or enhance entrainment of the inlet aerosol into the entrainment fluid. For example, although shown as defining a sudden expansion, in some embodiments, an entrainment chamber need not define a sudden expansion. Moreover, although shown as defining a flow path that is substantially normal to an outlet axis of the aerosol generator, in other embodiments, an entrainment chamber can define one or more flow paths in relation to the aerosol generator having any suitable geometry or configuration.

Figure 21A:
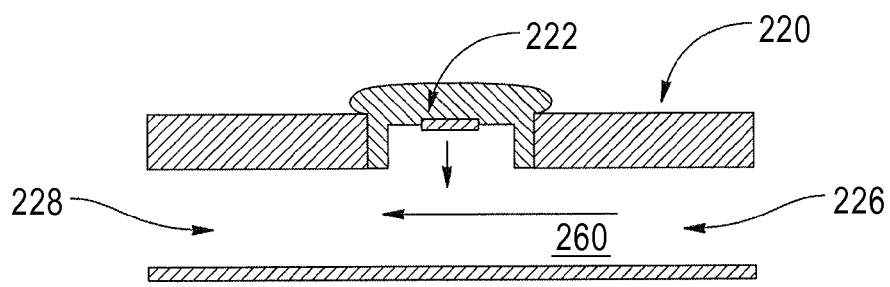
FIGS. 21A-21E and 22A-22B are schematic illustrations of various entrainment chambers, according to some embodiments.
Figure 21B:
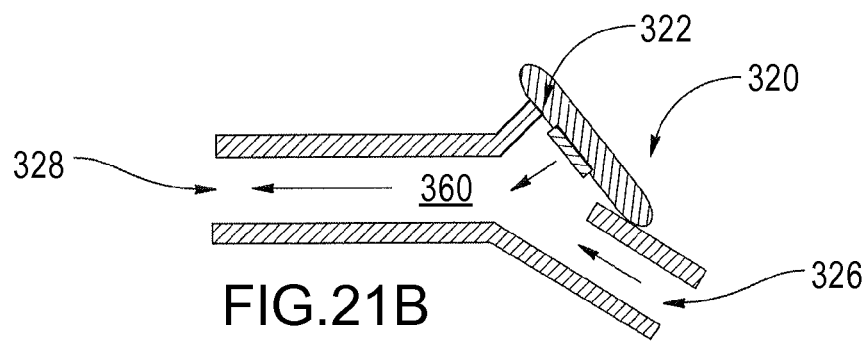
Figure 21C:
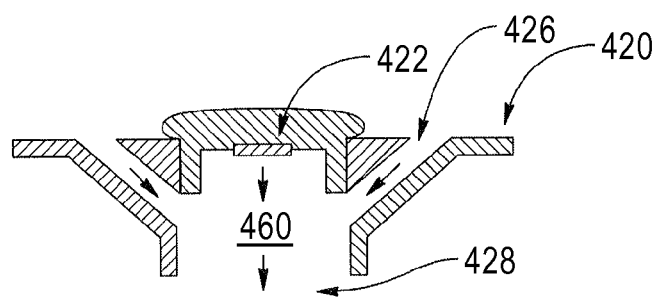
Figure 21D:
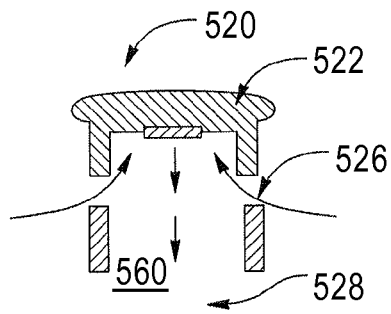
Figure 21E:
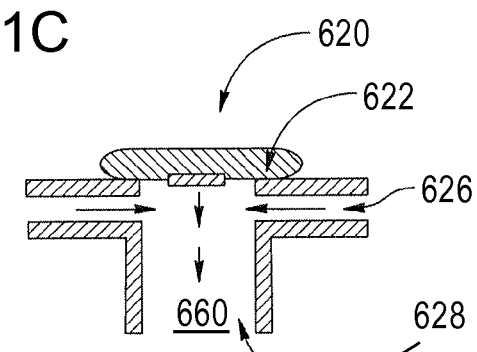

For example, FIG. 21A shows an entrainment chamber 220 having an aerosol generator 222, an inlet 226 and an outlet 228 that are configured to provide an entrainment fluid pathway 260. As illustrated in FIG. 21A, the entrainment chamber 220 is configured as a generally straight passageway for providing a fluid flow or fluid pathway 260. As illustrated in FIG. 21B, an entrainment chamber 320 includes an aerosol generator 322, an inlet 326 and an outlet 328 that provides an entrainment fluid pathway 360 and entrains the aerosol in an angle. As shown in FIG. 21C, an entrainment chamber 420 includes an aerosol generator 422 and inlets 426 for providing a fluid flow entering in a downward direction from the sides of the chamber 420 to provide a downward fluid pathway 460 that exits at an outlet 428. As shown in FIG. 21D, an entrainment chamber 520 includes an aerosol generator 522 and inlets 526 for providing a fluid flow entering in a upward direction from the sides of the chamber 520 to provide a downward fluid pathway 560 that exits at an outlet 528. As shown in FIG. 21E, an entrainment chamber 620 includes an aerosol generator 622 and inlets 626 for providing a fluid flow entering at a generally perpendicular direction from the sides of the chamber 620 to provide a downward fluid pathway 660 that exits at an outlet 628.

Figure 22A:
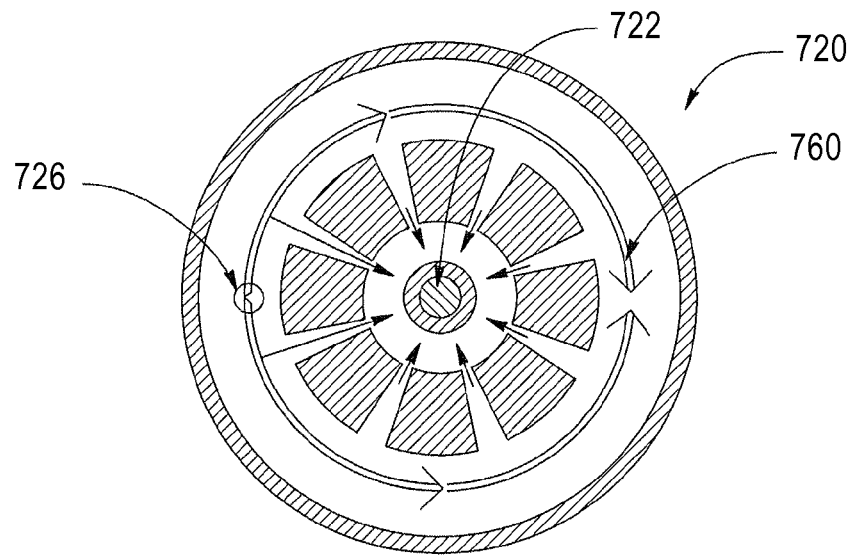
Figure 22B:
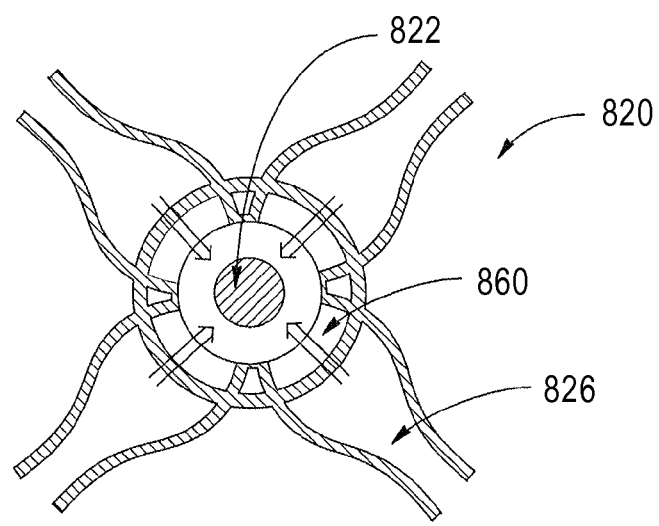

As shown in FIGS. 21A-D, the entrainment fluid may be provided by one or more inlets from the sides of the entrainment chamber adjacent the aerosol generator. In some embodiments as shown in FIG. 22A, an entrainment chamber 720 with an aerosol generator 722 may include an inlet 726 that provides a generally circular fluid flow 760 that then enters a central region of the chamber 720 via channels 726A. The fluid flow 760 may then exit the chamber 720 in a direction away from the aerosol generator 722, for example, as illustrated in FIGS. 21A-D. As shown in FIG. 22B, an entrainment chamber 820 includes an aerosol generator 822 and a plurality of inlets 826 for providing a sideward fluid flow pathway 860 for entraining the aerosol therein. The fluid flow 860 may then exit the chamber 820 in a direction away from the aerosol generator 822, for example, as illustrated in FIGS. 21A-D.

Referring to FIG. 2, although the particle selection chamber 1200 shown and described above defines a substantially linear pathway 1243, and includes a single baffle 1246 upon which aerosol particles impinge, in other embodiments, a particle selection chamber can include any suitable geometry and/or can define any suitable configuration to promote and/or enhance selection and/or filtering of the entrained aerosol $A_{ENT}$ to achieve the desired particle size distribution. For example, although shown as a single baffle, in some embodiments, a particle selection chamber can include any number of baffles or flow-directing members (not shown). Moreover, although shown as defining a flow path that is substantially linear (with exception of the curvature about the baffle 1246), in other embodiments, a particle chamber can define one or more flow paths that produce a cyclone and/or vortex within the flow to produce the outlet aerosol having the desired particle size distribution.

Figure 23A:
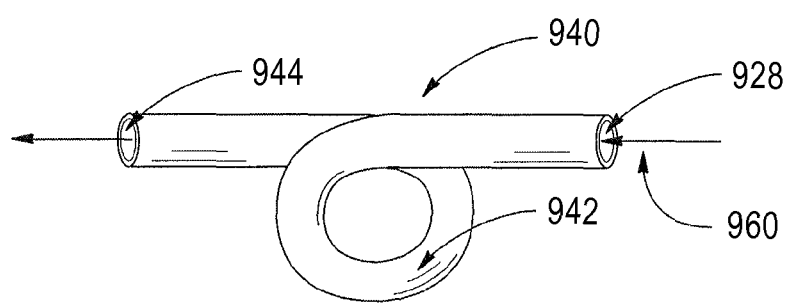
FIGS. 23A-23C are schematic illustrations of various particle selection chambers, according to some embodiments.
Figure 23B:
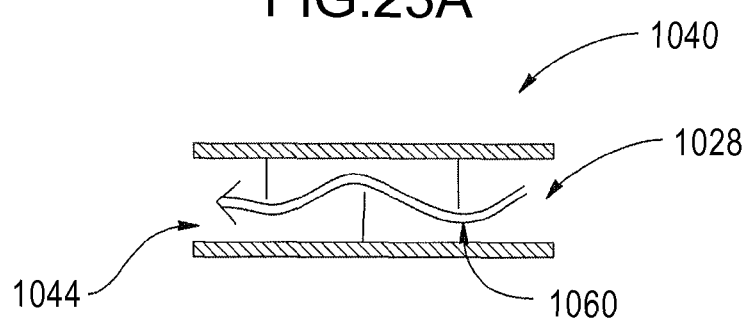
Figure 23C:
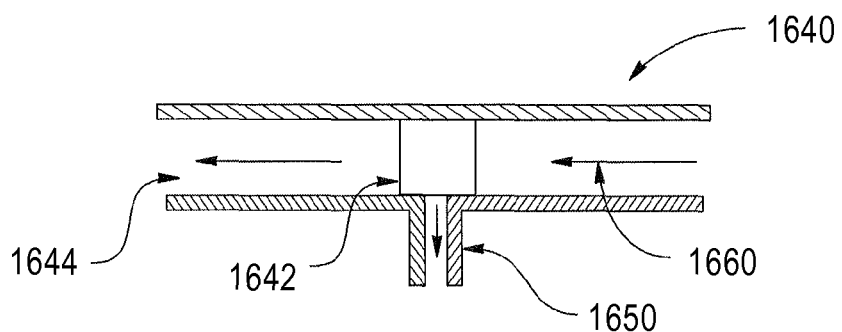

For example, as illustrated in FIG. 23A, a particle selection chamber 940 can include a generally tubular member that has an inlet 928 and an outlet 940 and a curved portion 942. Although the particle selection chamber 940 is illustrated with one curved portion 942, it should be understood that multiple loops may be provided. As illustrated in FIG. 23B, a particle selection chamber 1040 can include an inlet 1028, an outlet 1044, and a plurality of baffles 1042 that provides a curvilinear fluid pathway 1060 by partially blocking a portion of the chamber 1040. Although the particle selection chamber 1040 is illustrated with three baffles 1042, it should be understood that any suitable number of baffles may be used. As illustrated in FIG. 23C, a particle selection chamber 1640 can include an inlet 1628, an outlet 1644, and a particle or mesh filter 1642 that that traps particles of a given size in an entrainment fluid pathway 1660. The rain out or liquid aerosol particles from the filter 1642 then exit the chamber 1640 via a drain 1650

Figure 24A:
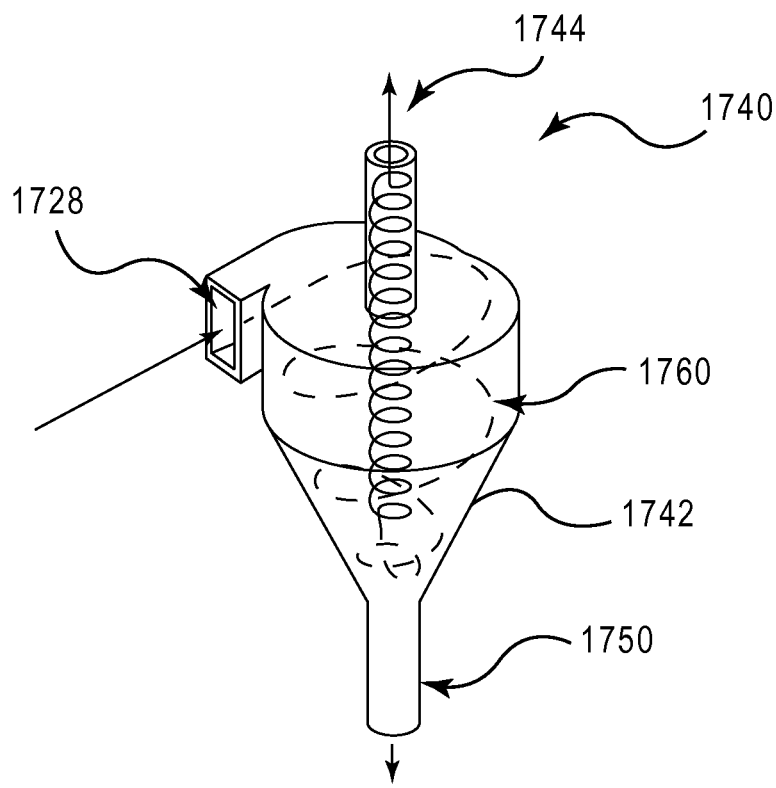
FIGS. 24A-24B are schematic illustrations of various particle selection chambers, according to some embodiments
Figure 24B:
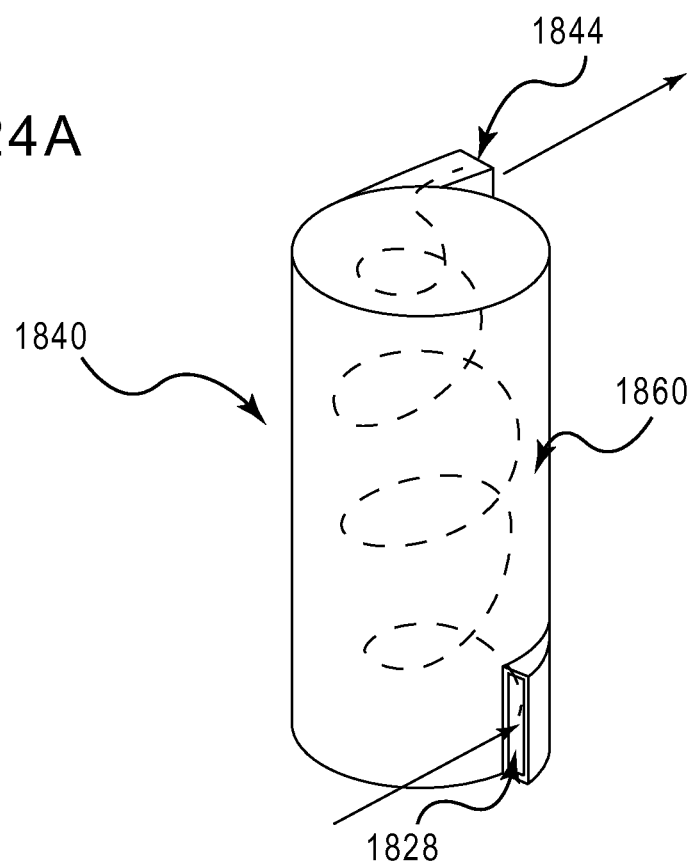

In some embodiments, non-linear fluid pathways may be provided by a particle selection chamber that is configured to create a generally circular or "cyclone" fluid flow. For example, as illustrated in FIGS. 17 and 18, a "cyclone" passive filtration system is illustrated for removing larger aerosol droplets through centrifugal deposition. As illustrated in FIG. 24A, a particle selection chamber 1740 can include an inlet 1728, an outlet 1744, a tapered body 1742 and a drain 1750. The curved body 1742 is configured to create the fluid pathway 1760, which spirals in a downward direction from the inlet 1728 to the drain 1750 and then spirals in an upward direction toward the outlet 1744. The radius of the downward direction of the pathway 1760 is generally greater than in the upward direction. As illustrated in FIG. 24B, a particle selection chamber 1840 can include an inlet 1828 at one end and an outlet 1844 at the opposite end. The chamber 1840 is configured to provide a spiral-shaped fluid pathway 1860 through the cylindrical chamber 1840.

Figure 25:
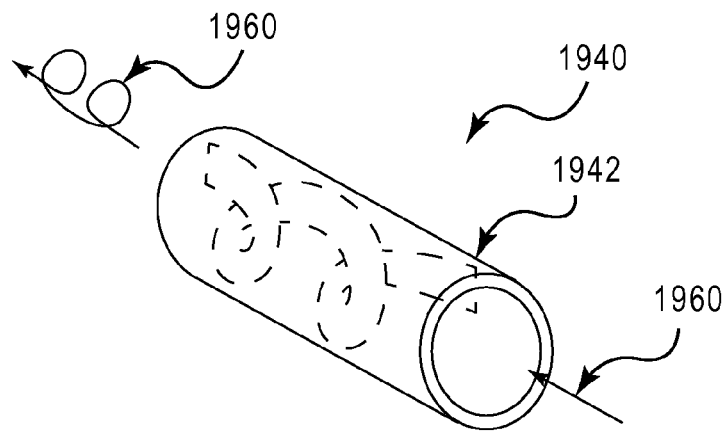
FIGS. 25-27 are schematic illustrations of various particle selection chambers, according to some embodiments.
Figure 26:
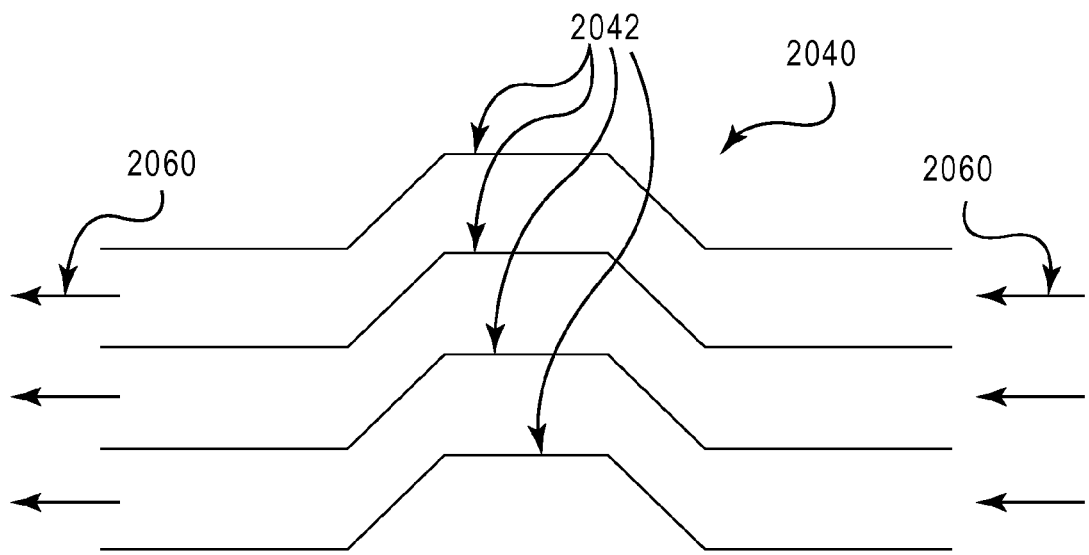
Figure 27:
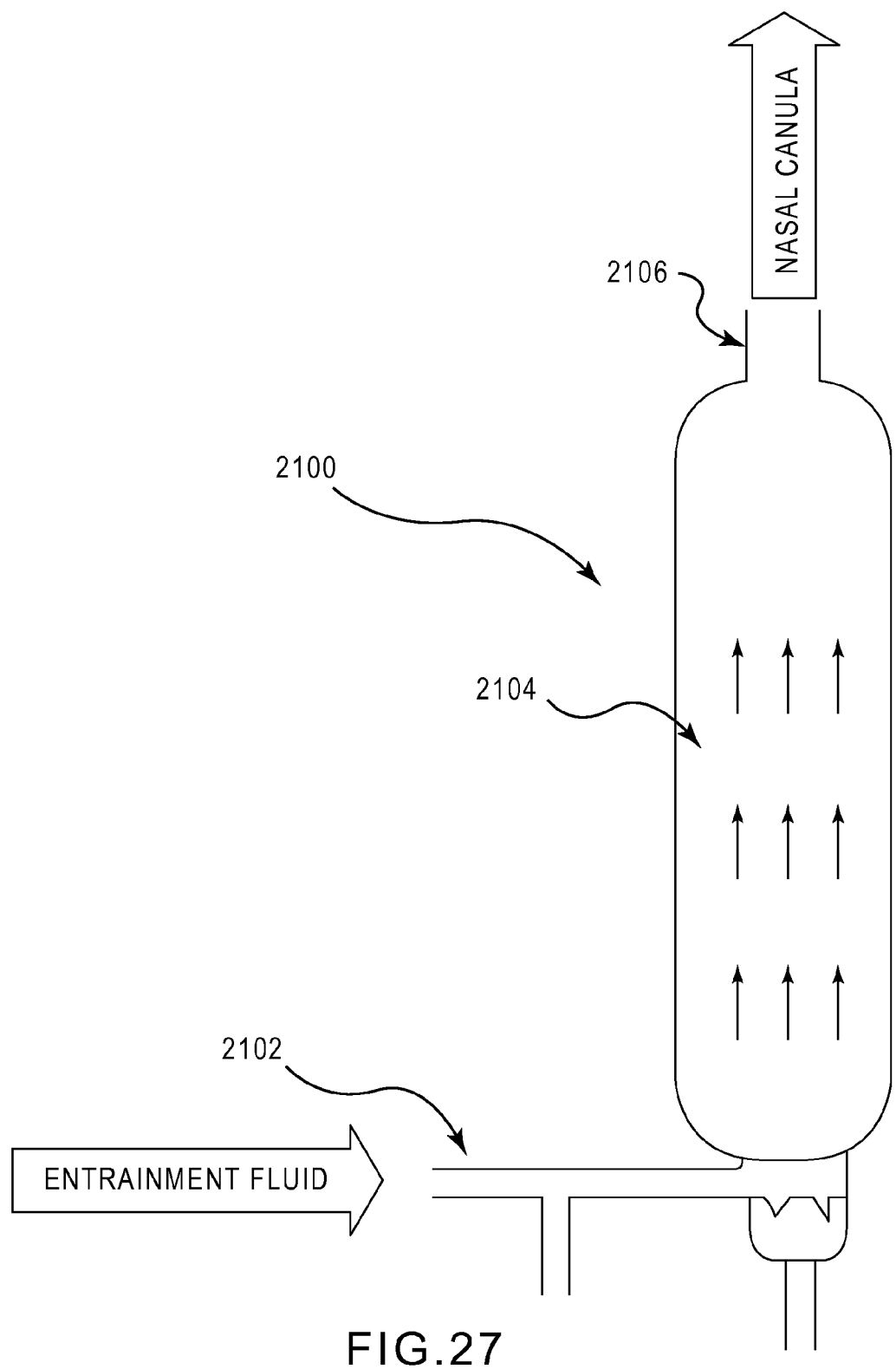

In some embodiments, mechanical components may be used to provide a non-linear flow pathway in the particle selection chamber. For example, as shown in FIG. 25, a cylindrical particle selection chamber 1940 includes a spiral barrier 1942 that forms a spiral flow pathway 1960. As shown in FIG. 26, a particle selection chamber 2040 includes a plurality of nonlinear passageways 2042 for bending the flow pathway 2060. In some embodiments as shown in FIG. 27, particle selection occurs in the elutriator 2100. The elutriator 2100 includes an intake 2102 and a vertical body 2104 and an output 2106. The intake 2102 is connected to a nebulizer, and in the air elutriator body 2104, particles are ejected from a small fluidized bed into a flow of air and carried upwards. The air velocity may determine the particle size selection such that as the air velocity is increased, larger and larger particles are carried over.

Although the aerosol preparation assembly 1100 is shown and described above as including one entrainment chamber 1120 and one particle selection chamber 1200, in other embodiments an aerosol preparation assembly can include any suitable number of entrainment chambers and/or particle selection chambers.

In some embodiments, the aerosol preparation assembly 1100 can be movable between a first (or opened) configuration and a second (or closed) configuration. When in the first configuration, the entrainment volume 1142 and/or the particle selection volume 1242 can be accessed for cleaning or the like. When in the second configuration, the entrainment volume 1142 and/or the particle selection volume 1242 can be closed for operation of the device. In some embodiments, a portion of the aerosol preparation assembly 1100 can be hingedly coupled together (e.g., in a clam shell configuration) to facilitate moving between the opened configuration and the closed configuration.

In some embodiments, the aerosol preparation assembly 3000, which is configured to recycle and/or recirculation portions of the rained out aerosol, can include and electronic controller (e.g., the electronic controller 600 described above with reference to FIG. 1) to facilitate any such recycling. A fluidics system may be controlled by electronic and/or mechanical system(s) that collect the rained out liquid containing the active pharmaceutical ingredient (API) collected between the vibrating mesh and the prongs of the nasal cannula. Such a system then may mix additional water or other solvent into the rained out liquid to restore the concentration of the API to the original concentration of the drug product before it was concentrated by the nebulization and rainout cycle. The extent of the concentration of the API within the rainout fluid in the course of extended aerosol infusions may either be determined by measurements of parameters such as, but not limited to, osmolarity, conductivity, UV/VIS spectra or other key parameter of the drug product solution allowing for determination of the concentration. Alternatively, a predetermined and preprogrammed algorithm based on historically measured values contained within the control circuitry could be used to add a dilution medium such as sterile water into a predetermined amount of rained out fluid. Such recycled fluid restored to its original concentration would be sterile filtered by a passage through a 0.22 um filter before re-nebulization, by exposure to UV light, and/or the like. Such fluidics system additionally may allow for dose metering by controlling the rate of the fluid injection into the aerosol generator. Such a system may be also built into the drug canister, which could contain the water or other fluid for concentration adjustment in addition to the fill dose of the drug product. Alternatively, the aerosol generator output may be modified and tuned down as the concentration of the API increases due to drug recycling. The concentration of the API may be measured within the aerosol preparation assembly or pre-determined so that the aerosol generator output is tuned down gradually. In this manner, the rate of API emission from the prongs of the nasal cannula assembly can remain essentially constant over the course of the aerosol infusion, lasting from 30 min to 24 hours/day In some embodiments, a gravity-fed drug canister, such as that generally disclosed in FIGS. 3 and 17A-17B, or other drug canister can be configured to limit the liquid column height (which exerts pressure on the vibrating mesh membrane of a nebulizer, when the aerosol generator is a nebulizer), to 50 mm for the Aerogen Aeroneb Lab and Pro vibrating mesh membranes. For certain aerosol generators, liquid columns higher than 50 mm may lead to decrease in the output of the membrane due to the hydrostatic pressure.

In some embodiments, a drug canister/cartridge can include a filter (e.g. a 0.22 μm filter) at the exit port thereof. In such embodiments, the contained liquid formulation/medicament of the drug product is dispensed from the exit port to be fed towards the aerosol generator, which can prevent contamination due to blowback and potential pathogen replication in the course of prolonged aerosol infusion lasting from 0.5 to 24 hours per day.

In some embodiments, the drug canister containing an electronic monitoring system for keeping track of the time of use, and for disabling the ability to use the drug container after a certain time of use, or after expiration of the shelf life of such container may be provided, and/or the like. Such a system increases patient safety by reducing and/or preventing refills formulated by unqualified personnel.

In some embodiments, the drug canister can contain a unique interface with the device allowing secure locking/docking of the drug canister into the device. A secure and sterile connection can be made for the passage of the medicament into the aerosol generator, and for one-way or two-way electronic communication between the aerosol generator and the drug canister.

For APIs without extended stability, the drug canister can contain dry powder capsules of the API with the excipients that would be reconstituted prior to nebulization either within the drug canister and/or within the aerosol generator. The drug canister or the base station may contain sterile distilled water cartridges for reconstitution of the dry powder into the liquid formulation of the drug product.

Although shown and described above as including a compliance chamber and/or being operable with a substantially steady-state flow of inlet gas, in other embodiments, it may be desirable to use a pulsed air flow. In other words, in some embodiments, the gas entraining the aerosol can be characterized by a pulsatile flow profile (i.e., a flow having periodic variations or that is characterized as being substantially transient). This arrangement may produce lower particle size selections and/or more efficient particle selection compared to non-pulsative entrainment fluids of the same average flow-rate (with all other factors, such as nozzle diameter and baffle size and shape being equal). The source of such pulsatile flow may be, but is not limited to, a diaphragm pump, a peristaltic pump, a rotary vane pump or compressed gas with an actuated valve producing the oscillatory pattern connected in series and upstream of the entrainment chamber.

Although the methods and systems are shown and described herein as producing a substantially continuous flow of aerosolized medicament over an extended time period (e.g., 8 hours), in other embodiments, a method can include periodic delivery of the aerosolized medicament over an extended period of time. In particular, because of the unexpectedly high deposition efficiency achieved the systems shown herein, in certain situations, a desired dosing level (for example, 300 mg of NaCl) can be completed in less than a desired time period. Accordingly, in some embodiments, a method includes cycling the airflow and/or the aerosol generator to produce periods of delivery and non-delivery during the treatment regimen. For example, in some embodiments, a method includes delivering a dosage of hypertonic saline for a first time period (the "on" period, e.g., 15 minutes) and then reducing and/or stopping the delivery for a second time period (the "off" period, e.g., 5 minutes), and then repeating this cycle for the treatment duration (e.g., 8 hours). In some embodiments, the first time period can be different from the second time period. In some embodiments, the "on period" can vary throughout the treatment regimen. This allows, for example, an initial or "priming" amount of the dosage to be delivered at the beginning of the treatment regimen.

Figure 28:
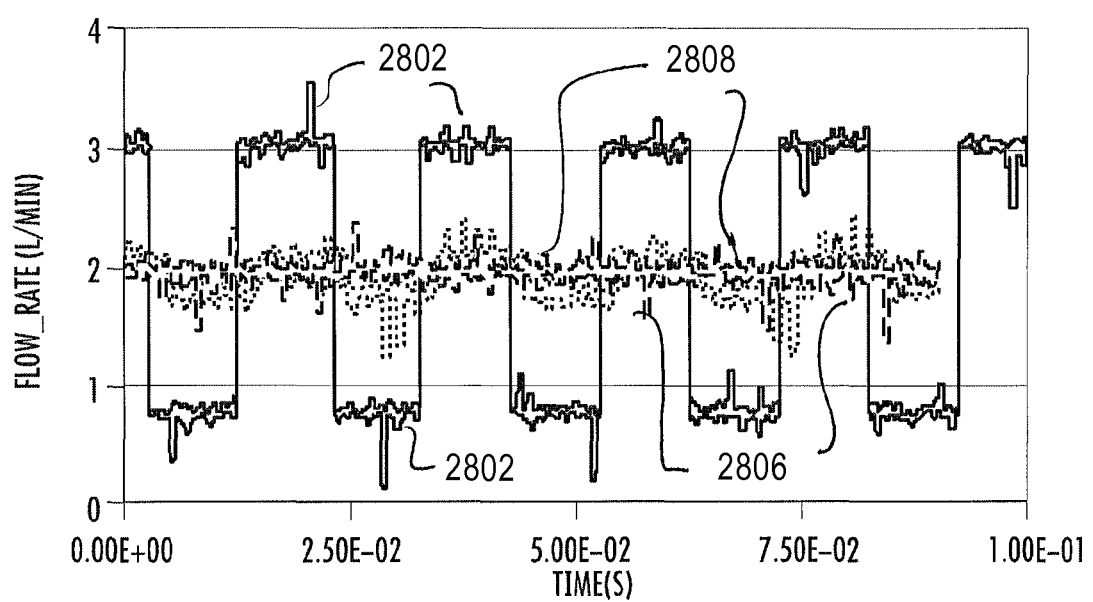
FIGS. 28-29 are plots of flow rate for the gas source of the aerosol delivery system of FIGS. 5-8, when operated using methods according to some embodiments.
Figure 29:
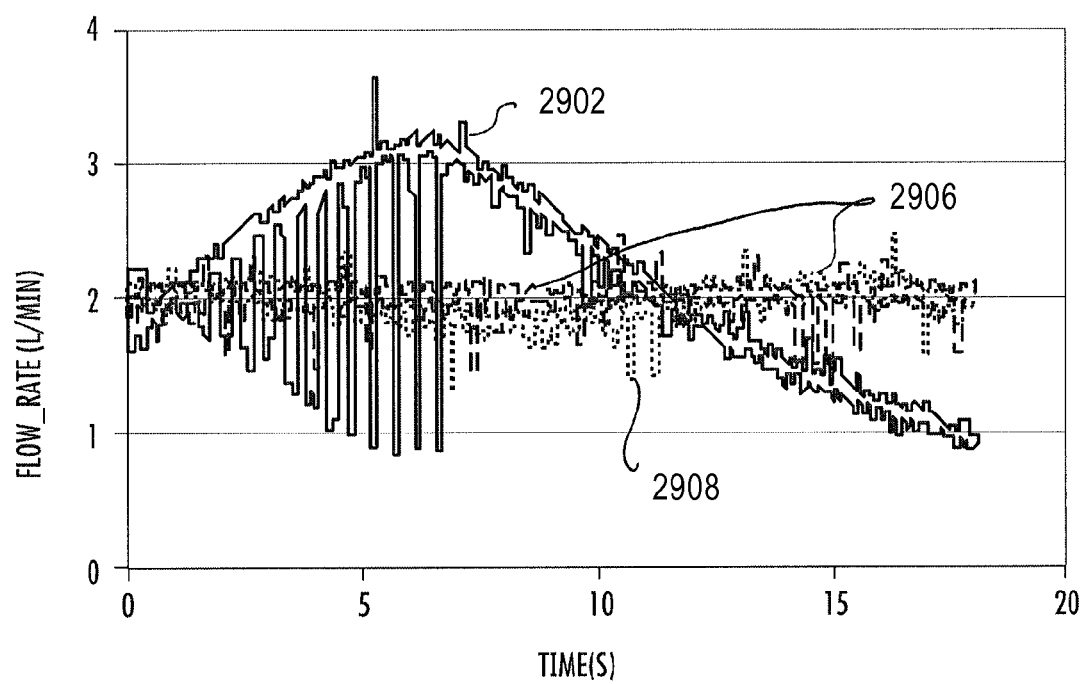

To assess flow pulsatility of a peristaltic pump used in testing of the devices in FIGS. 5-8, the analogue output of the flow meter TSI 4000 was wired to an Agilent Technologies mixed signal oscilloscope (E1457) and the data was logged to usb. Raw voltage was recorded and the flow rate post-processed (calibrated using the fact that the voltage output range 0-10 V represents a flow rate range from 0-200 L/min) at two frequencies (to investigate both small and large scale variations). A compliance chamber with a volume of 2 L was connected in line to the output of the pump and its impact was explored. FIGS. 28 and 29 displays the oscillatory nature of the pump output (the solid line, identified as trace 2802 in FIG. 28 and trace 2902 in FIG. 29) and the impact of 2 L compliance chamber on the amplitude of airflow (the dotted line, identified as trace 2808 in FIG. 28 and trace 2908 in FIG. 29). Compressed air was used to provide a steady airflow for comparison (the dashed line, identified as trace 2806 in FIG. 28 and trace 2906 in FIG. 29). The use of 2 L compliance chamber reduced or eliminated the oscillatory nature of the output from Pump A.

Figure 30:
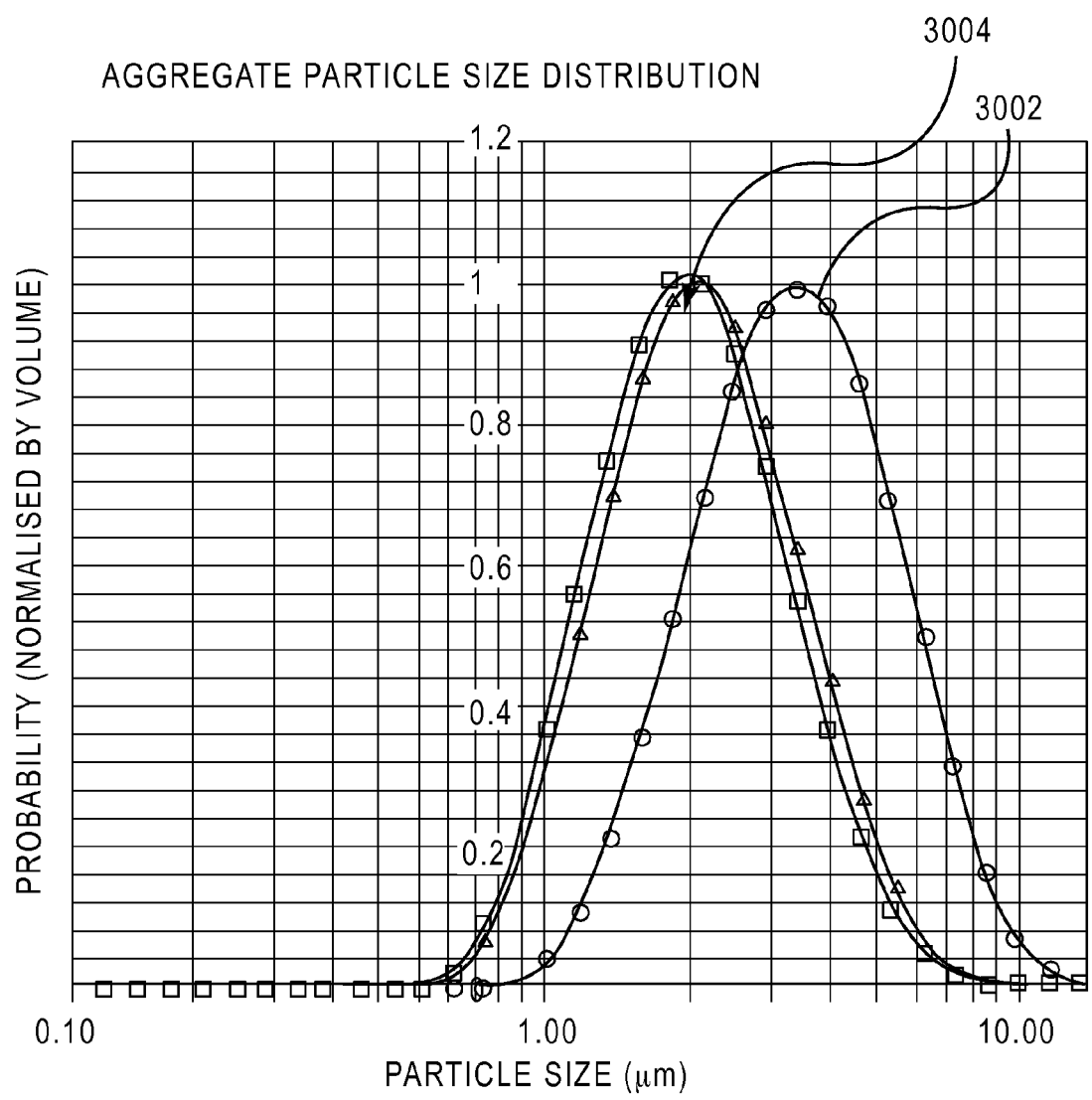
FIG. 30 displays aerosol output particle size distribution from a system according to an embodiment that includes a compliance chamber downstream of a peristaltic pump.

The ability of the aerosol preparation assembly 1100 (e.g., as shown in FIGS. 6-8) to remove large particles was explored with and without a compliance chamber and Pump A. Under identical operating conditions with 3.5 mm nozzle and 2 L/min average airflow, the oscillatory airflow produced by Pump A without a compliance chamber led to more effective removal of large particles compared to steady airflow from Pump A with a compliance chamber. As shown in FIG. 30, the VMD was 1.9 μm for the aerosol preparation assembly used without a compliance chamber (see trace 3004), and was 3.1 μm for the aerosol preparation assembly used with a compliance chamber (see trace 3002). The decreased VMD is accompanied by decreased rate of aerosol volume emission since large amount of aerosol volume is contained within the large aerosol particle. Given these outcomes, the aerosol preparation assembly 1100, and any other systems shown herein, are able to produce aerosols from port 1230 with (1) small percentage of particles above 3-4 μm and (2) sufficient rate of aerosol emission by either using a non-pulsatile airflow and a slightly smaller nozzle 28B diameter or by using a pulsatile airflow and slightly larger nozzle 28B diameter, all other factors and operating conditions being equal.

Figure 31:
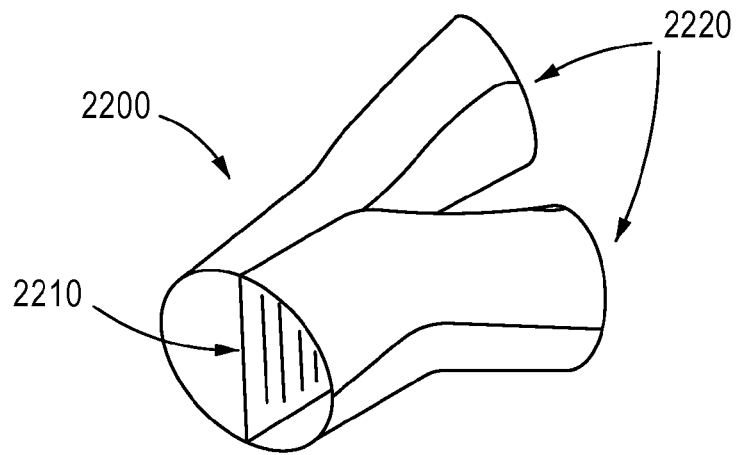
FIGS. 31-32 are schematic illustrations of cannula bifurcation junctions, according to some embodiments.
Figure 32:
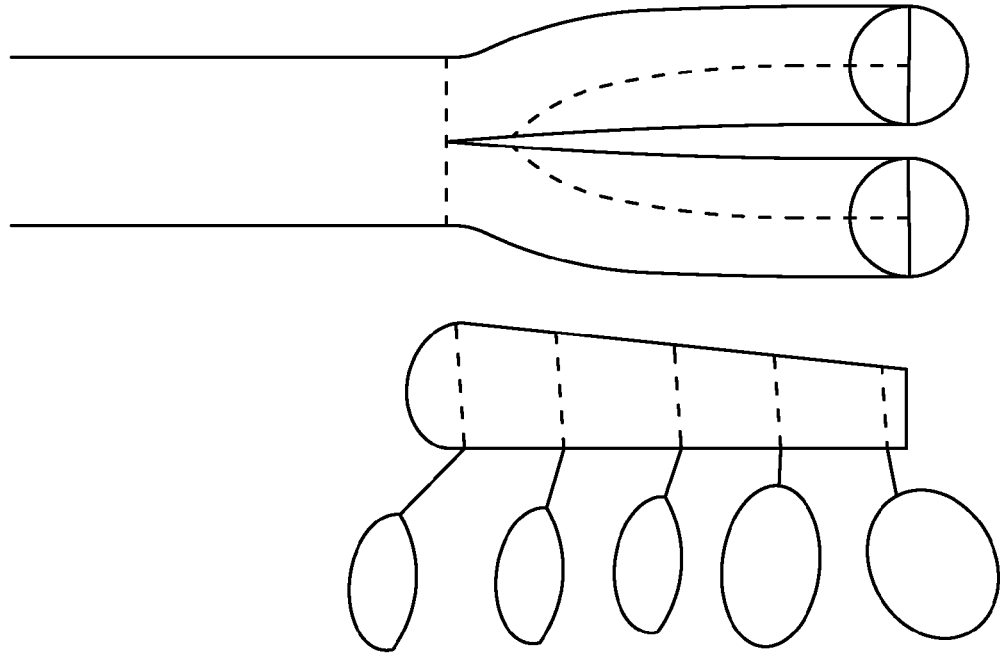

Although the nasal cannula assemblies 1700, 1800 and 1900 shown and described above as being devoid of a bifurcation, in some embodiments a nasal cannula can include a bifurcation and/or a flow member configured to split and/or separate the flow therethrough. Such embodiments can include features and/or define flow paths in contact with the flow member to minimize and/or reduce rainout due to impaction. For example, as illustrated in FIG. 31, a cannula bifurcation junction 2200 includes a separation partition 2210 that is introduced into the single supply line. The partition 2210 then separates into two bifurcated lines 2220 such that an impaction surface may be reduced. In some embodiments, the initial cross-sectional area following the bifurcation junction may be constant until a circular cross-section is attained, and then the cross-sectional area may be gradually decreased to gradually accelerate the speed of aerosol in the lower diameter tubing section heading to the nasal prong(s). Additional shapes of bifurcated cannula assemblies are disclosed in FIG. 32 wherein the shape of the cross-section following the bifurcation gradually changes shape to circular cross-section while keeping the area of the cross section, as well as the airflow, constant until circular cross-section is reached.

In some embodiment, a nasal cannula assembly can include an "active" rain-out management system, such as, for example, liquid rainout traps or absorbent materials placed/constructed within the nasal cannula tubing. In some embodiments, such active rainout management systems can retain and/or have a capacity of 0.5 to 2 ml, or 5 ml, or more, per about 8 hours of operation for systems such as those disclosed herein.

In some embodiments, a nasal cannula can include an adsorbent material coated along the length of the nasal cannula. Such adsorbent coating can be engineered to have the capacity to absorb 0.05 ml to 5, or 10 ml, of "rain-out" liquid. In some embodiments, the inner surface or a portion of any other surface of the cannula assembly may be manufactured from a liquid absorbent polymer or other liquid absorbent materials. The bifurcation junction may also be manufactured from a liquid absorbent polymer. The nose piece and/or the prongs may be manufactured from liquid absorbent polymer or other liquid absorbent materials.

In some embodiments, the internal surface of any of the nasal cannula assembly described herein can include and/or define cavities (ridges, bubbles etc.) designed to retain any rained out fluid.

As discussed above, the removal of a portion of the inlet aerosol via the aerosol preparation assembly 1100, as described above, also necessarily results in a decrease in the rate of delivery of the therapeutic agent. Accordingly, the rate of deposition (e.g., the total mass deposited per unit time) of a therapeutic compound using the systems (e.g., the aerosol delivery system 1000) and methods described herein will likely be lower than the rate of deposition of the same compound using known systems and methods. In particular, it has been demonstrated that approximately 110 mg to 250 mg of NaCl deposited (via oral delivery) in the lung of CF patients led to significant improvements in lung function when administered as a bolus aerosol dose for approximately 18 minutes (Elkins et al., A controlled trial of long-term inhaled hypertonic saline in patients with cystic fibrosis, N Engl J Med 354(3):229-240; Donaldson et al., Mucus clearance and lung function in cystic fibrosis with hypertonic saline, N Engl J Med 354(3):241-250). In some embodiments, a method includes delivering transnasally approximately the same mass of deposited NaCl (e.g., between approximately 110 mg and 250 mg, or higher) over extended times of six to eight hours (and up to twenty four hours per day). In particular, to deposit 110 mg of NaCl in the lung over an 8 hour extended aerosol infusion according to the methods described herein, the rate of NaCl mass deposition on the surface of the lung may be about 0.23 mg/min. For 250 mg NaCl dose deposited in the lung according to the methods described herein, the rate of NaCl mass deposition on the surface of the lung may be about 0.52 mg/min. These rates of NaCl mass deposition can be produced by a particular predetermined rate of aerosol volume deposition on the surface of the airway, the aerosol including a predetermined concentration of active pharmaceutical ingredient in the drug product.

For example, Table 3 provides such rates for the aerosol volume deposition on the surface of the airways as a function of concentration of HS in an aerosolized solution to provide the desired NaCl (mg) deposition rates.

TABLE 3

Rates for Aerosol Volume Deposition on the Surface of the Airways to Achieve Therapeutic Doses of NaCl Deposited over Eight Hour Aerosol Administration for Aerosolized Solutions with Different Concentration of NaCl

| | 7% HS | 10% HS | 12% HS | 14% HS | 21% HS |
|---|---|---|---|---|---|
| Aerosol volume (µl/min) and amount (mg/min) deposition rate on the surface of the airways to achieve 110 mg of NaCl deposited over 8 hour extended aerosol administration | | | | | |
| µl/min | 3.3 | 2.3 | 1.9 | 1.6 | 1.1 |
| mg/min | 0.23 | 0.23 | 0.23 | 0.23 | 0.23 |
| Aerosol volume (µl/min) and amount (mg/min) deposition rate on the surface of the airways to achieve 250 mg of NaCl deposited over 8 hour extended aerosol administration | | | | | |
| µl/min | 7.4 | 5.2 | 4.3 | 3.7 | 2.5 |
| mg/min | 0.52 | 0.52 | 0.52 | 0.52 | 0.52 |

The rate of NaCl mass and aerosolized NaCl solution volume deposited on the surface of the airways is a function of the deposition efficiency of the therapeutic composition and delivery system. Similarly stated, the rate of aerosol emission from the nasal cannula of the embodiments described herein to result in the pulmonary deposition of the targeted 250 mg of NaCl achieved over eight hour extended aerosol administration are dependent on the concentration of aerosolized NaCl solution and the deposition efficiency.

Figure 33:
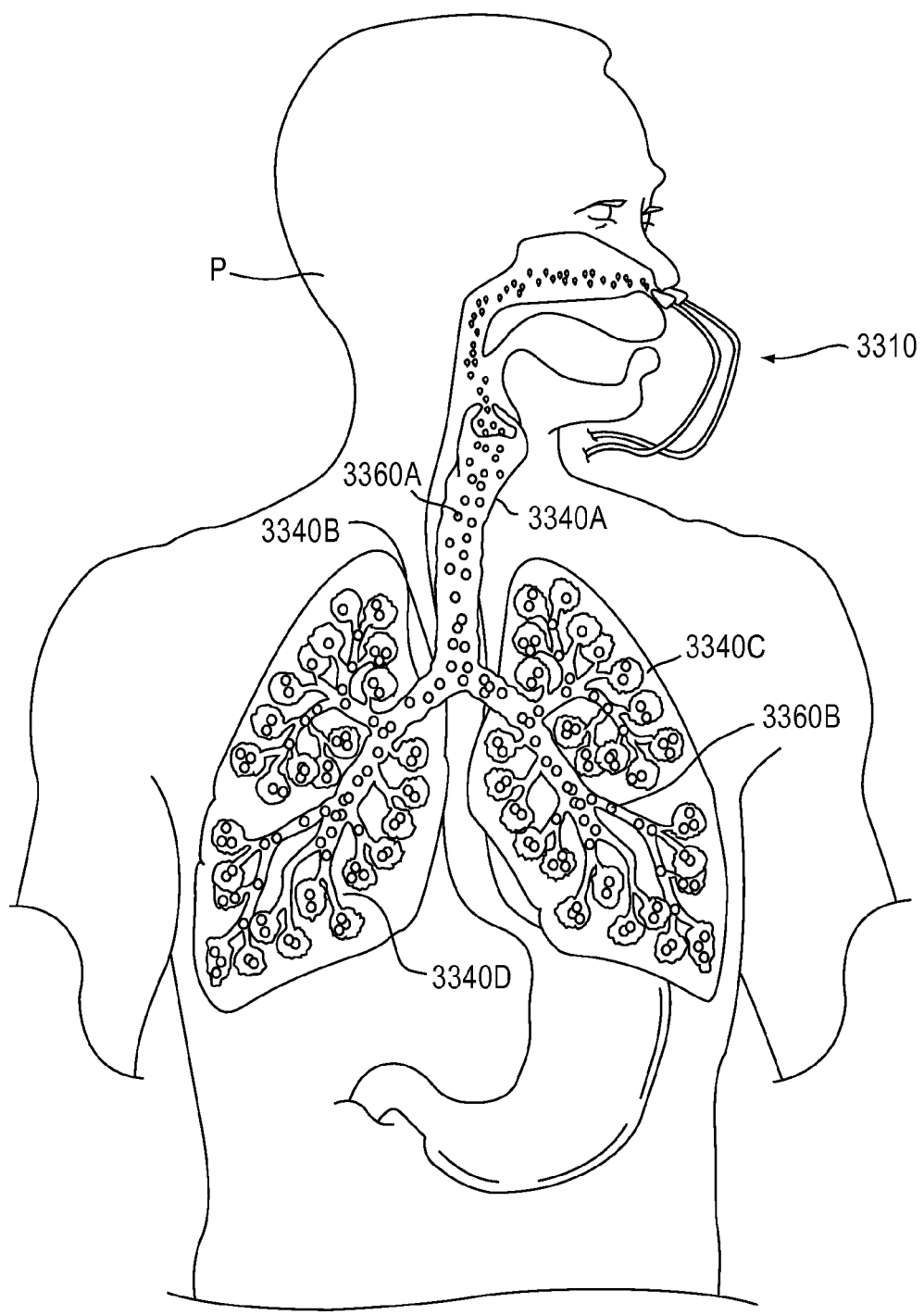
FIG. 33 is an illustration of the trans-nasal administration of aerosolized medicines into the lung(s) of a patient, according to some embodiments.

The systems and methods described herein include transnasal delivery of therapeutic compounds into the lower airways. As shown in FIG. 33, the systems described herein can include a nasal cannula assembly 3310 that conveys an aerosol ($A_{DEL}$) into the nares of a patient P. The delivered aerosol $A_{DEL}$ (i.e., out of the nasal cannula) can be characterized by a particle size (e.g., VMD), a flow rate and a concentration of the therapeutic compound. For example, in some embodiments, the particle size (VMD) can be about 0.5 microns, can be about 1 micron, can be about 1.1 microns, can be about 1.2 microns, can be about 1.3 microns, can be about 1.4 microns, can be about 1.5 microns, can be about 1.6 microns, can be about 1.7 microns, can be about 1.8 microns, can be about 1.9 microns, can be about 2 microns, can be about 2.5 microns, and all values in between. In some embodiments, the flow rate can be about 0.1 µl/min, about 0.2 µl/min, about 0.5 µl/min, about 1 µl/min, about 1.5 µl/min, about 2 µl/min, about 2.5 µl/min, about 3 µl/min, about 4 µl/min, about 5 µl/min, about 6 µl/min, about 7 µl/min, about 8 µl/min, about 9 µl/min, about 10 µl/min, and all values in between.

As shown in FIG. 33, as the aerosol particles according to some embodiments are conveyed through the nasal cannula of the patient P for trans-nasal delivery, the natural humidity in the airways (e.g. the airways 3340A-3340D) lungs causes the particles to accumulate water. Water accumulation increases the size and weight of the particles (e.g. see particle 3360A vs. particle 3360B), and can result in efficient penetration of the particle into desired locations within the respiratory tract, enhanced lung deposition, and enhanced absorption. Exhalation of the aerosolized drug is thus avoided and consistent doses of high concentrations of inhaled drugs can be delivered to the patient P. The use of different entrainment gases, the initial mass loading of the drug aerosolized, as well as the nature of the drug itself (e.g. hygroscopic nature) can be balanced to achieve predetermined growth and/or target deposition to specific regions of the respiratory tract.

Examples

Figure 37:
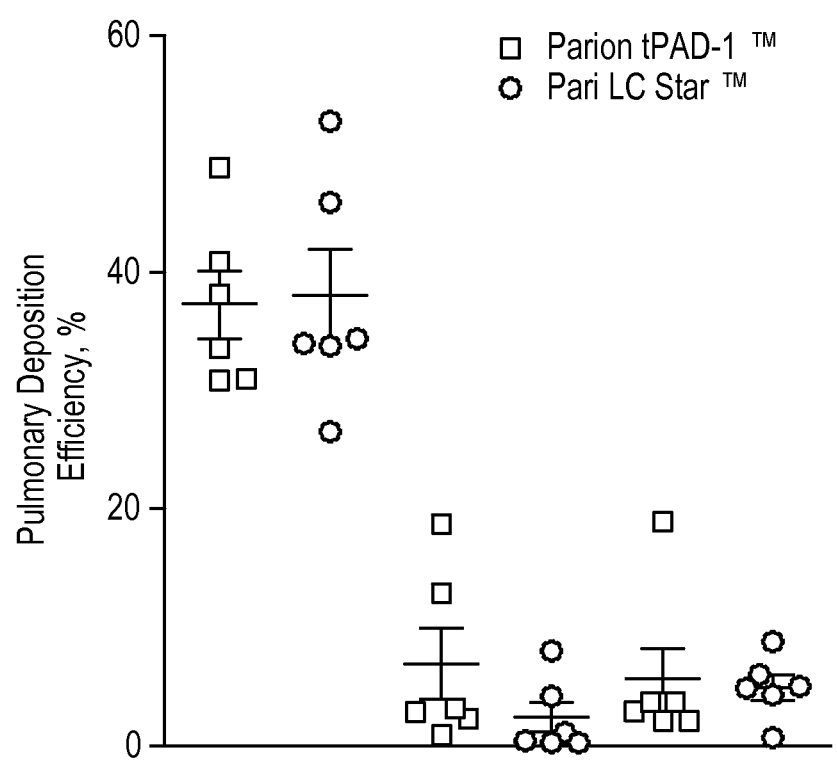
FIG. 37 is a plot illustrating efficiency of pulmonary deposition based on emitted dose and C/P ratios for an aerosol preparation assembly according to an embodiment compared to similar results from a conventional nebulizer.

Performance characteristics of aerosol delivery systems described herein are shown in FIGS. 34A-34B. In FIG. 34A, the particle size of an output of an aerosol delivery system according to embodiments described herein is shown to be generally uniform regardless of the input particle size distribution (Aeroneb™ Pro Nebulizer VMD (µm)). FIG. 34B illustrates the consistency of the aerosol output achieved with five different aerosol source nebulizers. Regardless of the aerosol particle size distribution produced by Aeroneb™ Pro nebulizers currently used, aerosol delivery systems according to some embodiments described herein produce an aerosol emitted from the prongs of the nasal cannula with uniform particle size of the desired range (1.3 to 1.4 µm VMD, FIG. 34A). In terms of aerosol volume emitted from the system (µl/min or µg/min of NaCl with 7% carb-HS), sufficiently uniform output can be achieved via nebulizer screening to support 80% to 120% dose uniformity, as required by the regulators for commercial products (FIG. 34B). FIG. 37 illustrates the efficiency of pulmonary deposition for aerosol delivery systems according to some embodiments (labeled "Parion tPAD-1™") compared to a conventional Pari LC Star™ nebulizer. Embodiments achieved a mean pulmonary deposition fraction (38+/−9%) (% of dose emitted from the nebulizer) that was not different than that of a standard nebulizer (38+/−9%). Head/nasal deposition was only slightly increased with an aerosol delivery system according to embodiments (7+/−7% as compared with 2+/−3%) and the stomach/esophageal activity was not different (5+/−7% as compared with 5+/−3%).

Characterization of the Aerosol from a tPAD-1 Device Used in the Phase 1 Safety, Tolerability and Deposition Efficiency Study:

An aerosol preparation assembly according to an embodiment (also referred to herein as a "tPAD device") was produced to support a deposition study in healthy human subjects. This device was extensively tested before and after dosing of each subject to verify its performance. No problems were identified with the design or the performance of the device during the Phase 1 study with numerous Aerogen Aeroneb Pro nebulizers and tPAD cannulas used.

Due to the variability in nebulizer output for Aeroneb Pro nebs, the commercially distributed nebulizers were screened for output and particles size to achieve 1) similar rates of aerosolization of 7% HS from the tPAD drug reservoir and 2) similar emitted dose from the tPAD device. Regardless of the aerosol particle size distribution produced by Aeroneb Pro nebulizers currently used in the tPAD device, tPAD device produces an aerosol emitted from the prongs of the tPAD nasal cannula with uniform particle size (1.3 to 1.4 µm VMD, FIG. 34A). In terms of aerosol volume emitted from the tPAD device (µl/min or µg/min of NaCl with 7% carb-HS), sufficiently uniform output can be achieved via nebulizer screening to support 80% to 120% dose uniformity (FIG. 34B). The average dose emitted from the prongs of tPAD-1 nasal cannula was 2.2 mg/min of NaCl (or 32 µl/min) with 7% HS (FIG. 34B).

Methodology:

The particle size distribution from the 510K approved and commercially distributed Aerogen Aeroneb Pro nebulizers and from the fully assembled tPAD device was tested via laser diffraction on Sympatec or Spraytec instruments. The aerosol outputs from Aerogen Aeroneb Pro nebulizers were tested gravimetrically. The aerosol output from the fully assembled tPAD device was measured at the prongs of the nasal cannula via direct aerosol filter capture method. The amount of NaCl captured on the filter was measured via HPLC on an ion exchange column for the samples eluted from the filters. Safety, tolerability and deposition efficiency of 7% HS delivered by the tPAD device to healthy human subjects:

Background:

Based on the literature describing pulmonary deposition and theoretical modeling describing pulmonary deposition of trans-nasally delivered aerosols, a goal to achieve 5% pulmonary deposition efficiency was set, as a threshold to advancing the development of the tPAD device in combination with select therapeutic agents. It was reasoned that the tPAD device must be able to achieve a minimum lung dose to show a clinical benefit. For example, for hypertonic saline use in cystic fibrosis, a NaCl dose previously shown to have clinical benefit is ~110 mg of NaCl, deposited in the lungs per oral aerosol administration per subject per day, achieved by Elkins et al. via BID dosing of 7% HS with a Pari LC Plus nebulizer. Larger benefits in $FEV_1$ were achieved with 250 mg of NaCl, deposited in the lungs per subject per day, as achieved by Donaldson et al. via QID dosing of 7% HS with a Pari LC Plus nebulizer trans-orally. The previously published work on transnasally delivery aerosols reported ~1.5% pulmonary deposition efficiency. Thus, the targeted 5% deposition efficiency was a challenging goal. Once the design of the tPAD device was optimized, the pulmonary deposition of HS administered via the tPAD device in healthy human subjects was evaluated.

Figure 35:
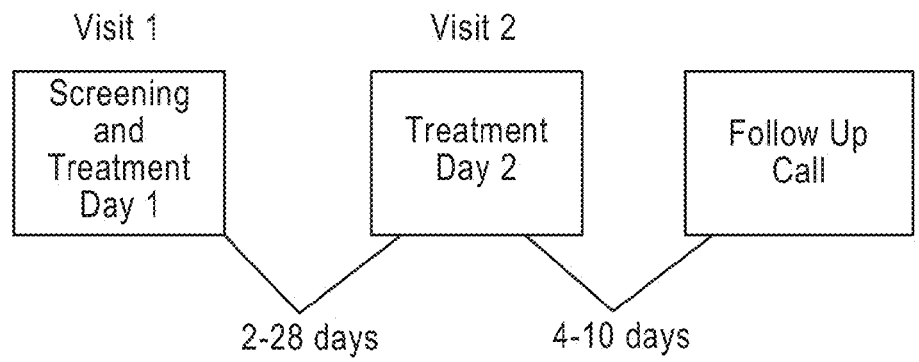
FIG. 35 is a schematic illustration of a Phase 1 Safety, Tolerability and Deposition Efficiency Study Design, according to some embodiments.

Methods and Primary Objective:

Six healthy human subjects (three males and three females) were administered radiolabeled 7% HS ($^{99m}$Tc-DTPA) for a period of 15 min via the tPAD device vs. via the Pari LC Star in an open-label crossover study (FIG. 35). The primary objective of the study was to quantitatively evaluate the efficiency of pulmonary deposition of 7% HS labeled with $^{99m}$Tc-DTPA, based on the aerosol emitted from the prongs of the nasal cannula for the tPAD device vs. from the oral mouthpiece of the LC Star.

The study was conducted under an Investigational Device Exemption (IDE) and the protocol was approved by the University of North Carolina Chapel Hill IRB. Written informed consent was obtained from all participants in the study. All subjects were >18 years of age, received a medical exam prior to beginning the study, had normal $FEV_1$ values (>90% of predicted values), and were free of respiratory tract infection for 4 weeks prior to the study enrollment and without evidence of active rhinosinusoidal disease.

The tPAD device, with a set of Aeroneb Pro nebulizers representative of average output and particle size for these commercial nebulizers produced an average output from the prongs of the cannula of 32 µl/min of aerosol or ~0.47 ml in 15 min. Prior to the first deposition study, spirometry testing was performed and a transmission scan, using a planar $^{57}$Co source, was used to outline lung boundaries and define central/peripheral pulmonary regions of interest. We delivered to each subject 7% HS containing $^{99m}$Tc-DTPA, as a radiotracer to quantitate via external radiation counting of deposited aerosol, for 15 minutes with each delivery device during separate study visits according to established methods. The specific activity of the isotope used was adjusted to achieve a similar deposited lung activity after 15 min of nebulization, given the predicted differences in device output (~0.1 mCi/ml for Pari LC Star and 0.4 mCi/ml for tPAD device). Exhaled aerosols were captured by filter systems uniquely designed for both nebulizer systems to minimize exposure to the volunteers and prevent re-inhalation of aerosols that could confound the interpretation of the data. To acclimatize the subject to the exhalation filter system prior to dosing the radiotracer, unlabeled 7% HS was administered by the tPAD device for 15 minutes. For both devices, subjects were instructed to use their spontaneous breathing patterns. Before the start of nebulization, tPAD and LC Star devices with fill dose of 7% HS (containing $^{99m}$Tc-DTPA) were imaged via a gamma (radiation counting) camera to allow mass balance calculation. Immediately after 15 minutes of 7% HS ($^{99m}$Tc-DTPA) inhalation, an initial radio-aerosol deposition scan was acquired and continuous 1 minute images were recorded for the next 30 minutes. Post-dose spirometry testing was performed after radio-aerosol deposition scans were completed. At the end of the study, the device with residual dose, and the exhalation filter system used with the tPAD device were imaged to allow emitted dose and mass balance calculation.

Analyses:

Lung deposition efficiency (%) was calculated by measuring the radioactivity deposited in the lung and based on the emitted dose. Correction factors were applied to account for signal attenuation differences between the nose and lungs, and lung/nasal clearance. The emitted dose was based on the mass balance of radiolabel deposited 1) within the subject, 2) in the mask or 3) in the exhalation filter. Pulmonary deposition efficiency was then calculated as: deposited dose/emitted volume×100%. Extrathoracic deposition (head region, stomach) was assessed similarly. Aerosol distribution between the central and peripheral airways in the lung was assessed by calculating the central:peripheral deposition fraction (C/P ratio).

Results (Safety):

Six healthy human subjects were dosed with 7% HS ($^{99m}$Tc-DTPA) delivered by the tPAD device and the Pari LC Star. An interim summary of the demographic characteristics for four of the six subjects is provided in Table 4.

TABLE 4

Baseline Demographic Characteristics of Study Participants

| | Subject 1 | Subject 2 | Subject 3 | Subject 4 | Average |
|---|---|---|---|---|---|
| Age (years) | 22 | 19 | 27 | 23 | 22.8 |
| Sex | M | F | M | F | 50% M |
| Height (cm) | 182.9 | 160.1 | 184.0 | 157.5 | 171.1 |
| Weight (kg) | 92.1 | 62.7 | 88.0 | 59.0 | 75.5 |
| BMI | 27.5 | 24.5 | 26 | 23.8 | 25.5 |
| Ethnicity | Caucasian | Hispanic | African American | Caucasian | |

No adverse events were reported during the study in the six subjects. The HS administration by the tPAD device was well tolerated during the 30 minutes dosing with 7% HS (15 minute for each unlabeled and radio-labeled HS). No differences in FEV$_1$ were observed between pre-dose and post-dose spirometry measurements for either device with 105.8% and 106% predicted FEV$_1$ baseline values and −0.8% and 1.3% change post-dose for the tPAD and LC Star devices, respectively.

Figure 36:
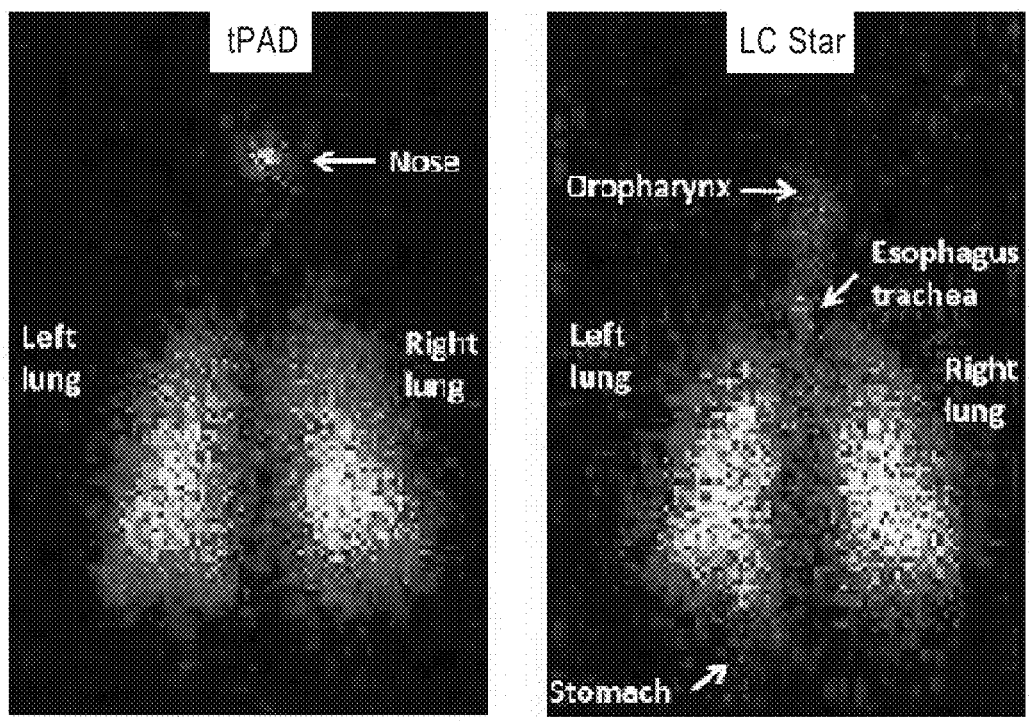
FIG. 36 illustrates deposition patterns from an aerosol preparation assembly according to an embodiment compared to similar results from a conventional nebulizer.

Results (Deposition):

In a marked contrast to previously described 1.5% pulmonary deposition efficiency for trans-nasal aerosols, a high fraction of the dose emitted from the tPAD device was deposited in the lung (38±9%, n=6). The deposition in nasal passages was relatively low and accounted for 7±7% (n=6) of the emitted dose, plus an additional 5±3% (n=6) likely associated with nasal deposition, that was cleared and swallowed prior to initial deposition scan. The tPAD aerosol deposited in a uniform, peripheral airway pattern (FIG. 36), with C/P ratio of 1.06±0.07 (n=6), consistent with the optimal dosing for many lung diseases.

For the Pari LC Star, depositions of 38±9%, 2±3%, 5±3% (n=6), in the lung, oropharynx and esophagus/GI, respectively, based on the emitted dose were observed. Accounting for residual volume left in the LC Star following the completion of 15 minute inhalation, the deposition efficiency based on fill dose was ~18% which is consistent with previously published values. Based on the C/P analysis (C/P ratio of 1.31±0.21 for Pari LC Star, n=6), the Pari LC Star generated more centrally deposited aerosol, which is consistent with the larger aerosol particles produced by the LC Star (3.6 μm VMD).

Surprisingly, the tPAD trans-nasal delivery performed as well as the most refined of oral jet nebulizers i.e. the LC Star. The tPAD device produces almost an order of magnitude more efficient pulmonary deposition than any other known system to administer aerosols trans-nasally. Based on the 38% deposition efficiency, the tPAD device can administer NaCl doses exceeding the designated 250 mg of NaCl that showed clinical benefit in CF per Donaldson et al. For example, the output of 32 μl/min (or 2.2 mg/min with 7% HS), with an "average" Aeroneb Pro nebulizer, would result in a deposited dose of 401 mg of NaCl over 8 hours (2.2 mg/min× 0.38 efficiency×480 min). With "higher-performing" Aeroneb Pro nebulizers, an output of 50 μl/min (or 3.5 mg/min with 7% HS) has been achieved, which would result in a deposited dose of 638 mg. Validated methods to "detune" the performance of the tPAD device to achieve the designated 250 mg dose are readily available (e.g. duty cycle modification for a vibrating mesh nebulizer). Lastly, the observed low nasal deposition was well tolerated in the present study and should be compatible with long term safety and with sleep. In summary, with 30-50 μl/min nasal prong output, 38% deposition efficiency, a desirable peripheral airways deposition pattern in the lung, and favorable safety and tolerability profiles, the tPAD device is able to support trans-nasal administration of therapeutically effective doses of aerosolized therapeutic agents, including overnight HS dosing in CF patients with delivery of therapeutically effective NaCl doses.

As described herein, in some embodiments, a system and/or method of transnasal delivery can produce a deposition efficiency of greater than 3%, greater than 5%, greater than 10%, greater than 15%, greater than 20%, greater than 25%, greater than 30%, greater than 35% and as much as approximately 40%. In some embodiments, a system and/or method of transnasal delivery can produce a deposition efficiency of greater than 40%, greater than 45%, greater than 50%, greater than 55%, greater than 60%, greater than 65%, greater than 70%, greater than 75% and as much as approximately 80%. For example, when a system is run only during the inhalation cycle, a deposition greater than 40% and/or up to about 80% deposition efficiency can be achieved. In another example, when a system is run continuously, a deposition efficiency of up to about 40% can be achieved. In some embodiments, for example, a method can include producing an aerosol of HS having a concentration of 7% and a VMD of approximately 1.4 µm. The method includes delivering, transnasally, the aerosol into the lungs such that a deposition efficiency of approximately 40% is achieved.

Table 5 further illustrates representative values for levels of aerosol output from the prongs of nasal cannula (µl/min) for 7% to 21% hypertonic saline to deposit 250 mg of NaCl into the lung of CF patients over 8 hours for deposition efficiencies ranging from 15% to 40% of the emitted dose. As shown in Table 3, at least 19 µl/min of aerosolized 7% HS emitted from the prongs of nasal cannula is delivered assuming very high 40% depositing of such intranasal aerosol in the lung. Additionally, the method and systems described herein include producing such output consistently and substantially continuously over 8 hours without excessive rainout to deliver the desirable therapeutic dose and be well-tolerated by the patients. By delivering the therapeutic compound at a low rate of deposition over a longer period of time, increased saline concentration can be employed. For example, in some embodiments, a method includes delivering 21% hypertonic saline at a deposition efficiency of 40%, and at an output of 6 µl/min to produce delivery of 250 mg of NaCl into the deep lung of CF patients. If only 50 mg dose of NaCl mass deposited in the lung of patients during eight hour extended aerosol administration would be therapeutically sufficient, with aerosol deposition efficiency of 25% an output of only 2 µl/min of 21% HS aerosol emitted from the prongs of nasal cannula would be needed. For other more potent therapeutic agents, an output of 10-fold or 100-fold lower magnitude (0.2 and 0.02 µl/min respectively) could be sufficient.

TABLE 5

Per Minute Output Required from the Prongs of Nasal Cannula to Deliver 250 mg of NaCl into the Lung with Different HS Concentrations and Under Different Deposition Efficiencies

|  | 7% HS | 10% HS | 12% HS | 14% HS | 21% HS |
| --- | --- | --- | --- | --- | --- |
| 15% deposition | 50 ul/min | 35 ul/min | 29 ul/min | 25 ul/min | 17 ul/min |
| 20% deposition | 37 ul/min | 26 ul/min | 22 ul/min | 19 ul/min | 12 ul/min |
| 25% deposition | 30 ul/min | 21 ul/min | 17 ul/min | 15 ul/min | 10 ul/min |
| 30% deposition | 25 ul/min | 17 ul/min | 14.5 ul/min | 12 ul/min | 8 ul/min |
| 35% deposition | 21 ul/min | 15 ul/min | 12 ul/min | 11 ul/min | 7 ul/min |
| 40% deposition | 19 ul/min | 13 ul/min | 11 ul/min | 9 ul/min | 6 ul/min |

From the rates displayed in Table 5 for aerosolized volumes of NaCl solutions emitted from the prongs of the nasal cannula (ul/min), corresponding rates of NaCl mass emission from the prongs of the cannula can be calculated (NaCl concentration (mg/ul)×aerosol emission rate ul/min). These rates for NaCl mass emission from the prongs of the nasal cannula, required to produce dosing rates in the presumed therapeutic range of 0.52 mg/min of NaCl deposited on the surface of the airways, are displayed in Table 6 as a function of deposition efficiency. Although Table 5 indicates a desired delivery of 250 mg, in other embodiments the desired delivery dose can any suitable value, such as up to 500 mg, up to 700 mg and up to 1000 mg. Such dosing levels can be achieved by any suitable manner described herein, such as, for example, by employing higher saline concentrations and/or higher flow rates.

TABLE 6

Per Minute Output for the Mass of NaCl Emitted from the Prongs of Nasal Cannula and Deposited in the Lung to Deliver 250 mg of NaCl into the Lung

|  | Emitted NaCl Mass mg/min | Deposited NaCl Mass mg/min |
| --- | --- | --- |
| 5% deposition | 10.4 mg/min | 0.52 mg/min |
| 10% deposition | 5.2 mg/min | 0.52 mg/min |
| 15% deposition | 3.5 mg/min | 0.52 mg/min |
| 20% deposition | 2.6 mg/min | 0.52 mg/min |
| 25% deposition | 2.1 mg/min | 0.52 mg/min |
| 30% deposition | 1.7 mg/min | 0.52 mg/min |
| 35% deposition | 1.5 mg/min | 0.52 mg/min |
| 40% deposition | 1.3 mg/min | 0.52 mg/min |

The embodiments disclosed herein also relate to compositions comprising hypertonic saline and/or a pharmaceutically acceptable osmolyte suitable for use in the medicament delivery devices, and in accordance with the methods disclosed herein. Accordingly, the present compositions may be adapted for various administration routes and methods in which such composition(s) are to be employed. For example, in some embodiments, the present compositions may be adapted for transnasal delivery via an aerosol having a particle size distribution as described herein.

Disclosed embodiments unexpectedly addressed previous shortcomings of very low trans-nasal pulmonary deposition efficiency by providing methods, compositions and an apparatus for administering active agents to the lungs of a subject trans-nasally with high pulmonary deposition efficiencies. One embodiment is a method of treating at least one lung/the lungs of a subject in need thereof, comprising: administering an active agent to at least one lung/the lungs of a subject.

In some embodiments, the administering is carried out by aerosol administration. In some embodiments, the administering is carried out by inhalation administration. In some embodiments, the administering is carried out overnight. In some embodiments, the administering is carried out while the subject is sleeping. In some embodiments, the administering is carried out during the day. In some embodiments, the administering is carried out while the subject is awake. In some embodiments, the administering is carried out to a human subject. In some embodiments, the administering is carried out to an animal subject. In some embodiments, the aerosol particle size emitted from the device has 0.5 to 2.5 µm VMD (volume median diameter), with more preferred 1 to 2 µm VMD and most preferred 1.2 to 1.6 µm VMD. In some embodiments, the aerosol particle size distribution is such that there are not more than 10%, 5%, 2.5% and in the most preferred embodiment not more than 1% particles larger than 4 µm based on volume normalized amounts. In some embodiments, the solution can by hypotonic, isotonic or hypertonic. In more preferred embodiments, the solution is hypertonic. In some embodiments, NaCl is used to modulate the tonicity of the solution, so that the overall rate of NaCl deposition is likely below 3 mg/min, 2 mg/min or 1 mg/min of NaCl deposited on the surface of the airway epithelium. In some embodiments, NaCl is used to modulate the tonicity of the solution either alone or with combination(s) with other therapeutic agent(s). In some embodiments, other osmolyte agents such as sodium bicarbonate, mannitol, glucose and others are used to modulate the tonicity of the aerosol solution, either alone or in combination with other therapeutic agent(s). In some embodiments, the osmolyte agent concentration is used to modulate deposition fraction of the aerosol in individual portions of the airways (e.g. large airways vs. small airways vs. alveolar regions). In some embodiments, the higher osmolyte concentration is used to increase central deposition of the aerosol, compared to lower osmolyte concentration leading to more peripheral deposition. In some embodiments, the aerosol administration is conducted for extended periods of time, i.e. 60 min to 8 hours and longer, e.g., about 8 to about 24 hours (by sustained administering, infusion administering, or cyclical administering). In some embodiments, the aerosol administration is conducted for shorter periods of time, i.e. 60 min or shorter as a replacement for aerosol administration via 1) jet, vibrating mesh, vibrating horn and ultrasonic nebulizers; 2) MDIs; and 3) DPIs. In some embodiments, the administration is carried out by trans-nasal administration of the aerosol. For example, the aerosol administration can be carried out over a period of more than about 1 hour, or up to about 4 hours, or up to about 6 hours, or up to about 8 hours, or up to about 10 hours, or up to 12 hours, or up to 14 hours, or up to 16 hours, or up to 18 hours, or up to 20 hours, or up to 22 hours, or up to 24 hours, and the aerosol may be administered once each day or multiple times each day if possible. In some embodiments, a first dose can be a priming dose that delivers a higher dosage, while subsequent doses deliver lower dosages of the osmolyte agent.

In some embodiments, the composition can include both an osmoyte (saline) and another active ingredient (e.g., albuterol). In accordance with the systems and methods described herein, the composition can be formulated and the system can be configured to produce a desired aerosol particle size such that the active ingredient is delivered to a specific portion of the airway. For example, in some embodiments, the osmolyte can be selected having a desired tonicity and the aerosol delivery system can be selected to produce a particle size to cooperatively deliver the active ingredient into a portion of the airway of interest (e.g., the lower airway, the upper airway or the like).

Active Agents and Diseases Treatable by Therapies Administered by Tpad-Based Devices As used herein, a "tPAD" device refers to aerosol delivery systems according to disclosed embodiments, such as those illustrated in FIG. 1.

Disclosed embodiments of the invention contemplate a variety of medicaments that can be delivered as aerosols to the lungs. Such medicaments may 1) act locally in the lung to elicit a local therapeutic effect or 2) they may result in systemic exposure by crossing into the pulmonary and systemic circulations and eliciting therapeutic effects in different compartments (see Table 7).

TABLE 7 tPAD Platform Use: Duration of Administration via tPAD-based Devices vs. Target Site of Therapeutic Intervention

| Duration of Administration vs. Target Site of Therapeutic Intervention | Extended Aerosol Administration (60 min to 8 hours per day and longer) | Short Aerosol Administration (60 min per dose and shorter) |
|---|---|---|
| Pulmonary tissue | Most preferred | More preferred |
| Extra-pulmonary tissue | Preferred | Preferred |

Suitable therapeutic agents administered by the tPAD-based devices and diseases and disorders treatable with these agents are listed below:

Exemplary agents targeting pulmonary tissue are listed below in "Drug Classes Suitable for Administration via tPAD-based Devices Targeting Pulmonary Tissues."

Exemplary agents targeting extra-pulmonary tissue are listed below in "Drug Classes Suitable for Administration via tPAD-based Devices Targeting Extra-pulmonary Tissues." Only such agents that can be formulated to reach therapeutically effective levels in the extra-pulmonary tissues of interest are suitable.

All other classes of therapeutic agents, suitable for use either in pulmonary or extra-pulmonary space, are listed below in "All Other Drug Classes Suitable for Administration via tPAD-based Devices for Local or Systemic Administration."

Diseases and conditions that can be treated by therapeutic agents administered via tPAD-based devices by either locally acting (i.e. in the lung and nasal passages) or systemically acting (i.e. all extra-pulmonary compartments) is provided in "List of Diseases and Conditions Treated by Therapies Administered by the tPAD-based Devices."

Drug Classes Suitable for Administration Via Tpad-Based Devices Targeting Pulmonary Tissue.

These agents include but are not limited to agents that (i) enhance or facilitate mucus clearance; (ii) have antimicrobial activity; (iii) have anti-inflammatory activity; (iv) or have bronchodilator activity; and (v) all other agents currently administered by inhalation via nebulizers, MDIs and DPIs. For agents with undesirable safety or tolerability properties due to high local or systemic concentration following bolus administration via nebulizer, administration by inhalation over the course of 8 to 24 hours or overnight to a patient via nasal cannula may improve the therapeutic index for such agents.

Exemplary Agents that Facilitate Mucus Clearance

Adequate mucus clearance (MC) is a crucial factor in the maintenance of normal airway health, is dependent on mucus rheology, airway hydration, and ciliary beat frequency (CBF). Abnormal mucus clearance is an important contributor to the phenotype of patients with chronic bronchitis due to environmental or genetic causes. Normal mucus clearance requires 1) adequate hydration of the airway surface and 2) an absence of strong adhesive interaction between the mucus and cell surface. Hydration is formally defined by the concentrations of mucins in the periciliary and mucus layers. Ion transport properties regulate the amount of salt and water (i.e. the solvent) and goblet cells and glands control the concentration of mucins on the airway surface. Both cystic fibrosis (CF) patients and subjects with chronic bronchitis associated with cigarette smoke exposure, i.e., COPD (Chronic Obstructive Pulmonary Disease), exhibit increases in mucus concentration as quantified by % solids, as a result of reduced airway hydration and mucin hypersecretion, consequent to goblet cell and glandular hyperplasia. Both as a function of disease severity, and in acute exacerbations, raised mucin/mucus concentrations produce adherent mucus that sticks to epithelial cells, initiates inflammatory responses and airway wall injury, and serves as a growth medium for pathogenic microorganisms (Boucher, R. C., "New concepts of the pathogenesis of cystic fibrosis lung disease", European Respiratory Journal 23(1):146-158 (2004) and Matsui, H., Grubb, B. R., Tarran, R., Randell, S. H., Gatzy, J. T., Davis, C. W., and Boucher, R. C. "Evidence for periciliary liquid layer depletion, not abnormal ion composition, in the pathogenesis of cystic fibrosis airways disease", Cell 95:1005-1015 (1998) and Matsui, H., Wagner, V. E., Hill, D. B., Schwab, U. E., Rogers, T. D., Button, B., Taylor, R. M., 2nd, Superfine, R., Rubinstein, M., Iglewski, B. H., et al., "A physical linkage between cystic fibrosis airway surface dehydration and *Pseudomonas aeruginosa* biofilms", Proc. Natl. Acad. Sci. USA 103:18131-18136 (2006)).

Osmolytes

Active compounds may be ionic osmolytes (i.e., salts), or may be non-ionic osmolytes (i.e., sugars, sugar alcohols, and organic osmolytes). It is to be noted that all racemates, enantiomers, diastereomers, tautomers, polymorphs and pseudopolymorphs and mixtures of the osmotically active compounds are suitable for use with disclosed embodiments.

Active osmolytes useful in the disclosed embodiments that are ionic osmolytes include any salt of a pharmaceutically acceptable anion and a pharmaceutically acceptable cation. Preferably, either (or both) of the anion and cation are non-absorbable (i.e., osmotically active and not subject to rapid active transport) in relation to the airway surfaces to which they are administered. Such compounds include but are not limited to anions and cations that are contained in FDA approved commercially marketed salts, see, e.g., Remington: The Science and Practice of Pharmacy, Vol. II, pg. 1457 (19.sup.th Ed. 1995), incorporated herein by reference, and can be used in any combination including their conventional combinations.

Pharmaceutically acceptable osmotically active anions that can be used to implement the disclosed embodiments include, but are not limited to, acetate, benzenesulfonate, benzoate, bicarbonate, bitartrate, bromide, edetate, camsylate (camphorsulfonate), carbonate, chloride, citrate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-di(dehydroabietyl)ethylenediamine), hydroxynaphthoate, iodide, isethionate, lactate, lactobionate, malate, maleate, mandelate, mesylate, methylnitrate, methylsulfate, mucate, napsylate, nitrate, nitrite, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Particularly preferred anions include chloride, sulfate, nitrate, gluconate, iodide, bicarbonate, bromide, and phosphate.

Pharmaceutically acceptable cations that can be used to implement the disclosed embodiments include, but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like. Particularly preferred organic cations are 3-carbon, 4-carbon, 5-carbon and 6-carbon organic cations. Metallic cations useful in the practice of the disclosed embodiments include but are not limited to aluminum, calcium, lithium, magnesium, potassium, sodium, zinc, iron, ammonium, and the like. Particularly preferred cations include sodium, potassium, choline, lithium, meglumine, D-lysine, ammonium, magnesium, and calcium.

Specific examples of osmotically active salts that may be used with the sodium channel blockers described herein to carry out the disclosed embodiments include, but are not limited to, sodium chloride, potassium chloride, choline chloride, choline iodide, lithium chloride, meglumine chloride, L-lysine chloride, D-lysine chloride, (usually seen as the HCl salt) ammonium chloride, potassium sulfate, potassium nitrate, potassium gluconate, potassium iodide, ferric chloride, ferrous chloride, potassium bromide, etc. Either a single salt or a combination of different osmotically active salts may be used to carry out the disclosed embodiments. Combinations of different salts are preferred. When different salts are used, one of the anion or cation may be the same among the differing salts.

Osmotically active compounds of the disclosed embodiments also include non-ionic osmolytes such as sugars, sugar-alcohols, and organic osmolytes. Sugars and sugar-alcohols useful in the practice of the disclosed embodiments include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); 6-carbon sugars (e.g., both the D and L forms of altose, allose, glucose, mannose, gulose, idose, galactose, and talose), and the 7-carbon sugars (e.g., both the D and L forms of allo-heptulose, allo-hepulose, gluco-heptulose, manno-heptulose, gulo-heptulose, ido-heptulose, galacto-heptulose, talo-heptulose). Additional sugars useful in the practice of the disclosed embodiments include raffinose, raffinose series oligosaccharides, and stachyose. Both the D and L forms of the reduced form of each sugar/sugar alcohol useful in the disclosed embodiments are also suitable active compounds. For example, glucose, when reduced, becomes sorbitol; within the scope of the invention, sorbitol and other reduced forms of sugar/sugar alcohols (e.g., mannitol, dulcitol, arabitol) are accordingly suitable active compounds.

Suitable osmotically active compounds additionally include the family of non-ionic osmolytes termed "organic osmolytes." The term "organic osmolytes" is generally used to refer to molecules used to control intracellular osmolality in the kidney. See e.g., J. S. Handler et al., Comp. Biochem. Physiol., 117:301-306 (1997); M. Burg, Am. J. Physiol. 268: F983-F996 (1995), each incorporated herein by reference. Although the inventor does not wish to be bound to any particular theory, it appears that these organic osmolytes are useful in controlling extracellular volume on the airway/pulmonary surface. Organic osmolytes useful as active compounds for the disclosed embodiments include but are not limited to three major classes of compounds: polyols (polyhydric alcohols), methylamines, and amino acids. The polyol organic osmolytes considered useful in the practice of the disclosed embodiments include, but are not limited to, inositol, myo-inositol, and sorbitol. The methylamine organic osmolytes useful in the practice of disclosed embodiments include, but are not limited to, choline, betaine, carnitine (L—, D- and DL forms), phosphorylcholine, lyso-phosphorylcholine, glycerophosphorylcholine, creatine, and creatine phosphate. Suitable amino acid organic osmolytes include, but are not limited to, the D- and L-forms of glycine, alanine, glutamine, glutamate, aspartate, proline and taurine. Additional osmolytes useful in the practice of disclosed embodiments include tihulose and sarcosine. Mammalian organic osmolytes are preferred, with human organic osmolytes being most preferred. However, certain organic osmolytes are of bacterial, yeast, and marine animal origin, and these compounds are also useful active compounds for the practice of disclosed embodiments.

Under certain circumstances, an osmolyte precursor may be administered to the subject; accordingly, these compounds are also useful in the practice of the disclosed embodiments. The term "osmolyte precursor" as used herein refers to a compound which is converted into an osmolyte by a metabolic step, either catabolic or anabolic. Suitable osmolyte precursors of this invention include, but are not limited to, glucose, glucose polymers, glycerol, choline, phosphatidylcholine, lyso-phosphatidylcholine and inorganic phosphates, which are precursors of polyols and methylamines. Suitable precursors of amino acid osmolytes include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

In one embodiment, the osmolyte is hypotonic saline, isotonic saline, or hypertonic saline used as the active agent.

The Importance of Buffering Systems for Aerosolized Therapies

Buffering agents contained in pharmaceutical formulations are typically added to maintain the activity or stability of the pharmaceutical product. Furthermore, upon aerosolization and delivery of the aerosol to lung airway surfaces, the buffering agents can maintain the physiological pH of lung airway surfaces. For example, the pH of the airway surface liquid is regulated to values of ~pH 7 to 7.4, and airways host defense in part depends on maintenance of the pH. Buffering agents used in formulations of aerosolized therapies, therefore, may be are useful for 1) preventing acidification of the airway surface occurring with hyperosmolar therapies; 2) normalization of the pH of the airway surface for diseases accompanied or associated or caused by lower than normal airway surface pH; and 3) to prevent or attenuate the drop in the airway surface following administration of aerosols that would otherwise be formulated at pH lower than the airway surface (pH=~7 to 7.4) or causing acidification of the airway surface following deposition in the lung. The use of bicarbonate anion as a buffering agent may be particularly useful, given its natural role as a buffering agent on the airway surface, and its depletion in diseases associated or caused by CFTR dysfunction such as CF and COPD.

The buffering agent can be any compound comprising an anionic component which is able to maintain a pH from about 6.8 to about 7.6. In one embodiment, the anionic component is able to maintain a pH from about 6.9 to about 7.5. In another embodiment, the anionic component is able to maintain a pH from about 7.0 to about 7.4. Examples of the anionic component include, but are not limited to, carbonate ($CO_3^{2-}$) and bicarbonate ($HCO_3^-$). Examples of the buffering agent include, but are not limited to, any alkali metal and alkaline earth metal salt of carbonate and bicarbonate, such as sodium carbonate, sodium bicarbonate, potassium carbonate, potassium bicarbonate, calcium carbonate, calcium bicarbonate, magnesium carbonate, magnesium bicarbonate, lithium carbonate, and lithium bicarbonate.

There are two key considerations that link $HCO_3^-$ as a buffer to CFTR. First, recent findings indicate that, although the relative ratio of $HCO_3^-$ conductance/$Cl^-$ conductance is between 0.1 and 0.2 for single CFTR channels activated with cAMP and ATP, the ratio in the sweat duct can range from virtually 0 to almost 1.0, depending on conditions of stimulation. That is, combining cAMP+cGMP+α-ketoglutarate can yield CFTR $HCO_3^-$ conductance almost equal to that of $Cl^-$ conductance (Quiton et al. Physiology, 22(3):212-225 (2007)). Therefore, CFTR conducts $HCO_3^-$, and hence CF airway surfaces may be $HCO_3^-$ depleted, or acidic, and in need of replacement therapy. Second, absent CFTR-dependent bicarbonate secretion can lead to chronic airway surface acidification and impaired capacity of CF airways to respond to airway conditions associated with acute acidification of airway surface liquid layer e.g. gastric acid inspiration (Coakley et al., *Proc Natl Acad Sci USA*, 100(26):16083-8 (2003)).

Buffering Systems Used as Excipients to Prevent Decrease in Airway Surface pH Consequent to Deposition of Hyperosmolar Solution on Airway Surface Administration of hyperosmolar agents, such as 7% HS, on the airway surface can cause a transient decrease in the pH of the airway surface liquid layer (ASL). This transient decrease in pH may cause additional irritation to the airways. Therefore, it may be beneficial to co-formulate hyperosmolar agents with buffering excipients. This approach is especially relevant for diseases associated with CFTR dysfunction, as CFTR-dependent $HCO_3^-$ conductance contributes significantly to the buffering of the airway surface as described above.

The hyperosmolar agents deposited as aerosols on the airway surface cause a transepithelial efflux of water onto the airway surface. Water added to ambient ASL will rapidly equilibrate with atmospheric $CO_2$ gas [$CO_2(g) \rightarrow CO_2(l)$] which will rapidly form carbonic acid [$CO_2(l)+H_2O(l) \rightarrow H_2CO_3(l)$]. Subsequently, the carbonic acid can lower the pH of the ASL [$H_2CO_3(l) \rightarrow HCO_3^- + H_3O^+$]. To maintain the pH of the ASL, bicarbonate anions can be secreted from the airway epithelial cells via CFTR.

When a hyperosmolar agent is deposited on the airway surfaces at sufficiently high rates, which can cause rapid efflux of water onto the airway surface, the rapid equilibration of $CO_2$ in the ASL and the subsequent ASL acidification can exceed the rate of buffering ion ($HCO_3^-$) secretion from the airway epithelium. Hence, a drop in pH can occur. This phenomenon may be exacerbated in human subjects with decreased CFTR function, such as in CF or COPD patients.

Formulations of hyperosmolar agents with buffering excipients of sufficient buffering capacities can be identified, so that the acidification of the ASL is attenuated or completely prevented. Exemplary buffer systems can comprise, but are not limited to, carbonic acid/carbonate/bicarbonate-based buffers; disodium hydrogen phthalate/sodium dihydrogen orthophosphate-based buffers; tris(hydroxylmethyl)aminomethane/hydrochloric acid-based buffers; barbitone sodium/hydrochloric acid-based buffers; and any combination thereof.

Due to these data, inclusion of bicarbonate anion in the formulation of 7% or >7% hypertonic saline administered by the disclosed methods would be particularly useful. Formulations containing up to 1 to 200 mM concentrations of bicarbonate anions are of particular interest for 7% or >7% HS solutions.

Also contemplated to be useful with disclosed embodiments are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., J. Med. Chem. 19:113-117 (1976); Bodor, N. et al., J. Pharm. Sci. 67:1045-1050 (1978); Bodor, N. et al., J. Med. Chem. 26:313-318 (1983); Bodor, N. et al., J. Pharm. Sci. 75:29-35 (1986), each incorporated herein by reference.

Buffering Systems Used as Excipients to Normalize the Airway Surface pH

CFTR dysfunction leading to airways surface acidification, likely due to the dependence of bicarbonate secretion on CFTR function, has been described in several respiratory diseases including CF and COPD. CF airways surface liquid (ASL) has been shown to be more acidic, compared to the ASL from healthy subjects (Coakley et al., *Proc Natl Acad Sci USA*, 100(26):16083-8 (2003)). Similar abnormalities may occur in COPD. For this reason, it may be beneficial to co-formulate any therapeutic agent, administered to patients suffering from low airway surface liquid pH, with a buffering reagent/excipient of sufficient strength that would normalize the airway surface liquid pH. This approach is also applicable to diseases with decreased airway surface pH due to other causes than CFTR dysfunction, e.g. inflammation and/or infection.

Buffering Systems Used as Excipients to Prevent Decrease in Airway Surface pH Following Administrations of Acidic Aerosols.

Administration of large volumes of unbuffered aerosols on the airway surface can cause a transient decrease in the pH of the airway surface liquid layer (ASL). This transient decrease in pH may cause additional irritation to the airways. Therefore, it may be beneficial to co-formulate any aerosolized drug product with buffering excipients, providing sufficient maintenance of the pH of the aerosol in the neutral range and preventing decreases in the pH of the ASL upon aerosol deposition.

The pharmaceutical formulation is aerosolized by an inhalation delivery device for transnasal delivery. The inhalation delivery device is capable of generating an aerosol having particle size suitable for effectively passing the upper respiratory airways, such as the nasal passway. For example, the aerosol particles for inhalation have a volume median diameter (VMD) from about 0.5 μm to about 2.5 μm, or about 1 μm to about 2 μm; or about 1.2 μm to about 1.6 μm. As the aerosol particles contain an active agent, e.g., hypertonic saline, and a buffering agent, the size thereof can grow as they pass through the respiratory airways during inhalation process to become more effectively deposited to the lower respiratory airways, such as lung airway surfaces. In one embodiment, the aerosol particle size can grow as much as about 50% to about 150%, or about 70% to about 130%, or about 80% to about 120%, or about 100% from the initial nasal inhalation of the aerosol to the delivery of the aerosol to the lung airway surfaces.

Sodium Channel Blockers

Coordinated ion transport by the airway epithelia directly regulates the hydration level of the mucosal surface. Importantly, sodium absorption through the epithelial sodium channel (ENaC) provides the rate-limiting step in hydration. In human subjects with loss of function, mutation in ENaC have 'wet' airway surfaces and extraordinarily fast mucous clearance (see above) (Kerem et al., N. Engl. J Med. 341(3):156-62 (1999)). Conversely, increased sodium absorption through ENaC has been shown to be the underlying cause of mucous dehydration and the formation of mucous plugs in the lungs of CF patients. Furthermore, transgenic mice that overexpress ENaC in the lungs have dehydrated airway surfaces and reduced/absent mucous clearance that results in death (Hummler et al., Proc. Natl. Acad. Sci. USA 94(21):11710-5 (1997)). As predicted from clinical and experimental data, pharmacological blockade of ENaC conserves liquid on airway surfaces and increases mucus clearance (Hirsh et al., J Pharmacol. Exp. Ther. 325(1):77-88 (2008)). Particular examples include, but are not limited to:

Small Molecule Channel Blockers:

Small molecule ENaC blockers are capable of directly preventing sodium transport through the ENaC channel pore. ENaC blockers that can be administered by the disclosed methods include, but are not limited to, amiloride, benzamil, phenamil, and amiloride analogues as exemplified by U.S. Pat. No. 6,858,614, U.S. Pat. No. 6,858,615, U.S. Pat. No. 6,903,105, U.S. Pat. No. 6,995,160, U.S. Pat. No. 7,026,325, U.S. Pat. No. 7,030,117, U.S. Pat. No. 7,064,129, U.S. Pat. No. 7,186,833, U.S. Pat. No. 7,189,719, U.S. Pat. No. 7,192,958, U.S. Pat. No. 7,192,959, U.S. Pat. No. 7,241,766, U.S. Pat. No. 7,247,636, U.S. Pat. No. 7,247,637, U.S. Pat. No. 7,317,013, U.S. Pat. No. 7,332,496, U.S. Pat. No. 7,345,044, U.S. Pat. No. 7,368,447, U.S. Pat. No. 7,368,450, U.S. Pat. No. 7,368,451, U.S. Pat. No. 7,375,107, U.S. Pat. No. 7,399,766, U.S. Pat. No. 7,410,968, U.S. Pat. No. 7,820,678, U.S. Pat. No. 7,842,697, U.S. Pat. No. 7,868,010, and U.S. Pat. No. 7,875,619.

Protease Inhibitors:

ENaC proteolysis is well described to increase sodium transport through ENaC. Protease inhibitors block the activity of endogenous airway proteases, thereby preventing ENaC cleavage and activation. Protease that cleave ENaC include furin, meprin, matriptase, trypsin, channel associated proteases (CAPs), and neutrophil elastases. Protease inhibitors that can inhibit the proteolytic activity of these proteases that can be administered by the disclosed methods include, but are not limited to, camostat, prostasin, furin, aprotinin, leupeptin, and trypsin inhibitors.

Nucleic Acids and Small Interfering RNAs (siRNA):

Any suitable nucleic acid (or polynucleic acid) can be used to carry out the disclosed embodiments, including but not limited to antisense oligonucleotide, siRNA, miRNA, miRNA mimic, antagomir, ribozyme, aptamer, and decoy oligonucleotide nucleic acids. See, e.g., US Patent Application Publication No. 20100316628. In general, such nucleic acids may be from 17 or 19 nucleotides in length, up to 23, 25 or 27 nucleotides in length, or more.

Any suitable siRNA active agent can be used to carry out the disclosed embodiments. Examples include, but are not limited to, those described in U.S. Pat. No. 7,517,865 and US Patent Applications Nos. 20100215588; 20100316628; 20110008366; and 20110104255. In general, the siRNAs are from 17 or 19 nucleotides in length, up to 23, 25 or 27 nucleotides in length, or more.

Secretagogues

Mutations in the cystic fibrosis (CF) gene result in abnormal ion transport across the respiratory epithelium (Matsui et al., Cell 95:1005-15 (1998)). Excessive absorption of sodium and the inability to secrete chloride by the airway epithelium in patients with CF drives water absorption down an osmotic gradient generated by inappropriate salt absorption, dehydrating airway mucous secretions and reducing the volume of liquid in the PCL. In COPD, cigarette smoke impairs CFTR function, thus creating an acquired phenotype similar to CF.

$P2Y_2$ Receptor Agonists:

Agents that that may be administered by the disclosed methods include a group of $P2Y_2$ agonists. Purinergic (P2Y) receptors are abundant on luminal surface of human bronchial epithelium (HBE) and are known to stimulate Cl⁻ secretion and inhibit Na⁺ absorption (Goralski et al., Curr. Opin. Pharmacol., 10(3):294-9 (2010)).

Native agonists of $P2Y_2$ receptors are susceptible to enzymatic hydrolysis in vivo by a class of extracellular enzymes called ecto-nucleotidases (Lazarowski et al., J Biol. Chem. 279(35):36855-64 (2004)) that are present on human epithelial surfaces. Consequently, these agonists have very short half-lives. Given the enzymatic degradation of native agonists as well as engineered nucleotide-based $P2Y_2$ agonists, ecto-nucleotidase inhibitors such as ebselen can be administered by the disclosed methods in order to prolong half-lives of endogenous (e.g., ATP) or exogenously delivered $P2Y_2$ agonists.

P2Y$_2$ agonists that can be administered by the disclosed methods include P2Y$_2$ receptor agonists such as ATP, UTP, UTP-γ-S and dinucleotide P2Y$_2$ receptor agonists (e.g., denufosol or diquafosol) or a pharmaceutically acceptable salt thereof. The P2Y$_2$ receptor agonist is typically included in an amount effective to stimulate chloride and water secretion by airway surfaces, particularly nasal airway surfaces.

Suitable P2Y$_2$ receptor agonists are described in, but are not limited to, U.S. Pat. No. 6,264,975, U.S. Pat. No. 5,656,256, U.S. Pat. No. 5,292,498, U.S. Pat. No. 6,348,589, U.S. Pat. No. 6,818,629, U.S. Pat. No. 6,977,246, U.S. Pat. No. 7,223,744, U.S. Pat. No. 7,531,525 and U.S. Pat. Application No. 2009/0306009 each of which is incorporated herein by reference.

Activators of Alternative Chloride Channels Such as CaCCs and ClC-2 Class Channels:

CaCCs are broadly expressed in mammalian cells where they are involved in a wide range of physiological functions, including transepithelial fluid secretion, oocyte fertilization, olfactory and sensory signal transduction, smooth muscle contraction, and neuronal and cardiac excitation. Single channel analysis has suggested four or more distinct CaCC subclasses, with a wide range of reported single channel conductances from less than 2 pS in cardiac myocytes to 50 pS in airway epithelial cells.

The consequences of CaCC activation are cell type specific, for example, chloride secretion in epithelial cells, action potential generation in olfactory receptor neurons, smooth muscle contraction, and prevention of polyspermia in oocytes. Although CaCCs were functionally characterized nearly three decades ago, their molecular identity has remained unclear until recently, with potential candidates including bestrophins (BEST1-BEST4) (Sun et al., *Proc. Natl. Acad. Sci. USA* 99:4008-4013 (2002)) and Tsunenari et al., *J Biol. Chem.* 278:41114-41125 (2003), the calcium activated chloride channel ClCA family proteins (Gruber et al., *Genomics* 54:200-214 (1998)) and ClC3 (Huang P et al., "Regulation of human CLC-3 channels by multifunctional Ca2+/calmodulin-dependent protein kinase", JBC 276: 20093-100 (2001)).

Three independent laboratories have identified TMEM16A, also called anoctamin 1, as a strong candidate for a CaCC (Yang Y D et al., "TMEM16A confers receptor-activated calcium-dependent chloride conductance", *Nature* 455: 1210-15 (2008); Caputo A et al., "TMEM16A, a membrane protein associated with calcium-dependent chloride channel activity", *Science* 322: 590-4 (2008); Schroeder B C et al., "Expression cloning of TMEM16A as a calcium-activated chloride channel subunit", *Cell* 134:1019-29 (2008)).

ClC2 is a ubiquitously expressed, inwardly rectifying chloride channel that is activated by cell swelling. Suitable alternative chloride channel activators are described in U.S. Pat. Nos. 6,015,828, 6,159,969 and 7,253,295.

Modulators of CFTR Activity:

The hereditary lethal disease CF is caused by mutations in the gene encoding CFTR protein, a cAMP activated chloride channel expressed in the airway epithelia. Various mutations in CFTR cause ion transport dysfunction by limiting the chloride ion secretion to the surface of the airway epithelium via CFTR and by dys-regulation of sodium ion absorption, leading to excessive absorption of sodium cations. These defects in ion transport result in impaired hydration of airway surface liquid layer, decrease in mucus clearance and lead to progressive loss of lung function. Recently, it has been shown that CFTR functional defects are present in cigarette smoke exposed tissue, thus implying the role of CFTR dysfunction in COPD.

Over 1500 putative mutations have been described in CFTR, which can be divided into classes according to the molecular mechanism of the genetic defect (Rowe et al., Pulm. Pharmacol. Ther., 23(4):268-78 (2010)). An understanding of the biology of each of these mutations has led to therapeutic strategies based on the particular mutation type. Class I mutations include premature termination codons (PTCs, e.g. nonsense mutations) within the coding region of CFTR. Class II CFTR mutations include F508del CFTR, the most common mutation in humans. Class III and IV CFTR mutations are characterized by full-length CFTR that reaches the cell surface but exhibit reduced ion transport activity owing to abnormal channel gating (Class III, e.g. G551D) or reduced conductivity of the ion channel pore (Class IV, e.g. R117H). Similarly, splicing mutants (Class V) and mutations within the C-terminus (Class VI) are also full length, but exhibit reduced activity owing to reduced numbers of active channels within the plasma membrane. The classification of CFTR mutants can be simplified into the therapeutically relevant groups based on the activity of agents in development.

Potentiators of cell-surface cystic fibrosis transmembrane conductance regulator CFTR mutation classes that result in dysfunctional CFTR that resides at the plasma membrane include Class III, IV, V, and VI mutations and represent potential targets for CFTR activators.

CFTR activity modulating compounds that can be administered by the disclosed methods include, but are not limited to, VX-809, VX-770, VX-661 and compounds described in US 2009/0246137 A1, US 2009/0253736 A1, US 2010/0227888 A1, U.S. Pat. No. 7,645,789, US 2009/0246820 A1, US 2009/0221597 A1, US 2010/0184739 A1, US 2010/0130547 A1, US 2010/0168094 A1, U.S. Pat. No. 7,553,855, U.S. Pat. No. 7,772,259 B2, U.S. Pat. No. 7,405,233 B2, US 2009/0203752, and U.S. Pat. No. 7,499,570.

Mucus/Mucin Modifying Agents

Reducing Agents:

Mucin proteins are organized into high molecular weight polymers via the formation of covalent (disulfide) and non-covalent bonds. Disruption of the covalent bonds with reducing agents is a well-established method to reduce the viscoelastic properties of mucus in vitro and is predicted to minimize mucus adhesiveness and improve clearance in vivo. Reducing agents are well known to decrease mucus viscosity in vitro and commonly used as an aid to processing sputum samples (Hirsch, S. R., Zastrow, J. E., and Kory, R. C., "Sputum liquefying agents: a comparative in vitro evaluation", *J. Lab. Clin. Med.* 74:346-353, 1969). Examples of reducing agents include sulfide containing molecules capable of reducing protein disulfide bonds including, but not limited to, N-acetyl cysteine, cystamine, N-acystelyn, carbocysteine, glutathione, dithiothreitol and thioredoxin containing proteins.

Administration of NAC according to the disclosed methods allows an increase in the daily pulmonary dose (to increase efficacy), while decreasing the rate of presentation (to improve tolerability). With administration of NAC via aerosol infusion, the concentration of NAC on the airway surface can be maintained, despite rapid clearance and metabolism. Thus, by the disclosed methods, the duration of action of NAC on the airway surface will be extended. Deposition of NAC on the surface of the lung according to the disclosed methods can achieve this effect at rates of 0.005 mg/min to 5.4 mg/min over extended 8 hour aerosol administration and can allow for improved efficacy of NAC.

Surfactants and Detergents:

Surfactants and detergents are spreading agents shown to decrease mucus viscoelasticity, improving mucus clearability. Examples of surfactants include DPPC, PF, palmitic acid, palmitoyl-oleoylphosphatidylglycerol, surfactant proteins (e.g. SP-A, B, or C), or may be animal derived (e.g. from cow or calf lung lavage or extracted from minced pig lung) or combinations thereof. See, e.g., U.S. Pat. Nos. 7,897,577; 5,876,970; 5,614,216; 5,100,806; and 4,312,860. Examples of surfactant products include Exosurf, Pumactant, KL-4, Venticute, Alveofact, Curosurf, Infasurf, and Survanta. Examples of detergents include, but are not limited to, Tween-80 and triton-X 100. Surfactants may be used to clear adherent secretions from the lung and/or prevent apposion of upper airway surfaces that produce obstructive sleep apnea.

Buffering Agents to Increase the Activity of Reducing Agents.

Thiol containing agents, such as N-acetylcysteine, exhibit increased reducing activity as the pH environment approaches or exceeds the $pK_a$ of the sulfur moiety. The pH of the airway surface is maintained at ~7.4 and is reported be more acidic in diseased airways such as CF (Jayaraman S, Song Y, Vetrivel L, Shankar L, Verkman A S," Noninvasive in vivo fluorescence measurement of airway-surface liquid depth, salt concentration, and pH", J Clin. Invest., 107(3): 317-24 (2001)). As the $pK_a$ of the NAC sulfur moiety is 9.5, NAC is only partially active in the pH environment of the lung surface. Thus, NAC administered (by the disclosed methods) in combination with sufficient amounts of a buffering agent to raise the ASL pH, will increase the therapeutic potential of NAC.

Expectorants:

Any suitable expectorant can be used, including but not limited to guaifenesin (see, e.g., U.S. Pat. No. 7,345,051).

DNase:

Any suitable deoxyribonuclease can be used, including but not limited to Dornase Alpha (see, e.g., U.S. Pat. No. 7,482,024).

Exemplary Anti-Infective Agents

Chronic obstructive pulmonary diseases are accompanied by both acute and chronic bacterial infections. Both acute and chronic infections lead to chronic inflammation that has acute flare-ups in the form of pulmonary exacerbations. The underlying inflammation is treated with a variety of inhaled anti-inflammatory agents. For example, in cystic fibrosis the most common bacteria causing chronic infection is *Pseudomonas aeruginosa* (*P. aeruginosa*) and antibiotics that are effective against this bacteria are a major component of treatment (Flume, Am. J. Respir. Crit. Care Med. 176(10):957-69 (2007)). Also bacteria such as *Staphylococcus aureus* (*S. aureus*), *Burkholderia cepacia* (*B. cepacia*) and other gram negative organisms as well as anaerobes are isolated from respiratory secretions and people with CF may benefit from treatment of these pathogens to maintain their lung health. Anaerobic bacteria are also recognized as a feature of CF airways, sinuses in subjects with chronic sinusitis, and likely airways of subjects with COPD. Similarly, aspirations or microaspirations, especially in the elderly population and during sleep, are associated with a chemical pneumonitis, anaerobic infections and subsequent bronchiectasis. An ideal treatment of aspiration-related pneumonitis and anaerobic infection would be an immediate treatment. As such, antibiotics are used to eradicate early infections, during pulmonary exacerbations and as chronic suppressive therapy.

The primary measure of antibiotic activity is the minimum inhibitory concentration (MIC). The MIC is the lowest concentration of an antibiotic that completely inhibits the growth of a microorganism in vitro. While the MIC is a good indicator of the potency of an antibiotic, it indicates nothing about the time course of antimicrobial activity. PK parameters quantify the lung tissue level time course of an antibiotic. The three pharmacokinetic parameters that are most important for evaluating antibiotic efficacy are the peak tissue level (Cmax), the trough level (Cmin), and the Area Under the tissue concentration time Curve (AUC). While these parameters quantify the tissue level time course, they do not describe the killing activity of an antibiotic.

Integrating the PK parameters with the MIC gives us three PK/PD parameters which quantify the activity of an antibiotic: the Peak/MIC ratio, the T>MIC, and the 24 h-AUC/MIC ratio. The Peak/MIC ratio is simply the Cpmax divided by the MIC. The T>MIC (time above MIC) is the percentage of a dosage interval in which the serum level exceeds the MIC. The 24 h-AUC/MIC ratio is determined by dividing the 24-hour-AUC by the MIC. The three pharmacodynamic properties of antibiotics that best describe killing activity are time-dependence, concentration-dependence, and persistent effects. The rate of killing is determined by either the length of time necessary to kill (time-dependent), or the effect of increasing concentrations (concentration-dependent). Persistent effects include the Post-Antibiotic Effect (PAE). PAE is the persistent suppression of bacterial growth following antibiotic exposure.

Using these parameters, antibiotics can be divided into 3 categories (see Table 8):

TABLE 8

Categories of Antibodies

| Pattern of Activity | Antibiotics | Goal of Therapy | PK/PD Parameter |
|---|---|---|---|
| Type I Concentration-dependent killing and Prolonged persistent effects | Aminoglycosides Daptomycin Fluoroquinolones Ketolides | Maximize concentrations | 24 h-AUC/MIC Peak/MIC |
| Type II Time-dependent killing and Minimal persistent effects | Carbapenems Cephalosporins Erythromycin Linezolid Penicillins | Maximize duration of exposure | T > MIC |
| Type III Time-dependent killing and Moderate to prolonged persistent effects. | Azithromycin Clindamycin Oxazolidinones Tetracyclines Vancomycin | Maximize amount of drug | 24 h-AUC/MIC |

For Type I antibiotics (aminoglycosides (AG's), fluoroquinolones, daptomycin and the ketolides), the ideal dosing regimen would maximize concentration, because the higher the concentration, the more extensive and the faster is the degree of killing. Therefore, the 24 h-AUC/MIC ratio, and the Peak/MIC ratio are important predictors of antibiotic efficacy. For aminoglycosides, it is best to have a Peak/MIC ratio of at least 8-10 to prevent resistance. For fluoroquinolones vs gram negative bacteria, the optimal 24 h-AUC/MIC ratio is approximately 125. Versus gram positives, 40 appears to be optimal. However, the ideal 24 h-AUC/MIC ratio for fluoroquinolones varies widely in the literature.

Type II antibiotics (beta-lactams, cephalosporins, clindamycin, erythromcyin, carbapenems and linezolid) demonstrate the complete opposite properties. The ideal dosing regimen for these antibiotics maximizes the duration of exposure. The T>MIC is the parameter that best correlates with efficacy. For beta-lactams and erythromycin, maximum killing is seen when the time above MIC is at least 70% of the dosing interval.

Type III antibiotics (oxazolidinones, vancomycin, tetracyclines, azithromycin, clindamycin and the dalfopristin-quinupristin combination) have mixed properties, they have time-dependent killing and moderate persistent effects. The ideal dosing regimen for these antibiotics maximizes the amount of drug received. Therefore, the 24 h-AUC/MIC ratio is the parameter that correlates with efficacy. For vancomycin, a 24 h-AUC/MIC ratio of at least 125 is necessary.

Given the pharmacokinetic and pharmacodynamic properties for Type II and Type III antibiotics, administration by aerosol "infusion" will improve the efficacy for such agents. For example, carbapenam antibiotics are susceptible to enzymatic hydrolysis in vivo by the enzyme dehydropeptidase-I, thus leading to a short elimination half-life (less than 2 hr). The best measure of efficacy of this class of antibiotics is based on the minimum percentage of time the drug concentration is above the minimum inhibitory concentration (MIC) in the target tissue. Most dose regimens target a time above the MIC (TaM) of at least 50%, thus the need for a continuous infusion. High systemic concentrations of carbapenems can have proconvulsive effects and renal and liver toxicity.

Delivering carbapenems via continuous aerosol to the lungs of patients in need can allow for a safe and convenient way to maintain a high TaM in the lungs while reducing potential for systemic side effects. 500 mg to 2,000 mg of inhaled meropenem administered BID in 4 ml of normal saline via Pari LC jet nebulizers may be used for treatment of CF bacterial infections. Such administrations occur at a rate of 6.7 mg/min to 26.7 mg/min of meropenem deposited in the airway surface during two 15 minute nebulization periods per day. A 20 mg to 1,200 mg dose of meropenem, deposited in the lung of CF patients per day and administered at a rate between 0.04 mg/min to 2.5 mg/min of meropenem deposited in the airway surface during 8 hour or longer extended aerosol administration according to the disclosed methods, can allow for better combined safety, tolerability and efficacy outcomes. Patients including, but not limited to, CF, COPD, non-CF bronchiectasis, aspiration pneumonia, asthma and VAP patients suffering from respiratory infection caused by bacteria susceptible to meropenem may benefit from such treatment. Examples of carbapenam antibiotics are: imipenam, panipenam, meropenam, doripenem, biapenam, MK-826, DA-1131, ER-35786, lenapenam, S-4661, CS-834 (prodrug of R-95867), KR-21056 (prodrug of KR-21012), L-084 (prodrug of LJC 11036) and CXA-101.

Delivering class III antibiotics via continuous aerosol to the lungs of patients in need can allow for a safe and convenient way to maintain a high 24 h-AUC/MIC in the lungs while reducing potential for systemic side effects. For example, 20 to 1,200 mg of vancomycin deposited in the lung of patients per day and administered at a rate between 0.04 mg/min to 2.5 mg/min of vancomycin deposited on the airway surface during 8 hour or longer extended aerosol administration according to disclosed methods, can allow for better combined safety, tolerability and efficacy outcomes compared to rapid inhaled delivery or IV infusion. Patients including, but not limited to, CF, COPD, asthma, VAP, HAP, CAP patients and other patients suffering from respiratory infection caused by bacteria susceptible to vancomycin may benefit from such treatment.

The doses and rates for additional antibiotic agents benefiting from administration via aerosol inhalation over extended periods of time according to the disclosed methods are listed in Table 9 below. The rates of deposition of these antibiotic agents were optimized to maintain concentrations above MIC values for relevant bacterial strains and other relevant parameters such at time above MIC or 24-hour AUC/MIC where applicable.

TABLE 9

Minimum and Maximum Doses Deposited in the Lung and Minimum and Maximum Rates of Antibiotic Deposition on the Airway Surface via CSD-1 Device

| Antibiotic | Deposited dose in the lung (mg/day) | CSD-1 rate of deposition (8 hours per day, mg/min) | CSD-1 rate of deposition normalized per constant 10 ml ASL volume (8 hours per day normalized per ASL volume: g/L ASL/hour) | CSD-1 rate of deposition normalized per constant 10 ml ASL volume (8 hours per day normalized per ASL volume: Mol/L ASL/Hour) |
|---|---|---|---|---|
| Vancomycin | 1200 | 2.50 | 15.00 | 1.01E−02 |
|  | 20 | 0.04 | 0.25 | 1.68E−04 |
| Meropenem | 1200 | 2.50 | 15.00 | 3.43E−02 |
|  | 20 | 0.04 | 0.25 | 5.71E−04 |
| Ertapenem | 200 | 0.42 | 2.50 | 5.26E−03 |
|  | 5 | 0.01 | 0.06 | 1.32E−04 |
| Doripenem | 300 | 0.63 | 3.75 | 8.93E−03 |
|  | 20 | 0.04 | 0.25 | 5.95E−04 |
| Imipenem | 800 | 1.67 | 10.00 | 3.15E−02 |
|  | 20 | 0.04 | 0.25 | 7.89E−04 |
| Linezolid | 360 | 0.75 | 4.50 | 1.34E−02 |
|  | 5 | 0.01 | 0.06 | 1.85E−04 |

Exemplary Anti-Inflammatory Agents

Inhaled corticosteroids are the standard of chronic care for asthma, COPD and other respiratory diseases characterized by acute and chronic inflammation leading to airflow limitation. Examples of corticosteroids suitable for administration by the disclosed methods include, but are not limited to, beclomethasone, budesonide, and fluticasone. NSAIDs are a group of anti-inflammatory medications that do not contain steroids. NSAIDs do not carry the same risk of side effects as steroidal anti-inflammatory medications, but with long-term use, they may cause internal bleeding or kidney problems.

Products of arachidonic acid metabolism, specifically the leukotrienes (LTs), contribute to pulmonary inflammation.

Cysteinylleukotrienes (LTC4, LTD4, and LTE4) are produced predominantly by eosinophils, mast cells, and macrophages. Examples of leukotriene modifiers suitable for administration by the disclosed methods include, but are not limited to, monteleukastzileuton and zafirlukast.

Mast cell stabilizers are cromone medications such as cromolyn (sodium cromoglycate) used to prevent or control certain allergic disorders. They block a calcium channel essential for mast cell degranulation, stabilizing the cell and thereby preventing the release of histamine and related mediators. As inhalers they are used to treat asthma, as nasal sprays to treat hay fever (allergic rhinitis) and as eye drops for allergic conjunctivitis. Finally, in oral form they are used to treat the rare condition of mastocytosis.

PDE4 inhibitors have been shown to modulate pulmonary inflammation and used for treatment of chronic obstructive pulmonary diseases. Examples of PDE4 inhibitors suitable for administration by the disclosed methods include, but are not limited to, theophylline and roflumilast.

Exemplary Bronchodilators

NO, NO Donors, NO and Peroxynitrite Scavengers and Inducible NO Synthase Activity Modulators Nitric oxide (NO) is a potent endogenous vasodilator and bronchodilator that can be exogenously administered via inhalation. It is synthesized by the conversion of the terminal guanidine nitrogen atom of L-arginine via the endothelial cell calcium dependent enzyme nitric oxide synthetase and then diffuses across the cell membrane to activate the enzyme guanylatecyclase. This enzyme enhances the synthesis of cyclic guanosine monophosphate (cGMP), causing relaxation of vascular and bronchial smooth muscle and vasodilation of blood vessels (Palmer, Circ. Res., 82(8):852-61 (1998)).

Nitric oxide synthesised in endothelial cells that line blood vessels has a wide range of functions that are vital for maintaining healthy respiratory and cardiovascular systems (Megson, I L et al., Expert Opin. Investig. Drugs 11(5):587-601 (2002)). Reduced nitric oxide availability is implicated in the initiation and progression of many diseases and delivery of supplementary nitric oxide to help prevent disease progression is an attractive therapeutic option. Nitric oxide donor drugs represent a useful means of systemic nitric oxide delivery and organic nitrates have been used for many years as effective therapies for symptomatic relief from angina. However, nitrates have limitations and a number of alternative nitric oxide donor classes have emerged since the discovery that nitric oxide is a crucial biological mediator.

Examples of NO, NO donors and NO synthase activity modulators suitable for administration by the disclosed methods include inhaled NO, inhaled $NaNO_2$, agents disclosed in Vallance et al., Fundam. Clin. Pharmacol., 17(1):1-10 (2003), Al-Sa'doni H H et al., Mini Rev. Med. Chem., 5(3):247-54 (2005), Miller M R et al., Br. J Pharmacol., 151(3):305-21 (2007). Epub 2007 Apr. 2 and Katsumi H et al. Cardiovasc. Hematol. Agents Med. Chem., 5(3):204-8 (2007).

Under certain conditions, inducible NO synthase activity leads to overproduction of NO which in turn increases inflammation and tissue injury. Under these conditions, the following inducible NO synthase inhibitors, NO scavengers and peroxynitrite scavengers administered by the disclosed methods are suitable: Bonnefous et al., *J. Med. Chem.,* 52 (9): 3047-3062 (2009), Muscara et al *AJP—GI* 276 (6):G1313-G1316 (1999) or Hansel et al. *FASEB Journal,* 17:1298-1300 (2003).

Beta 2-Adrenergic Receptor Agonists:

It has been established that administration of super-therapeutic concentrations of receptor agonists leads to receptor desensitization and loss of efficacy. For example, this phenomenon has been described for beta 2-adrenoceptor based bronchodilator agents (Duringer et al., Br. J. Pharmacol., 158(1):169-79 (2009)). High concentration of these receptor agonist agents leads to the receptor phosphorylation, internalization and potential degradation. Administration of receptor agonists, which cause tachyphylaxis following bolus administration via fast nebulizer, by inhalation over the course of 8 to 24 hours or overnight to a patient via nasal cannula improves the efficacy of such agents due to decreased extent of tachyphylaxis. Beta 2-adrenergic receptor agonists include, but are not limited to, albuterol, levalbuterol, salbutamol, procaterol, terbutaline, pirbuterol, and metaproterenol.

Other Exemplary Therapeutic Agents

Examples of other classes of therapeutic agents suitable for administration by the disclosed methods include antivirals such as ribavirin, anti-fungal agents such as amphotericin, intraconazol and voriconazol, immunosuppressants, anti-rejection drugs such as cyclosporine, tacrolimus and sirolimus, bronchodilators including but not limited to anticholinergic agents such as ipratropium, tiotropium, aclidinium and others, PDE5 inhibitors, gene therapy vectors, aptamers, endothelin-receptor antagonists, alpha-1-antitrypsin, prostacyclins, vaccines, PDE-4 and PDE-5 inhibitors and steroids such as beclamethasone, budesonide, ciclesonide, flunisolide, fluticasone, memetasone and triamcinolone.

Drug Classes Suitable for Administration Via Tpad-Based Devices Targeting Extra-Pulmonary Tissues It is well recognized that pulmonary drug delivery is an alternative means to target extra-pulmonary tissues. Systemic administration of therapeutic agents by the tPAD-based devices is useful only in cases when such therapy can be formulated in a manner that allows reaching therapeutically effective levels in the extra-pulmonary tissues of interest.

Pulmonary administration can by-pass issues associated with oral, transdermal, sublingual, IV, i.m., i.p and other injectable drug administration. For example, injection or IV administration cause pain and subjects the individual to infections at the injection site. Furthermore, aerosol delivery of drugs is advantageous to oral administration particularly for therapeutic agents that are poorly orally available or inactivated by first-pass metabolism.

The administration of therapeutic agents intended to target non-pulmonary issues by the disclosed methods is advantageous in that it can (1) overcome the limitations of oral or IV administration; and (2) it can be utilized to control the pharmacokinetic profile (e.g. blood levels over time) of the therapeutic agent.

An example of therapies particularly suitable for administration by the tPAD-based device platform include inhaled insulin for diabetes, inhaled dihydroergotamine for acute migraine, inhaled morphine for palliative care, and sleep agents for dyspnea.

An example of current IV therapies suitable for tPAD-based device administration include inotropic treatments for chronic congestive heart failure [Amrinone (Inocor®), Digitoxin (Crystodigin®), Digoxin (Lanoxin®, Lanoxicaps®), Dobutamine(Dobutrex®) or Milrinone (Primacor®)] and others.

All Other Drug Classes Suitable for Administration Via Tpad-Based Devices for Local or Systemic Administration Other drug classes and agents suitable for administration via TPAD-Based devices for local or systemic administration include but are not limited to 5-alpha-reductase inhibitors, 5-aminosalicylates, 5HT3 receptor antagonists, adamantane antivirals, adrenal cortical steroids, adrenal corticosteroid inhibitors, adrenergic bronchodilators, agents for hypertensive emergencies, agents for pulmonary hypertension, aldosterone receptor antagonists, alkylating agents, alpha-glucosidase inhibitors, alternative medicines, amebicides, aminoglycosides, aminopenicillins, aminosalicylates, amylin analogs, analgesic combinations, analgesics, androgens and anabolic steroids, angiotensin converting enzyme inhibitors, angiotensin II inhibitors, anorectal preparations, anorexiants, antacids, anthelmintics, anti-angiogenic ophthalmic agents, anti-CTLA-4 monoclonal antibodies, anti-infectives, antiadrenergic agents, centrally acting antiadrenergic agents, peripherally acting antiandrogens, antianginal agents, antiarrhythmic agents, antiasthmatic combinations, antibiotics/antineoplastics, anticholinergic antiemetics, anticholinergic antiparkinson agents, anticholinergic bronchodilators, anticholinergic chronotropic agents, anticholinergics/antispasmodics, anticoagulants, anticonvulsants, antidepressants, antidiabetic agents, antidiabetic combinations, antidiarrheals, antidiuretic hormones, antidotes, antiemetic/antivertigo agents, antifungals, antigonadotropic agents, antigout agents, antihistamines, antihyperlipidemic agents, antihyperlipidemic combinations, antihypertensive combinations, antihyperuricemic agents, antimalarial agents, antimalarial combinations, antimalarial quinolines, antimetabolites, antimigraine agents, antineoplastic detoxifying agents, antineoplastic interferons, antineoplastics, antiparkinson agents, antiplatelet agents, antipseudomonal penicillins, antipsoriatics, antipsychotics, antirheumatics, antiseptic and germicides, antithyroid agents, antitoxins and antivenins, antituberculosis agents, antituberculosis combinations, antitussives, antiviral agents, antiviral combinations, antiviral interferons, anxiolytics, sedatives, hypnotics, aromatase inhibitors, atypical antipsychotics, azole antifungals, bacterial vaccines, barbiturate anticonvulsants, barbiturates, BCR-ABL tyrosine kinase inhibitors, benzodiazepine anticonvulsants, benzodiazepines, beta-adrenergic blocking agents, beta-lactamase inhibitors, bile acid sequestrants, biologicals, bisphosphonates, bone resorption inhibitors, bronchodilator combinations, bronchodilators, calcineurin inhibitors, calcitonin, calcium channel blocking agents, carbamate anticonvulsants, carbapenems, carbonic anhydrase inhibitor anticonvulsants, carbonic anhydrase inhibitors, cardiac stressing agents, cardioselective beta blockers, cardiovascular agents, catecholamines, CD20 monoclonal antibodies, CD30 monoclonal antibodies, CD33 monoclonal antibodies, CD52 monoclonal antibodies, central nervous system agents, cephalosporins, cerumenolytics, CFTR potentiators and correctors, chelating agents, chemokine receptor antagonist, chloride channel activators, cholesterol absorption inhibitors, cholinergic agonists, cholinergic muscle stimulants, cholinesterase inhibitors, CNS stimulants, coagulation modifiers, colony stimulating factors, contraceptives, corticotropin, coumarins and indandiones, cox-2 inhibitors, decongestants, dermatological agents, diagnostic radiopharmaceuticals, dibenzazepine anticonvulsants, digestive enzymes, dipeptidyl peptidase 4 inhibitors, diuretics, dopaminergic antiparkinsonism agents, drugs used in alcohol dependence, echinocandins, EGFR inhibitors, estrogen receptor antagonists, estrogens, expectorants, factor Xa inhibitors, fatty acid derivative anticonvulsants, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors, gastrointestinal agents, general anesthetics, genitourinary tract agents, GI stimulants, glucocorticoids, glucose elevating agents, glycopeptide antibiotics, glycylcyclines, gonadotropin releasing hormones, gonadotropin-releasing hormone antagonists, gonadotropins, group I antiarrhythmics, group II antiarrhythmics, group III antiarrhythmics, group IV antiarrhythmics, group V antiarrhythmics, growth hormone receptor blockers, growth hormones, *H. pylori* eradication agents, H2 antagonists, hedgehog pathway inhibitors, hematopoietic stem cell mobilizers, heparin antagonists, heparins, HER2 inhibitors, herbal products, histone deacetylase inhibitors, hormones, hormones/antineoplastics, hydantoin anticonvulsants, immune globulins, immunologic agents, immunostimulants, immunosuppressive agents, impotence agents, in vivo diagnostic biologicals, incretin mimetics, inhaled anti-infectives, inhaled corticosteroids, inotropic agents, insulin, insulin-like growth factor, integrase strand transfer inhibitors, interferons, interleukin inhibitors, interleukins, intravenous nutritional products, iodinated contrast media, ionic iodinated contrast media, iron products, ketolides, laxatives, leprostatics, leukotriene modifiers, lincomycin derivatives, local injectable anesthetics, loop diuretics, lung surfactants, lymphatic staining agents, lysosomal enzymes, macrolide derivatives, macrolides, magnetic resonance imaging contrast media, mast cell stabilizers, medical gas, meglitinides, metabolic agents, methylxanthines, mineralocorticoids, minerals and electrolytes, miscellaneous analgesics, miscellaneous antibiotics, miscellaneous anticonvulsants, miscellaneous antidepressants, miscellaneous antidiabetic agents, miscellaneous antiemetics, miscellaneous antifungals, miscellaneous antihyperlipidemic agents, miscellaneous antimalarials, miscellaneous antineoplastics, miscellaneous antiparkinson agents, miscellaneous antipsychotic agents, miscellaneous antituberculosis agents, miscellaneous antivirals, miscellaneous anxiolytics, sedatives and hypnotics, miscellaneous bone resorption inhibitors, miscellaneous cardiovascular agents, miscellaneous central nervous system agents, miscellaneous coagulation modifiers, miscellaneous diuretics, miscellaneous genitourinary tract agents, miscellaneous GI agents, miscellaneous hormones, miscellaneous metabolic agents, miscellaneous ophthalmic agents, miscellaneous otic agents, miscellaneous respiratory agents, miscellaneous sex hormones, miscellaneous vaginal agents, mitotic inhibitors, monoamine oxidase inhibitors, mouth and throat products, mTOR inhibitors, mucolytics, multikinase inhibitors, muscle relaxants, mydriatics, narcotic analgesic combinations, narcotic analgesics, nasal anti-infectives, nasal antihistamines and decongestants, nasal lubricants and irrigations, nasal preparations, nasal steroids, natural penicillins, neuraminidase inhibitors, neuromuscular blocking agents, neuronal potassium channel openers, next generation cephalosporins, nicotinic acid derivatives, NNRTIs, non-cardioselective beta blockers, non-iodinated contrast media, non-ionic iodinated contrast media, non-sulfonylureas, nonsteroidal anti-inflammatory agents, nucleoside reverse transcriptase inhibitors (NRTIs), nutraceutical products, nutritional products, ophthalmic anesthetics, ophthalmic anti-infectives, ophthalmic anti-inflammatory agents, ophthalmic antihistamines and decongestants, ophthalmic glaucoma agents, ophthalmic steroids, ophthalmic steroids with anti-infectives, oral nutritional supplements, other immunostimulants, other immunosuppressants, otic anesthetics, otic anti-infectives, otic preparations, otic steroids, otic steroids with anti-infectives, oxazolidinedione anticonvulsants, parathyroid hormone and analogs, penicillinase resistant penicillins, penicillins, peripheral opioid receptor antagonists, peripheral vasodilators, peripherally acting antiobesity agents, phenothiazine antiemetics, phenothiazine antipsychotics, phenylpiperazine antidepressants, plasma expanders, platelet aggregation inhibitors, platelet-stimulating agents, polyenes, potassiumsparing diuretics, probiotics, progesterone receptor modulators, progestins, prolactin inhibitors, prostaglandin D2 antagonists, protease inhibitors, proton pump inhibitors, psoralens, psychotherapeutic agents, psychotherapeutic combinations, purine nucleosides, pyrrolidine anticonvulsants, quinolones, radiocontrast agents, radiologic adjuncts, radiologic agents, radiologic conjugating agents, radiopharmaceuticals, recombinant human erythropoietins, renin inhibitors, chemotherapies, rifamycin derivatives, salicylates, sclerosing agents, second generation cephalosporins, selective estrogen receptor modulators, selective immunosuppressants, selective phosphodiesterase-4 inhibitors, selective serotonin reuptake inhibitors, serotonin-norepinephrine reuptake inhibitors, serotoninergic neuroenteric modulators, sex hormone combinations, sex hormones, skeletal muscle relaxant combinations, skeletal muscle relaxants, smoking cessation agents, somatostatin and somatostatin analogs, spermicides, statins, sterile irrigating solutions, streptomyces derivatives, succinimide anticonvulsants, sulfonamides, sulfonylureas, synthetic ovulation stimulants, tetracyclic antidepressants, tetracyclines, therapeutic radiopharmaceuticals, therapeutic vaccines, thiazide diuretics, thiazolidinediones, thioxanthenes, third generation cephalosporins, thrombin inhibitors, thrombolytics, thyroid drugs, TNF alfa inhibitors, tocolytic agents, anesthetics, anti-infectives, antibiotics, antifungals, antihistamines, antineoplastics, antipsoriatics, antivirals, astringents, debriding agents, depigmenting agents, non-steroidal anti-inflammatories, photochemotherapeutics, chemotherapies, rubefacient, steroids, steroids with anti-infectives, triazine anticonvulsants, tricyclic antidepressants, trifunctional monoclonal antibodies, ultrasound contrast media, upper respiratory combinations, urea anticonvulsants, urinary anti-infectives, urinary antispasmodics, urinary pH modifiers, uterotonic agents, vaccine combinations, vaginal anti-infectives, vaginal preparations, vasodilators, vasopressin antagonists, vasopressors, VEGF/VEGFR inhibitors, viral vaccines, vitamin and mineral combinations, and vitamins.

List of Diseases and Conditions Treated by Therapies Administered by the Tpad-Based Devices Diseases and conditions that are treatable by the disclosed embodiments include but are not limited to, Abdominal Aortic Aneurysm, *Acanthamoeba* Infection, *Acinetobacter* Infection, Acquired Immunodeficiency Syndrome (AIDS), Adenovirus Infection, ADHD [Attention Deficit/Hyperactivity Disorder], African Trypanosomiasis, ALS [Amyotrophic Lateral Sclerosis], Alzheimer's Disease, Amebiasis; Intestinal [*Entamoeba histolytica* infection], American Trypanosomiasis, Amphibians and Fish; Infections from, Amyotrophic Lateral Sclerosis, Anaplasmosis; Human, Anemia, *Angiostrongylus* Infection, Animal-Related Diseases, *Anisakis* Infection [Anisakiasis], Anthrax, Antibiotic and Antimicrobial Resistance, Aortic Aneurysm, Arenavirus Infection, Arthritis, Childhood Arthritis, Fibromyalgia, Gout, Lupus (SLE) [Systemic lupus erythematosus], Osteoarthritis (OA), Rheumatoid Arthritis (RA), *Ascaris* Infection [Ascariasis], ASDs (Autism), Aseptic Meningitis, *Aspergillus* Infection [Aspergillosis], Asthma, Autism, autism spectrum disorders, Avian Influenza, B virus Infection [Herpes B virus], *B. cepacia* infection (*Burkholderia cepacia* Infection), Babesiosis [*Babesia* Infection], Bacterial Meningitis, Bacterial Vaginosis (BV), *Balamuthia* infection [*Balamuthia mandrillaris* infection], *Balantidium* Infection [Balantidiasis], *Baylisascaris* Infection, Bilharzia, Bioterrorism Agents/Diseases, Bird Flu, Birth Defects, Black Lung [Coal Workers' Pneumoconioses], *Blastocystis* Infection [*Blastocystis hominis* Infection], Blastomycosis, Bleeding Disorders, Blood Disorders, Body Lice [*Pediculus humanus corporis*], Bone Health, *Borrelia burgdorferi* Infection (Lyme Disease), Botulism [*Clostridium botulinim*], Bovine Spongiform Encephalopathy (BSE), Brainerd Diarrhea, Breast and Ovarian Cancer, Bronchitis, *Brucella* Infection [Brucellosis], BSE (Bovine Spongiform Encephalopathy), *Burkholderia cepacia* Infection (*B. cepacia* infection), *Burkholderia mallei, Burkholderia pseudomallei* Infection, BV (Bacterial Vaginosis), *Campylobacter* Infection [Campylobacteriosis], Cancer, Colorectal (Colon) Cancer, Gynecologic Cancers, Lung Cancer, Prostate Cancer, Skin Cancer, *Candida* Infection [Candidiasis], Canine Flu, *Capillaria* Infection [Capillariasis], Carbapenem resistant *Klebsiella* pneumonia (CRKP), Carpal Tunnel Syndrome, Cat Flea Tapeworm, Cats; Infections from, Cercarial Dermatitis, Cerebral Palsy, Cervical Cancer, CFS (Chronic Fatigue Syndrome), Chagas Disease [*Trypanosoma cruzi* Infection], Chest Cold, Chickenpox [Varicella Disease], Chikungunya Fever (CHIKV), Childhood Arthritis, Childhood Diseases, German Measles [Rubella Virus], Measles, Mumps, Rotavirus Infection, Children's Cough, Chlamydia [*Chlamydia trachomatis* Disease], *Chlamydia pneumoniae* Infection, Cholera [*Vibrio cholerae* Infection], Chronic Fatigue Syndrome (CFS), Chronic Obstructive Pulmonary Disease (COPD), Ciguatera Fish Poisoning, Classic Creutzfeldt-Jakob Disease, *Clonorchis* Infection [Clonorchiasis], *Clostridium botulinim, Clostridium difficile* Infection, *Clostridium perfringens* infection, *Clostridium tetani* Infection, Clotting Disorders, CMV (Cytomegalovirus Infection), Coal Workers' Pneumoconioses, Coccidioidomycosis, Cold; Common, Colorectal (Colon) Cancer, Concussion, Congenital Hearing Loss, Conjunctivitis, Cooleys Anemia, COPD (Chronic Obstructive Pulmonary Disease), *Corynebacterium diphtheriae* Infection, *Coxiella burnetii* Infection, CRKP (Carbapenem resistant *Klebsiella* pneumonia), Crohn's Disease, Cryptococcosis, *Cryptosporidium* Infection [Cryptosporidiosis], *Cyclospora* Infection [Cyclosporiasis], Cysticercosis, *Cystoisospora* Infection [Cystoisosporaiasis], Cytomegalovirus Infection (CMV), DBA (Diamond Blackfan Anemia), Dengue Fever (DF), Dengue Hemorrhagic Fever (DHF), Dermatophytes, Dermopathy; Unexplained, Diabetes, Diamond Blackfan Anemia (DBA), *Dientamoeba fragilis* Infection, Diphtheria [*Corynebacterium diphtheriae* Infection], *Diphyllobothrium* Infection [Diphyllobothriasis], *Dipylidium* Infection, Dog Bites, Dog Flea Tapeworm, Dogs; Infections from, Down Syndrome [Trisomy 21], Dracunculiasis, Dwarf Tapeworm [*Hymenolepis* Infection], *E. coli* Infection [*Escherichia coli* Infection], Ear Infection [Otitis Media], Eastern Equine Encephalitis (EEE), Ebola Hemorrhagic Fever, EBV Infection (Epstein-Barr Virus Infection), Echinococcosis, EEE (Eastern Equine Encephalitis), Ehrlichiosis; Human, Elephantiasis, Emerging Infectious Diseases, Encephalitis; Mosquito-Borne and Tick-Borne, *Entamoeba histolytica* infection, *Enterobius vermicularis* Infection, Enterovirus Infections (Non-Polio), Epidemic Typhus, Epilepsy, Epstein-Barr Virus Infection (EBV Infection), Ergonomic and Musculoskeletal Disorders, Extensively Drug-Resistant TB (XDR TB), Extreme Cold [Hypothermia], Extreme Heat [Hyperthermia], Farm Animals; Infections from, Fasciitis; Necrotizing, *Fasciola* Infection [Fascioliasis], *Fasciolopsis* Infection [Fasciolopsiasis], Fetal Alcohol Syndrome, Fibromyalgia, Fifth Disease [Parvovirus B19 Infection], Filariasis; Lymphatic, Fish and Amphibians; Infections from, Flavorings-Related Lung Disease, Flu; Pandemic, Flu; Seasonal, Folliculitis, Food-Related Diseases, *Clostridium perfringens* infection, Fragile X Syndrome, *Francisella tularensis* Infection, GAE (Granulomatous amebic encephalitis), GAS (Group A Strep Infection), Gastroenteritis; viral, GBS (Group B Strep Infection), Genital Candidiasis [Vulvovaginal Candidiasis (VVC)], Genital Herpes [Herpes Simplex Virus Infection], Genital Warts—Human Papillomavirus Infection, German Measles [Rubella Virus], *Giardia* Infection [Giardiasis], Glanders [*Burkholderia mallei*], Gnathostomiasis [*Gnathostoma* Infection], Gonorrhea [*Neisseria gonorrhoeae* Infection], Gout, Granulomatous amebic encephalitis (GAE), Group A Strep Infection (GAS) [Group A Streptococcal Infection], Group B Strep Infection (GBS) [Group B Streptococcal Infection], Guillain-Barré Syndrome, Guinea Worm Disease [Dracunculiasis], Gynecologic Cancers, Cervical Cancer, Ovarian Cancer, Uterine Cancer, Vaginal and Vulvar Cancers, H1N1 Flu, H5N1, *Haemophilus influenzae* Infection (Hib Infection), Hand, Foot, and Mouth Disease (HFMD), Hansen's Disease, Hantavirus Pulmonary Syndrome (HPS), Head Lice [*Pediculus humanus capitis*], Healthcare Associated Infections, Hearing Loss in Children, Heart Disease [Cardiovascular Health], Heat Stress, Hemochromatosis, Hemophilia, Hemorrhagic Fevers (VHF); Viral, Hendra Virus Infection, Hepatitis; Viral, Hereditary Bleeding Disorders, Herpes B virus, Herpes Simplex Virus Infection, Herpes Zoster, Herpes; Genital, Herpesvirus B, Herpesvirus simiae, Heterophyes Infection [Heterophyiasis], HFMD (Hand, Foot, and Mouth Disease), Hib, Hib Infection (*Haemophilus influenzae* Infection), High Blood Pressure, Histoplasmosis [*Histoplasma capsulatum* Disease], HIV/AIDS, HIV/AIDS and STDs, Hookworm; Zoonotic, Horses; Infections from, Hot Tub Rash [*Pseudomonas* dermatitis Infection], HPS (Hantavirus Pulmonary Syndrome), HPV Infection (Human Papillomavirus Infection), HPV-Associated Cancers, Human Ehrlichiosis, Human Immunodeficiency Virus, *Hymenolepis* Infection, Hypertension, Hyperthermia, Hypothermia, IBD (Inflammatory Bowel Disease), Impetigo, Infectious Mononucleosis, Infertility, Inflammatory Bowel Disease (IBD), Influenza, Avian Influenza, Pandemic Flu, Seasonal Flu, Swine Influenza, Influenza; Avian, Influenza; Pandemic, Insects and Arthropod-Related Diseases, Intestinal Amebae Infection; Nonpathogenic, Invasive Candidiasis, Iron Deficiency, Iron Overload [Hemochromatosis], *Isospora* Infection [Isosporiasis], Japanese Encephalitis, Jaundice, *K. pneumoniae* (*Klebsiella pneumoniae*), Kala-Azar, Kawasaki Syndrome (KS), Kernicterus, *Klebsiella pneumoniae* (*K. pneumoniae*), La Crosse Encephalitis (LAC), La Crosse Encephalitis virus (LACV)—see La Crosse Encephalitis, Lassa Fever, Latex Allergies, LCMV (Lymphocytic Choriomeningitis), Lead Poisoning, Legionellosis, Legionnaires' Disease [Legionellosis], *Leishmania* Infection [Leishmaniasis], Leprosy, *Leptospira* Infection [Leptospirosis], Leukemia, LGV (Lymphogranuloma venereum Infection), *Listeria* Infection [Listeriosis], Liver Disease and Hepatitis, Loiasis [Loa boa Infection], Lou Gehrig's Disease, Lung Cancer, Lupus (SLE) [Systemic lupus erythematosus], Lyme Disease [*Borrelia burgdorferi* Infection], Lymphatic Filariasis, Lymphedema, Lymphocytic Choriomeningitis (LCMV), Lymphogranuloma venereum Infection (LGV), MAC (*Mycobacterium avium* Complex), Mad Cow Disease (BSE), Malaria, Marburg Hemorrhagic Fever, Marine Toxins, MDR TB (Multidrug-Resistant TB), Measles, Melioidosis [*Burkholderia pseudomallei* Infection], Meningitis [Meningococcal Disease], Menopause, Mental Retardation, Methicillin Resistant *Staphylococcus aureus* (MRSA), Micronutrient Malnutrition, Microsporidia Infection, Molluscum Contagiosum, Monkey B virus, Monkeypox, Mononucleosis; Infectious, Morgellons, Mosquito-Borne Diseases, Motor Vehicle Injuries, MRSA (Methicillin Resistant *Staphylococcus aureus*), Mucormycosis, Multidrug-Resistant TB (MDR TB), Mumps, Musculoskeletal Disorders, *Mycobacterium abscessus* Infection, *Mycobacterium avium* Complex (MAC), *Mycobacterium tuberculosis* Infection, *Mycoplasma pneumoniae* Infection, Myelomeningocele, Myiasis, *Naegleria* Infection [Primary Amebic Meningoencephalitis (PAM)], Necrotizing Fasciitis, Neglected Tropical Diseases (NTD), *Neisseria gonorrhoeae* Infection, Neurocysticercosis, New Variant Creutzfeldt-Jakob Disease, Newborn Jaundice [Kernicterus], Nipah Virus Encephalitis, Nocardiosis, Non-Polio Enterovirus Infections, Nonpathogenic (Harmless) Intestinal Protozoa, Norovirus Infection, Norwalk-like Viruses (NLV), Novel $H_1N_1$ Flu, NTD (Neglected Tropical Diseases), OA (Osteoarthritis), Obesity Occupational Cancers, Occupational Skin Conditions, Occupational Stress, Onchocerciasis, *Opisthorchis* Infection, Oral Cancer, Orf Virus, Oropharyngeal Candidiasis (OPC), Osteoarthritis (OA), Osteoporosis, Otitis Media, Ovarian Cancer, PAD (Peripheral Arterial Disease), Pandemic Flu, Paragonimiasis, *Paragonimus* Infection [Paragonimiasis], Parasitic Diseases, Parvovirus B19 Infection, Pelvic Inflammatory Disease (PID), Peripheral Arterial Disease (PAD), Peripheral Arterial Insufficiency, Peripheral Arterial Occlusive Disease, Peripheral Vascular Disease, Pertussis, Pet-Related Diseases, PID (Pelvic Inflammatory Disease), Pink Eye [Conjunctivitis], Pinworm Infection [*Enterobius vermicularis* Infection], Plague [*Yersinia pestis* Infection], Pneumoconioses; Coal Workers', *Pneumocystis carinii* Pneumonia (PCP) Infection, *Pneumocystis jirovecii* Pneumonia, Pneumonia, Polio Infection [Poliomyelitis Infection], Poliomyelitis Infection, Pontiac Fever, Primary Amebic Meningoencephalitis (PAM), Primary Ciliary Dyskinesia, Prion Diseases [Transmissible spongiform encephalopathies (TSEs)], Prostate Cancer, *Pseudomonas* dermatitis Infection, Psittacosis, Pulmonary Hypertension, Q Fever [*Coxiella burnetii* Infection], RA (Rheumatoid Arthritis), Rabies, Raccoon Roundworm Infection [*Baylisascaris* Infection], Rat-Bite Fever (RBF) [*Streptobacillus moniliformis* Infection], Recreational Water Illness (RWI), Relapsing Fever, Reptiles; Infections from, Respiratory Syncytial Virus Infection (RSV), Rheumatoid Arthritis (RA), *Rickettsia rickettsii* Infection, *Rickettsia*; Spotted Fever Group, Rickettsial Diseases, Rift Valley Fever (RVF), Ringworm [Dermatophytes], River Blindness [Onchocerciasis], RMSF (Rocky Mountain Spotted Fever), Rodents; Diseases from, Rotavirus Infection, RSV (Respiratory Syncytial Virus Infection), Rubella Virus, Rubeola, Runny Nose, RVF (Rift Valley Fever), *Salmonella typhi* Infection, *Salmonella* Infection [Salmonellosis], SARS [Severe Acute Respiratory Syndrome], Scabies, Scarlet Fever, *Schistosoma* Infection, Schistosomiasis Seasonal Flu, Severe Acute Respiratory Syndrome, Sexually Transmitted Diseases (STDs), Bacterial Vaginosis (BV), Chlamydia [*Chlamydia trachomatis* Disease], Genital Herpes [Herpes Simplex Virus Infection], Gonorrhea [*Neisseria gonorrhoeae* Infection], Human Papillomavirus Infection (HPV Infection), Syphilis [*Treponema pallidum* Infection], SFGR (Spotted Fever Group *Rickettsia*), Shellfish-Associated Foodborne Illnesses, *Shigella* Infection [Shigellosis], Shingles [Varicella Zoster Virus (VZV)], Sickle Cell Disease, SIDS (Sudden Infant Death Syndrome), Sinus Infection [Sinusitis], Skin Cancer, Skin Conditions; Occupational, SLE (Lupus), Sleep and Sleep Disorders, Sleeping Sickness [African Trypanosomiasis], Smallpox [Variola Major and Variola Minor], Sore Mouth Infection [Orf Virus], Sore Throat, Southern Tick-Associated Rash Illness (STARI), Spina Bifida [Myelomeningocele], *Spirillum minus* Infection, Sporotrichosis, Spotted Fever Group *Rickettsia* (SFGR), St. Louis Encephalitis, Staph, *Staphylococcus aureus* Infection, STARI (Southern Tick-Associated Rash Illness), STDs (Sexually Transmitted Diseases), Stomach Flu, Strep Infection; Group A, Strep Infection; Group B, Strep Throat, *Streptobacillus moniliformis* Infection, Streptococcal Diseases, *Streptococcus pneumoniae* Infection, Stress; Occupational, Stroke, *Strongyloides* Infection [Strongyloidiasis], Sudden Infant Death Syndrome (SIDS), Swimmer's Itch [Cercarial Dermatitis], Swine Flu, Swine Influenza, Symptom Relief for Upper Respiratory Infections, Syphilis [*Treponema pallidum* Infection], Systemic lupus erythematosus, Tapeworm Infection [*Taenia* Infection], Tapeworm; Dog and Cat Flea [*Dipylidium* Infection], TB (Tuberculosis), TB and HIV Coinfections, TB in African-Americans TBI (Traumatic Brain Injury), Testicular Cancer, Tetanus Disease [*Clostridium tetani* Infection], Thalassemia, Thoracic Aortic Aneurysm, Throat; Sore, Throat; Strep, Thrombophilia, Thrombosis, Thrush [Oropharyngeal Candidiasis (OPC)], Tick-borne Relapsing Fever, Tickborne Diseases, Anaplasmosis; Human, Babesiosis [*Babesia* Infection], Ehrlichiosis; Human, Lyme Disease [*Borrelia burgdorferi* Infection], Tourette Syndrome (TS), Toxic Shock Syndrome (TSS), *Toxocara* Infection, Toxocariasis [*Toxocara* Infection], *Toxoplasma* Infection, Toxoplasmosis *Trachoma* Infection, Transmissible spongiform encephalopathies (TSEs), Traumatic Brain Injury (TBI), Traumatic Occupational Injuries, *Treponema pallidum* Infection, Trichinellosis (Trichinosis), Trichomoniasis [*Trichomonas* Infection], Trichuriasis, Trisomy 2, *Trypanosoma cruzi* Infection, Trypanosomiasis; African, TSS (Toxic Shock Syndrome), Tuberculosis (TB) [*Mycobacterium tuberculosis* Infection], Tuberculosis and HIV Coinfection, Tularemia [*Francisella tularensis* Infection], Typhoid Fever [*Salmonella typhi* Infection], Typhus Fevers, Ulcerative Colitis, Undulant Fever, Unexplained Dermopathy, Unexplained Respiratory Disease Outbreaks (URDO), Upper Respiratory Infection Symptom Relief, URDO (Unexplained Respiratory Disease Outbreaks), Uterine Cancer, Vaginal and Vulvar Cancers, Vaginal Yeast Infection, Vancomycin-Intermediate/Resistant *Staphylococcus aureus* Infections [VISA/VRSA], Vancomycin-resistant Enterococci Infection (VRE), Variant Creutzfeldt-Jakob Disease (vCJD), Varicella Disease, Varicella Zoster Virus (VZV), Varicella-Zoster Virus Infection, Variola Major and Variola Minor, *Vibrio cholerae* Infection, *Vibrio parahaemolyticus* Infection, *Vibrio vulnificus* Infection, Viral Gastroenteritis, Viral Hemorrhagic Fevers (VHF), Viral Hepatitis, Viral Meningitis [Aseptic Meningitis], Vision Impairment, Von Willebrand Disease VRE (Vancomycin-resistant Enterococci Infection), Vulvovaginal Candidiasis (VVC), VZV (Varicella Zoster Virus), West Nile Virus Infection, Western Equine Encephalitis Infection, Whipworm Infection [Trichuriasis], Whitmore's Disease, Whooping Cough, Wildlife; Infections from, Women's Bleeding Disorders, XDR TB (Extensively Drug-Resistant TB), Xenotropic Murine Leukemia Virus-related Virus Infection—(XMRV Infection, Yellow Fever, *Yersinia enterocolitica* Infection, *Yersinia pestis* Infection, Yersiniosis [*Yersinia enterocolitica* Infection], Zoonotic Hookworm and Zygomycosis.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Although many of the medicaments shown and described above have been described as being in liquid form, in some embodiments, any of the compositions and/or medicaments can be in a lyophilized form that is reconstituted prior to administration. Similarly stated, in some embodiments, a cartridge can include a first portion of the medicament stored as a dry component and second portion of the medicament stored as liquid diluent.

Although various embodiments have been described as having particular features and/or combinations of components, other embodiments are possible having a combination of any features and/or components from any of embodiments where appropriate. For example, in some embodiments, a medicament delivery device can include an electronic circuit system configured to produce a first electronic signal when the device is actuated, similar to the medicament delivery device 3002, and a second electronic signal based upon the impedance between various portions of the device, similar to the medicament delivery device 15002.

In some embodiments, an aerosol delivery system for delivery of an aerosol to a patient includes an entrainment chamber having an aerosol inlet configured to receive an aerosol generated by an aerosol device to the entrainment chamber, a fluid inlet and a fluid outlet. The fluid inlet is configured to receive an entrainment fluid from a source gas such that the aerosol from the aerosol inlet is entrained in the entrainment fluid flowing in a flow pathway from the fluid inlet, through the entrainment chamber, to the fluid outlet. A particle selection chamber is connected to the fluid outlet of the entrainment chamber. The particle selection chamber is configured to be connected to a nasal cannula and the particle selection chamber is sized and/or configured such that an output from the particle selection chamber and/or the nasal cannula has a combined rainout (e.g., collected within the cannula) and sputter of less than about 10 mL when operating at a an output rate of more than about 0.01 µL/min for at least about thirty minutes, for up to eight hours, and/or for up to 24 hours per day.

In some embodiments, an apparatus includes an entrainment chamber and a particle selection chamber coupled to the entrainment chamber. The entrainment chamber is sized and configured such that an entrainment fluid has a first velocity within the entrainment chamber and a second velocity as the entrainment fluid exits the entrainment chamber fluid outlet, the second velocity being greater than the first velocity.

In some embodiments, the combination of the airflow, jet diameter and impaction baffle of an aerosol preparation assembly is sized and configured to reduce an amount of aerosol particles in the entrainment fluid that are greater than a predetermined diameter. In some embodiments, the predetermined diameter of the particles that impact into the baffle is greater than 3 to 4 µm. The impaction baffle may be sized and configured to generally allow aerosol particles that are less than the predetermined diameter to pass around the impaction baffle, the particle size selection chamber and the particle size selection chamber outlet.

In some embodiments, a method of delivering an aerosol to a patient includes providing a source of pulsatile or non-pulsatile gas flow, an entrainment fluid to an entrainment chamber having an aerosol therein. The entrainment fluid and aerosol is passed through a particle selection chamber. The particle selection chamber is sized and configured such that the flow pathway of the entrainment chamber forms a spiral shape having a plurality of generally circular loops.

What is claimed is:
1. An apparatus comprising:
   an entrainment chamber defining an entrainment volume, the entrainment chamber including a gas inlet port, an aerosol inlet port and an outlet port, the gas inlet port configured to fluidically couple a gas source to the entrainment volume, the entrainment chamber configured such that a velocity of a flow of a gas within the entrainment volume is less than a velocity of the flow of the gas within the gas inlet port, the aerosol inlet port configured to receive an inlet aerosol produced by an aerosol generator, the entrainment chamber configured such that at least a portion of the inlet aerosol is entrained into the flow of the gas within the entrainment volume to produce an entrained aerosol flow at the outlet port;
a nozzle in fluidic communication with the outlet port of the entrainment chamber, the nozzle configured to accelerate the entrained aerosol flow; and
a particle selection chamber including a cannula coupling port configured to be coupled to a nasal cannula, the particle selection chamber configured to receive the entrained aerosol flow from the nozzle and produce an outlet aerosol flow, the particle selection chamber including an obstructive structure configured to remove particles from the entrained aerosol flow such that a volumetric median diameter of the outlet aerosol flow is less than a volumetric median diameter of the inlet aerosol.

2. The apparatus of claim 1, wherein the inlet port of the entrainment chamber has an expansion ratio entering the entrainment volume of at least two.

3. The apparatus of claim 1, wherein the nozzle is monolithically constructed with at least one of the entrainment chamber or the particle selection chamber.

4. The apparatus of claim 1, wherein the entrainment chamber and the particle selection chamber are monolithically constructed.

5. The apparatus of claim 1, wherein the obstructive structure defines a tortuous path.

6. The apparatus of claim 1, wherein the obstructive structure includes a baffle, the nozzle and the baffle configured such that a portion of the entrained aerosol particles impinges on the baffle.

7. The apparatus of claim 1, further comprising at least one of the following:
a first recirculation port defined by the entrainment chamber, the first recirculation port configured to receive a rained out portion of the inlet aerosol, the first recirculation port fluidically coupled to the aerosol generator; or
a second recirculation port defined by the particle selection chamber, the second recirculation port configured to receive a rained out portion of the entrained aerosol flow, the second recirculation port fluidically coupled to the aerosol generator.

8. The apparatus of claim 1, wherein the obstructive structure and the nozzle are collectively configured such that the volumetric median diameter of the outlet aerosol flow is substantially independent of the volumetric median diameter of the inlet aerosol.

9. The apparatus of claim 1, wherein the obstructive structure and the nozzle are collectively configured such that the volumetric median diameter of the outlet aerosol flow is between approximately one micron and approximately two microns when the volumetric median diameter of the inlet aerosol is within a range of between approximately two microns and approximately seven microns.

10. The apparatus of claim 1, wherein the obstructive structure and nozzle are collectively configured such that the volumetric median diameter of the outlet aerosol flow is between approximately one micron and approximately two microns.

11. The apparatus of claim 1, wherein the cannula coupling port includes a cannula nozzle and a coupling portion, an effective flow area of a flow path defined by an inner wall of the cannula nozzle being substantially the same as an effective flow area of a flow path defined by an inner wall of the nasal cannula, the coupling portion configured to be coupled to the nasal cannula such that the inner wall of the cannula nozzle and the inner wall of the nasal cannula form a substantially continuous surface.

12. The apparatus of claim 1, further comprising:
the gas source, the gas source configured to produce the flow of a gas within the entrainment volume having a periodic variation in flow rate.

13. The apparatus of claim 1, further comprising:
a cartridge in fluid communication with the aerosol generator, the cartridge containing a medicament from which the inlet aerosol is produced by the aerosol generator.

14. The apparatus of claim 13, wherein the medicament includes hypertonic saline.

15. An apparatus comprising:
an entrainment chamber defining an entrainment volume, the entrainment chamber including a gas inlet port, an aerosol inlet port and an outlet port, the gas inlet port configured to fluidically couple a gas source to the entrainment volume, the aerosol inlet port configured to receive an inlet aerosol produced by an aerosol generator, the entrainment chamber configured such that at least a portion of the inlet aerosol is entrained into a flow of a gas within the entrainment volume to produce an entrained aerosol flow at the outlet port; and
a particle selection chamber including a cannula coupling port configured to be coupled to a nasal cannula, the particle selection chamber configured to receive the entrained aerosol flow from the outlet port of the entrainment chamber and produce an outlet aerosol flow, the particle selection chamber including an obstructive structure configured to remove particles from the entrained aerosol flow such that a volumetric median diameter of the outlet aerosol flow is less than a volumetric median diameter of the inlet aerosol,
the cannula coupling port including a cannula nozzle and a coupling portion, the coupling portion configured to be coupled to the nasal cannula such that an inner wall of the cannula nozzle and an inner wall of the nasal cannula form a substantially continuous surface.

16. The apparatus of claim 15, further comprising:
a nozzle fluidically coupled to the outlet port of the entrainment chamber, the nozzle configured to accelerate the entrained aerosol flow between the entrainment chamber and the particle selection chamber,
the obstructive structure including a baffle, the nozzle and the baffle configured such that a portion of the entrained aerosol in the entrained aerosol flow impinges on the baffle.

17. The apparatus of claim 15, further comprising at least one of the following:
a first recirculation port defined by the entrainment chamber, the first recirculation port configured to receive a rained out portion of the inlet aerosol, the first recirculation port fluidically coupled to the aerosol generator; or
a second recirculation port defined by the particle selection chamber, the second recirculation port configured to receive a rained out portion of the entrained aerosol flow, the second recirculation port fluidically coupled to the aerosol generator.

18. An apparatus comprising:
an entrainment chamber defining an entrainment volume, the entrainment chamber including a gas inlet port, an aerosol inlet port, and an outlet port, the gas inlet port configured to fluidically couple a gas source to the entrainment volume, the aerosol inlet port configured to receive an inlet aerosol produced by an aerosol generator, the entrainment chamber configured such that a first portion of the inlet aerosol is entrained into a flow of a gas within the entrainment volume to produce an entrained aerosol flow at the outlet port and a second portion of the inlet aerosol is collected within the entrainment chamber;
a particle selection chamber including a cannula coupling port configured to be coupled to a nasal cannula, the particle selection chamber configured to receive the entrained aerosol flow from the outlet port of the entrainment chamber and produce an outlet aerosol flow, the particle selection chamber configured to extract a portion of the entrained aerosol from the entrained aerosol flow such that a volumetric median diameter of the outlet aerosol flow is less than a volumetric median diameter of the inlet aerosol; and
a recirculation port defined by one of the entrainment chamber or the particle selection chamber, the recirculation port configured to receive one of the second portion of the inlet aerosol or the extracted portion of the entrained aerosol, the recirculation port fluidically coupled to the aerosol generator via a recirculation pathway that excludes at least one of the entrainment chamber or the particle selection chamber.

19. The apparatus of claim 18, wherein:
the outlet port includes a nozzle configured to accelerate the entrained aerosol flow between the entrainment chamber and the particle selection chamber; and
the particle selection chamber includes a baffle, the nozzle and the baffle configured such that at least a portion of the extracted portion of the entrained aerosol flow impinges on the baffle.

20. The apparatus of claim 18, wherein the cannula coupling port includes a cannula nozzle and a coupling portion, the coupling portion configured to be coupled to the nasal cannula such that an inner wall of the cannula nozzle and an inner wall of the nasal cannula form a substantially continuous surface.

21. The apparatus of claim 18, further comprising:
a cartridge in fluid communication with the aerosol generator, the cartridge containing a medicament from which the inlet aerosol is produced by the aerosol generator,
wherein the recirculation port is fluidically coupled to the cartridge.

22. The apparatus of claim 18, wherein the medicament includes hypertonic saline.

23. The apparatus of claim 18, wherein the recirculation port is a first recirculation port defined by the entrainment chamber, the recirculation pathway is a first recirculation pathway, the first recirculation port configured to receive the second portion of the inlet aerosol, the first recirculation port fluidically coupled to the aerosol generator via the first recirculation pathway that excludes the entrainment chamber, the apparatus further comprising:
a second recirculation port defined by the particle selection chamber, the second recirculation port configured to receive the extracted portion of the entrained aerosol, the second recirculation port fluidically coupled to the aerosol generator via a second recirculation pathway that excludes the particle selection chamber.

24. An apparatus comprising:
an entrainment chamber defining an entrainment volume, the entrainment chamber including a gas inlet port, an aerosol inlet port and an outlet port, the gas inlet port configured to fluidically couple a gas source to the entrainment volume, the aerosol inlet port configured to receive an inlet aerosol produced by an aerosol generator, the entrainment chamber configured such that at least a portion of the inlet aerosol is entrained into a flow of a gas within the entrainment volume to produce an entrained aerosol flow at the outlet port; and
a particle selection chamber including a cannula coupling port configured to be coupled to a nasal cannula, the particle selection chamber configured to receive the entrained aerosol flow from the outlet port of the entrainment chamber and produce an outlet aerosol flow, the particle selection chamber defining a tortuous path configured to remove particles from the entrained aerosol flow such that a volumetric median diameter of the outlet aerosol flow is less than a volumetric median diameter of the inlet aerosol.

* * * * *